United States Patent
Ohtani et al.

[11] Patent Number: 5,955,616
[45] Date of Patent: Sep. 21, 1999

[54] PYRROLIDINE DERIVATIVES HAVING PHOSPHOLIPASE $A_2$ INHIBITORY ACTIVITY

[75] Inventors: Mitsuaki Ohtani, Nara; Toshiyuki Kato, Suita; Fumihiko Watanabe, Kitakatsuragi-gun; Kaoru Seno, Nishinomiya, all of Japan

[73] Assignee: Shionogi & Co., Ltd., Osaka, Japan

[21] Appl. No.: 09/011,404

[22] PCT Filed: Jul. 25, 1996

[86] PCT No.: PCT/JP96/02079

§ 371 Date: Jan. 28, 1998

§ 102(e) Date: Jan. 28, 1998

[87] PCT Pub. No.: WO97/05135

PCT Pub. Date: Feb. 13, 1997

[30] Foreign Application Priority Data

Jul. 31, 1995 [JP] Japan ................................ 7-194648

[51] Int. Cl.⁶ .............. C07D 417/12; C07D 417/14; C07D 413/12; A61K 31/425; A61K 31/42; A61K 31/44
[52] U.S. Cl. .............. 548/183; 514/369; 514/376; 548/226; 548/227
[58] Field of Search ...................... 548/183, 226, 548/227; 514/369, 376

[56] References Cited

U.S. PATENT DOCUMENTS

| | | |
|---|---|---|
| 4,331,668 | 5/1982 | Roantree et al. ............ 424/263 |
| 5,130,379 | 7/1992 | Clark et al. ................ 514/333 |
| 5,521,202 | 5/1996 | Yano et al. ................ 514/369 |
| 5,747,501 | 5/1998 | Macor et al. .............. 514/376 |

FOREIGN PATENT DOCUMENTS

| | | | |
|---|---|---|---|
| 0258914 | 3/1988 | European Pat. Off. ........ 548/183 |
| 4317320 | 12/1994 | Germany ................ 548/183 |
| 6-184098 | 7/1994 | Japan .................. 548/183 |
| 2250298 | 6/1992 | United Kingdom .......... 548/183 |
| 95/10508 | 4/1995 | WIPO ................... 548/183 |

*Primary Examiner*—Floyd D. Higel
*Attorney, Agent, or Firm*—Foley & Lardner

[57] ABSTRACT

A compound of the formula I:

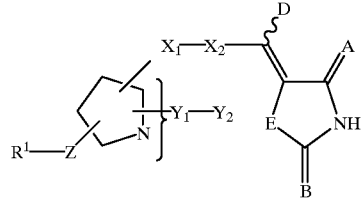

or a pharmaceutically acceptable salt or a hydrate thereof, which has the activity of inhibiting the production of prostaglandin $E_2$ by inhibiting cytosolic phospholipase$_2$.

15 Claims, No Drawings

PYRROLIDINE DERIVATIVES HAVING PHOSPHOLIPASE A₂ INHIBITORY ACTIVITY

This application is a 371 of PCT/JP96/02079, filed Jul. 25, 1996.

TECHNICAL FIELD

The present invention relates to novel pyrrolidine derivatives having an activity of inhibiting cytosolic phospholipase $A_2$, and pharmaceutical compositions for inhibiting the cytosolic phospholipase $A_2$ which contain a novel pyrrolidine derivative as an active ingredient.

BACKGROUND ART

Phospholipase $A_2$ ($PLA_2$) is a protein capable of specifically hydrolyzing 2-acyl ester bond(s) of phospholipids, and includes cytosolic $PLA_2$ ($cPLA_2$) and secretory type $PLA_2$ ($sPLA_2$) which are clearly distinguishable.

It is known that $cPLA_2$ can selectively hydrolyze phospholipids containing arachidonic acid which is esterified at the 2-position. Accordingly, the prevention of $cPLA_2$ activity would inhibit the release of arachidonic acid from phospholipids. Arachidonic acid is a precursor of prostaglandins and leukotrienes, which are biological substances known to be participating in the onset of inflammation. These inflammatory substances are produced through a series of processes so called "arachidonate cascade". Therefore, the inhibition of the release of arachidonic acid would suppress the activity of various substances involved in inflammation and is useful in the prevention or treatment of inflammatory diseases. Examples of such disease include rheumatoid arthritis, asthma, inflammatory bowel disease, injury due to ischemic reperfusion, allergic rhinitis, and psoriasis.

However, there have not been provided any substances which have highly specific activity of inhibiting cPLA2 and are clinically applicable. It has been disclosed that compounds having phenoxy group between thiazolidione and pyrrolidine rings, which pyrrolidine ring is substituted at the N-atom with benzoxazole, etc., are effective on non-insulin dependent diabetes, or the like. See, Japanese Patent Publication (KOKAI) No. 213913/1993 corresponding to France Patent Application, Priority Claiming No. 9110430, Priority date: Aug. 20, 1991. However, there is no description about compounds having phospholipase $A_2$ inhibitory activity in the said literature.

DISCLOSURE OF INVENTION

The present inventors have intensively studied for developing specific $cPLA_2$ inhibitors and found that certain kinds of novel pyrrolidine derivatives, especially those having partial structure of thiazolidinedione or oxazolidinedione, possess a potent $cPLA_2$ inhibitory activity. Thus, the present invention provides a compound of the formula I:

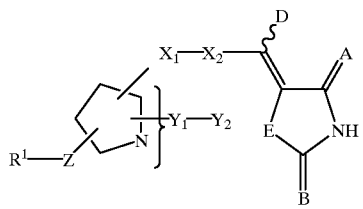

wherein A and B are independently O or S; E is O or S; $X_1$ is —CO—, —CONH—, —CH$_2$NHSO$_2$—, —CH$_2$NHCO—, —CH$_2$NHCS—, —CH$_2$O—, —OCH$_2$—, —CH$_2$OCH$_2$—, alkylene, alkenylene or a single bond; $X_2$ is optionally substituted arylene, optionally substituted indoldiyl or a single bond; D is hydrogen or hydroxyalkyl; $Y_1$ is —(CH$_2$)$_m$CO—, —(CH$_2$)$_n$NHCO—, —(CH$_2$)$_n$NHSO$_2$—, —(CH$_2$)$_m$CONH—, —(CH$_2$)$_m$CSNH—, —(CH$_2$)$_m$SO$_2$—, —(CH$_2$)$_m$COO—, or a single bond; m and n are an integer of 0 to 3; $Y_2$ is hydrogen, alkyl, optionally substituted alkenyl, optionally substituted cycloalkyl, optionally substituted cycloalkenyl, optionally substituted cycloalkylalkyl, optionally substituted cycloalkenylalkyl, optionally substituted aryl, optionally substituted aralkyl, optionally substituted heterocyclic group or optionally substituted amino; Z is —S—, —SO—, —O—, —NH—, —CONH—, —CONHCH$_2$— or a single bond; $R^1$ is hydrogen, optionally substituted alkyl, optionally substituted alkenyl, optionally substituted aryl or optionally substituted aralkyl, or a pharmaceutically acceptable salt or a hydrate thereof, provided that when $X_1$ is —CH$_2$O—, $Y_1$ is not a single bond; $Y_1$ binds to the pyrrolidine ring at 1- or 2-position, $X_1$ binds to any positions other than the one to which $Y_1$ binds (provided that when $Y_1$ is at the 2-position, $X_1$ binds to the 1-position), and Z binds to any one of carbon atoms on the pyrrolidine ring other than those to which $X_1$ and $Y_1$ bind; when $Y_1$ binds to the N-atom on the pyrrolidine ring, n is not 0; when $Y_1$ is —(CH$_2$)$_m$ COO— and m is 0, $Y_2$ is not H; and when $X_1$ is —OCH$_2$—, it does not bind to the N-atom on the pyrrolidine ring.

For purposes of the present invention, all the compounds as defined above are preferred. However, compounds of preferred embodiment are shown by the formula Ia:

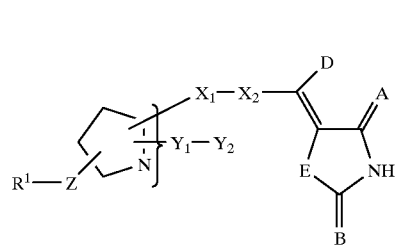

wherein A, B, E, $X_1$, $X_2$, D, $Y_1$, $Y_2$, Z and $R^1$ are as defined above, or a pharmaceutically acceptable salt or a hydrate thereof, provided that when $X_1$ is —CH$_2$O—, $Y_1$ is not a single bond; $Y_1$ binds to the pyrrolidine ring at the 1- or 2-position and when $Y_1$ binds to the 1-position, $X_1$ binds to the 2-position and when $Y_1$ binds to the 2-position, $X_1$ binds to the 1-position, and Z binds to any one of carbon atoms on the pyrrolidine ring other than those to which $X_1$ and $Y_1$ bind; when $Y_1$ binds to the N-atom on the pyrrolidine ring, n is not 0; when $Y_1$ is —(CH$_2$)$_m$ COO— and m is 0, $Y_2$ is not H; and when $X_1$ is —OCH$_2$—, it does not bind to the N-atom on the pyrrolidine ring.

Specific examples include a compound of the formula Ib:

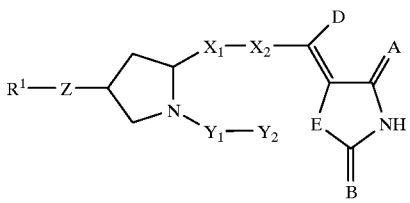

Ib wherein A, B, E, $X_1$, $X_2$, D, $Y_1$, $Y_2$, Z and $R^1$ are as defined above, or a pharmaceutically acceptable salt or a hydrate thereof, provided that when $X_1$ is —$CH_2O$—, $Y_1$ is not a single bond; n is not 0; when $Y_1$ is —$(CH_2)_m COO$— and m is 0, $Y_2$ is not H.

Similarly, examples include a compound of the formula Ic:

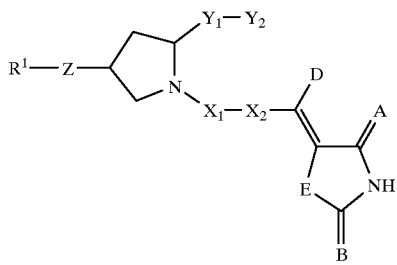

Ic wherein A, B, E, $X_1$, $X_2$, D, $Y_1$, $Y_2$, Z and $R^1$ are as defined above, or a pharmaceutically acceptable salt or a hydrate thereof, provided that when $X_1$ is —$CH_2O$—, $Y_1$ is not a single bond; when $X_1$ is —$OCH_2$—, it does not bind to the N-atom on pyrrolidine ring.

Similarly, examples include a compound of the formula Id:

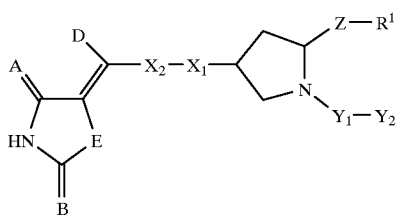

Id wherein A, B, E, $X_1$, $X_2$, D, $Y_1$, $Y_2$, Z and $R^1$ are as defined above, or a pharmaceutically acceptable salt or a hydrate thereof, provided that when $X_1$ is —$CH_2O$—, $Y_1$ is not a single bond; n is not 0; when $Y_1$ is —$(CH_2)_m COO$— and m is 0, $Y_2$ is not H. Examples of a compound of more preferred embodiments are as follows.

1) A compound wherein E is S, and A and B are O, or a pharmaceutically acceptable salt or a hydrate thereof.
2) A compound wherein $X_1$ is —CONH—, —$CH_2NHSO_2$— or —$CH_2NHCO$—, or a pharmaceutically acceptable salt or a hydrate thereof.
3) A compound wherein $X_2$ is optionally substituted phenylene, or a pharmaceutically acceptable salt or a hydrate thereof.
4) A compound wherein $Y_1$ is —CO—, —CONH— or —$SO_2$—, or a pharmaceutically acceptable salt or a hydrate thereof.
5) A compound wherein $Y_2$ is optionally substituted cycloalkenylalkyl, optionally substituted aryl, optionally substituted aralkyl or optionally substituted heterocyclic group, or a pharmaceutically acceptable salt or a hydrate thereof.
6) A compound wherein Z is —S— or —O—, or a pharmaceutically acceptable salt or a hydrate thereof.
7) A compound wherein $R^1$ is optionally substituted alkyl or optionally substituted aralkyl, or a pharmaceutically acceptable salt or a hydrate thereof.

The term "alkyl" means $C_1$–$C_{15}$ straight or branched chain alkyl, for example, methyl, ethyl, propyl, n-butyl, i-butyl, t-butyl, n-pentyl, n-hexyl, i-hexyl, n-heptyl, t-heptyl, i-heptyl, n-octyl, i-octyl, 3,7-dimethyloctyl, n-nonyl, n-decyl, n-undecyl, n-dodecyl, and the like. The alkyl may have one or more substituents selected from the group consisting of halogen, alkoxy, oxo, phenyl (e.g., 4-nitrophenyl, 4-methoxyphenyl) and phenylsulfonyl.

The term "alkenyl" means $C_2$–$C_{10}$ straight or branched chain alkenyl, for example, vinyl, allyl, propenyl, and the like. The alkenyl may have one or more substituents selected from the group consisting of halogen, alkoxy and phenyl. The phenyl may also have a substituent(s), for example, halogen, alkoxy, alkylenedioxy, and the like.

Examples of "hydroxyalkyl" include hydroxymethyl, hydroxyethyl, and the like, and hydroxymethyl is preferred.

The term "cycloalkyl" means $C_3$–$C_{12}$ cycloalkyl, for example, cyclopropyl, cyclobutyl, cyclopentyl, cyclohexyl, and the like.

The term "cycloalkylalkyl" refers to a group wherein alkyl group is substituted with $C_3$–$C_{12}$ cycloalkyl group, for example, cyclopropylmethyl, cyclobutylmethyl, cyclopentylethyl, and the like.

The term "cycloalkenyl" means $C_3$–$C_{12}$ cycloalkenyl, for example, cyclopropenyl, cyclobutenyl, cyclopentenyl, cyclopentadienyl (e.g., 1,3-cyclopentadien-1-yl), cyclohexadienyl (e.g., 1,4-cyclohexadien-1-yl), and the like.

The term "cycloalkenylalkyl" refers to a group wherein alkyl group is substituted with $C_3$–$C_{12}$ cycloalkenyl group, for example, cyclopropenylmethyl, cyclobutenylethyl, cyclopentanylmethyl, cyclopentadienylmethyl, cyclohexadienylhexyl (e.g., 1,4-cyclohexadienylhexyl), dihydronaphthylhexyl (e.g., 1,4-dihydronaphthylhexyl), and the like.

The substituent (s) on the above-mentioned "cycloalkyl", "cycloalkenyl", cycloalkylalkyl" and "cycloalkenylalkyl" is the same as that described in the definition for "alkyl".

The term "optionally substituted amino" means mono- or di-substituted amino or cyclic amino, for example, dimethylamino, diethylamino, ethylmethylamino, morpholino, piperidino, piperadino, and the like.

The term "alkylene" means a group derived from $C_1$–$C_4$ alkyl, for example, methylene, ethylene, trimethylene and tetramethylene.

The term "alkenylene" means a group derived from $C_2$–$C_4$ alkenyl, for example, vinylene, propenylene and butenylene.

The term "aryl" refers to, for example, phenyl, naphthyl, and the like, and phenyl is preferred. The aryl may has one or more substituents selected from the group consisting of phenyl, halogen, alkyl, alkoxy, trifluoromethyl, alkylenedioxy, acyl, carboxy, alkoxycarbonyl, carbamoyl, hydroxymethyl, amino, nitrile and benzhydryl, acylamino (e.g., acetylamino), cyanoalkoxy (e.g., 3-cyanopropoxy), phenylazo, arylsulfonyl (e.g., phenylsulfonyl), nitro, aralkyl (e.g., benzyl), 3-oxoisothiazolin-2-yl, 2-oxopyrrolidin-1-yl, cyanothiocarbonylamino, 1,1,3-trioxo-1,2-benzisothiazol-2-ylmethoxy, t-butyldimethylsilyl, hydroxy, acyloxy (e.g., acetyloxy), oxo, 2-oxoisothiazolin-2-ylmethyl, alkoxycarbonylamino (e.g., t-butyloxycarbonylamino), alkoxycarbonyl (e.g., methoxycarbonyl), alkoxycarbonylalkyl (e.g., methoxycarbonylethyl) and hydroxyalkyl (e.g., hydroxypropyl). Examples of preferred substituents include carboxy, carbamoyl, halogen, methyl, methoxy, trifluoromethyl, and the like. Accordingly, examples of aryl include 2-fluorophenyl, 3-fluorophenyl, 4-fluorophenyl, 2,3-difluorophenyl, 2,6-difluorophenyl, 4-chlorophenyl, 2,4-dichlorophenyl, 2,6-dichlorophenyl, 4-bromophenyl, 2,4-dibromophenyl, 4-methylphenyl, 4-ethylphenyl, 4-t-butylphenyl, 3,5-di-t-butylphenyl, 2-methoxyphenyl, 3-methoxyphenyl, 4-methoxyphenyl, 2,3-dimethoxyphenyl, 2,6-dimethoxyphenyl, 2,4-dimethoxyphenyl, 3,4-dimethoxyphenyl, 3,5-dimethoxyphenyl, 3,4-methylenedioxyphenyl, 3,4-ethylenedioxyphenyl, 2-acetylphenyl, 3-acetylphenyl, 4-acetylphenyl, 4-acetylaminophenyl, 4-acetylamino-3,5-dichlorophenyl, 2-carboxyphenyl, 3-carboxyphenyl, 4-carboxyphenyl, 2-methoxycarbonylphenyl, 3-methoxycarbonylphenyl, 4-methoxycarbonylphenyl, 2-ethoxycarbonylphenyl, 3-ethoxycarbonylphenyl, 4-ethoxycarbonylphenyl, 2-carbamoylphenyl, 3-carbamoylphenyl, 4-carbamoylphenyl, 4-benzhydrylphenyl, 4-trifluoromethylphenyl, 4-N,N-dimethylaminophenyl, 4-phenylazophenyl 4-benzylphenyl, 5-dimethylamino-1-naphthyl, 1,4-dihydro-2-naphthyl, and the like.

The definition of aryl includes not a group containing a single aryl group but also a group containing two or more aryl groups in series such as diphenyl group.

The term "arylene" means, for example, phenylene and naphthalene such as 1,2-phenylene, 1,3-phenylene, 1,4-phenylene, and the like.

The substituents on the aryl of "arylene" or "indol-diyl" can be the same as those on "aryl".

The term "aralkyl (arylalkyl)" is a group formed by substituting an alkyl with an aryl as defined above. Examples include benzyl, phenethyl, and the like. The aryl moiety in the arylalkyl may have substituents as mentioned above. Accordingly, examples of aralkyl include benzyl, 1-naphthylmethyl, 2-naphthylmethyl, a 4-methylphenylmethyl, 2,4,6-trimethyphenyl-methyl, 3,5-di-t-butyl-4-methoxyphenyl, biphenylmethyl, 4-fluorophenylmethyl, 4-bromophenylmethyl, 4-chorophenylmethyl, 2,6-dichlorophenylmethyl, 2,4-difluorophenylmethyl, 4-trifluorophenylmethyl, 2,4-ditrifluorophenylmethyl, 2-methyl-4-trifluorophenylmethyl, 4-methoxyphenylmethyl, 3,4,5-trimethoxyphenylmethyl, 4-methoxycarbonylphenylmethyl, 4-carboxyphenylmethyl, 4-carbamoylphenylmethyl, 4-cyanopropyloxyphenylmethyl, 4-nitropheylmethyl, benzhydryl, di-(4'-fluorophenyl)methyl, triphenylmethyl, and the like.

The term "heterocyclic group" means a cyclic group containing one or more hetero atoms selected from the group consisting of oxygen, sulfur or nitrogen atom on the ring, and is optionally condensed with a carbon ring. Examples include pyrrolyl (e.g., 2-pyrrolyl), indolyl (e.g., 2-indolyl), isoindolyl (e.g., 3-isoindolyl), pyrazolyl (e.g., 4-pyrazolyl), carbazolyl (e.g., 5-carbazolyl), quinolyl (e.g., 8-quinolyl), benzimidazolyl (e.g., 5-benzimidazolyl), phenoxathiinyl (e.g., 2-phenoxathiinyl), phenoxazinyl (e.g., 3-phenoxdinyl), benzisoxazolyl (e.g., 1,2-benzisoxazol-1-yl), benzothiazolyl (e.g., 2-benzothiazolyl), benzoxazolyl (e.g., 6-benzoxazolyl), pyridyl (e.g., 2-pyridyl), thiazolyl (e.g., 5-thiazolyl), azetidinyl (e.g., azetidin-2-yl), and the like.

The substituent on the "optionally substituted-heterocyclic group" can be the same as those for aryl.

The term "halogen" means fluorine, chlorine, bromine, and iodine.

Examples of pharmaceutically acceptable salts include salts formed with an alkali metal such as potassium or sodium, an alkali earth metal such as calcium, or the like.

Further, the compound of he present invention and its salt can form a hydrate.

The Best Embodiment for Practicing the Invention

Although the compound I of the present invention can be prepared in a conventional manner, it is conveniently prepared according to either of the processes shown below depending on the type of the aimed compounds. The following processes are, however, provided just for illustrative purpose and compounds I prepared by any other methods also fall within the scope of the invention.

1) Compounds having sulfur atom at the 4-position of pyrrolidine ring (Z=—S—)

Method A: Compounds having amide group at the 2-position of pyrrolidine ring ($X_1$=—CONH—).

Method B: Compounds having alkylene group at the 2-position of pyrrolidine ring.

Method $B_1$: Compounds having amide or sulfonamide group at the 2-position of pyrrolidine ring via alkylene group ($X_1$=—CH$_2$NHCO—, —CH$_2$NHSO$_2$— or —CH$_2$NHCS—).

Method $B_2$: Compounds having thiazolidinedione group at the 1-position of pyrrolidine ring ($X_1$=—CO—).

Method C: Compounds wherein thiazolidinedione is substituted at a different position(s) ($X_1$=—CONH—).

Method D: Compounds having hydroxyalkyl group on double bond (D=hydroxyalkyl).

Method $E_1$: Compounds which do not have an amide bond at the 2-position of pyrrolidine ring but have a carbon- or ether-bond directly linked thereto ($X_1$=—CH$_2$OCH$_2$— or —CH$_2$O—).

Method $E_2$: Compounds having carbon bond at the 2-position of pyrrolidine ring ($X_1$ is alkylene or alkenylene).

Method F: Compounds having thiazolidinedione at the 2-position of pyrrolidine ring ($X_1$=single bond, $X_2$=single bond).

2) Compounds having oxygen atom at the 4-position of pyrrolidine ring (Z=—O—).

Method G: Compounds having amide group at the 2-position of pyrrolidine ring ($X_1$=—CONH—).

Method H: Compounds having alkylene group at the 2-position of pyrrolidine ring ($X_1$=—CH$_2$NHCO—, —CH$_2$NHSO$_2$— or —CH$_2$NHCS—).

Method I: Compounds having hydroxyalkyl group on the double bond (D=hydroxyalkyl).

3) Compounds having nitrogen atom at the 4-position of pyrrolidine ring (Z=—NH— or —CONH—).

Method J

4) Compounds having carbon atom at the 4-position of pyrrolidine ring (Z=single bond).

Method K

5) Proline derivative (Z=single bond, $R^1$=hydrogen)

Method L: Compounds wherein pyrrolidine ring has no substituents at the 4-position.

6) Compounds having sulfur atom at the 4-position of pyrrolidine ring and exhibiting different configuration at the 2- and 4-positions of pyrrolidine ring.

Method M: Compounds of the configuration of (2β,4α), (2α, 4β) or (2α, 4α) having sulfur atom at the 4-position of pyrrolidine ring. Compounds having sulfur atom at the 4-position of pyrrolidine ring prepared according to the method of item 1) above are in (2β, 4β) configuration.

Method N

7) Compounds having thiazolidinedione at the 4-position of pyrrolidine ring.

The methods above will be hereinafter described in more detail.

< Method A >

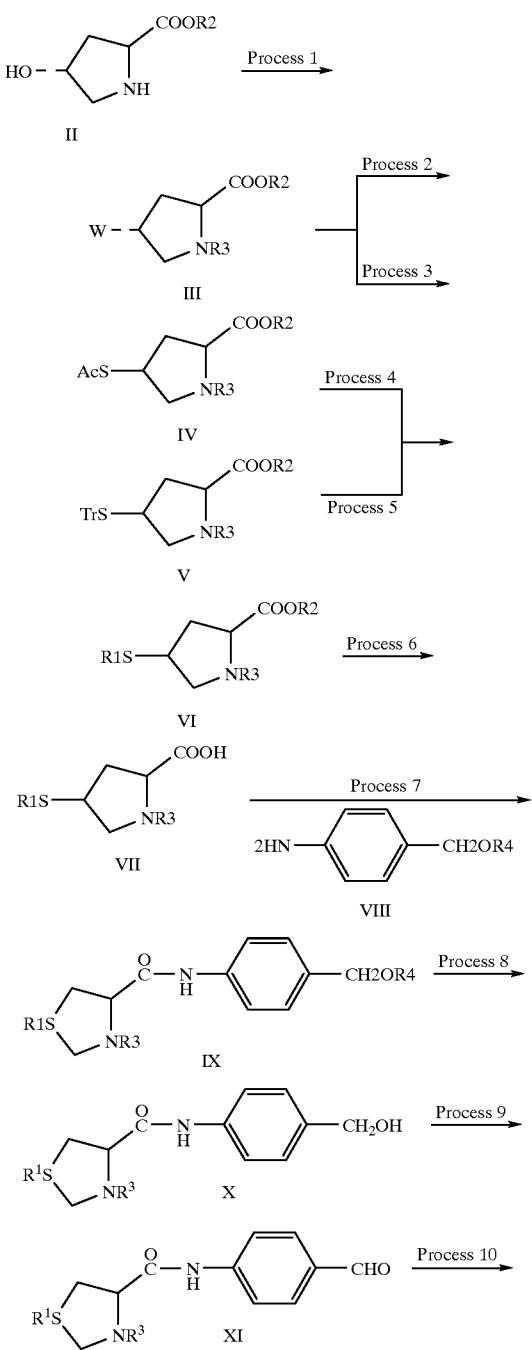

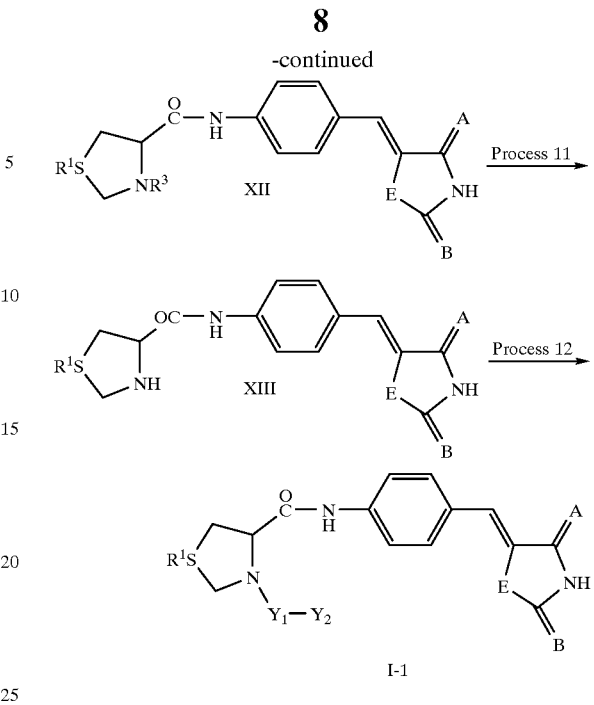

wherein $R^1$, A, B, E, $Y_1$ and $Y_2$ are as defined above and $R^2$ is lower alkyl such as methyl, ethyl, t-butyl, and the like, or aralkyl such as benzyl, or the like; Tr is trityl group; $R^3$ is N-protecting group; $R^4$ is hydroxy-protecting group; and W is a leaving group.

Process 1 (II→III)

This process involves the protection of N on pyrrolidine ring, followed by conversion of 4-hydroxyl group into a leaving group. N-protecting reaction is carried out in a solvent such as tetrahydrofuran, dichloromethane, benzene, or the like, in the presence of a base such as triethylamine, pyridine, or the like, using Boc-protecting agent such as [2-(t-butoxycarbonyloxy-imino)-2-phenylacetonitrile] (Boc-ON), t-butoxycarbonyl anhydride [$(Boc_2)O$], t-butoxycarbonylazide (Boc-$N_3$), and the like; PMZ-protecting agent such as 4-methoxybenzyloxycarbonylazide, 4-methoxybenzyl S-(4,6-dimehylpyrimidine-2-yl)thiocarbonate, 4-methoxybenzyloxycarbonyloxyimino)-2-phenylacetonitrile (MOZ-ON), and the like; or PNZ-protecting agent such as p-nitro-benzylchloroformate, and the like, so as to form carbamate.

As the next step, hydroxyl group is converted into a leaving group. Examples of leaving group include O-mesylate, O-tosylate, O-triflate, halogen, and the like. To introduce such a leaving group, the reaction is carried out according to a conventional manner using mesyl chloride, tosyl chloride, trifluoromethanesulfonyl chloride, phosphorous trichloride, phosphorous pentachloride, or the like. (Japanese Patent Publication (KOKAI) 294970/1997; U.S. Pat. No. 5317016).

Process 2 (III→IV)

This process involves the conversion of the 4-leaving group on pyrrolidine ring, which group was introduced in the Process 1 above, into sulfur-containing substituent (acetylthio). The reaction is conducted in dimethylformamide in the presence of potassium thioacetate while heating at 50–60° C.

Process 3 (III→V)

The purpose of this process is the same as that of process 2. In this process, tritylthio, instead of acetylthio, is incorporated, which is carried out by reacting with sodium tritylthio in dimethylformamide or tetrahydrofuran.

Processes 4 & 5 (IV→VI and V→VI)

In these processes, the sulfur-containing substituent is deprotected to give a sodium salt, which is then reacted with an alkyl halide (e.g., methyl iodide, 2-bromopropane), alkenyl halide (e.g., geranyl halide) or aralkyl halide (e.g., benzyl bromide) to give —S—$R^1$ derivative. In the process 4, a derivative having —S—$R^1$ at the 4-position is prepared by reacting a compound IV with sodium methylate at 0–25° C., followed by addition of a halide above.

In the process 5, a derivative having —S—$R^1$ at the 4-position is prepared by deprotecting the trityl group with silver nitrate, treating the resultant silver salt with hydrogen sulfide, converting the resultant thiol into S-sodium salt, and reacting the S-sodium salt with the halide above. To effect the reaction, silver nitrate in methanol is first added and the resulting silver salts are recovered by precipitation or extraction. The silver salt in dichloromethane or tetrahydrofuran is treated with hydrogen sulfide for 1–3 hr at a temperature range of ice-cooling to ambient temperature to give a 4-thiol, to which is added sodium methylate in a solvent such as toluene, methanol, dichloromethane, or the like. The mixture, when treated with the halide above, after concentrating to dryness to isolate S-sodium salt or as it is, gives a 4—S—$R^1$ compound.

Process 6 (VI→VII)

In this process, an ester VI is hydrolyzed with a base such as dilute sodium hydroxide, potassium hydroxide, or the like, in a solvent such as methanol, dimethyl sulfoxide, or the like.

Process 7 (VII→IX)

In this process, an amide bond is formed using a carboxylic acid VII obtained in process 6 and an amine derivative VIII by a method such as activated ester method, acid chloride method, or mixed acid anhydride method, or the like. The amine derivative VIII used in this process can be prepared by, for example, protecting hydroxyl group of p-nitrobenzyl alcohol with t-butyldimethylsilyl chloride, t-butylchlorodiphenylsilane, tetrahydropyrane, or the like, in a solvent such as tetrahydrofuran, dimethylformamide, or the like, in the presence of imidazole, and converting the nitro group into amine group through the catalytic hydrogenation using palladium or palladium on carbon in the atmosphere of hydrogen gas.

Examples of amine derivatives include 4-(t-butyldimethylsilyloxymethyl)aniline. The present process is carried out in a solvent such as tetrahydrofuran, dichloromethane, toluene, benzene, or the like. In the activated ester method, 1-hydroxybenzotriazole, hydroxysuccinimide, dimethylaminopyridine, or the like, is used in association with dicyclohexylcarbodiimide, 1-ethyl-3-(3-dimethylaminopropyl)-carbodiimide hydrochloride are used as a condensing agent. Further, in the acid chloride method, the free carboxylic acid is converted into acid chloride using an agent such as thionyl chloride or oxalyl chloride. In the mixed acid anhydride method, mixed acid anhydride is formed using ethyl chloroformate, isobutyl chloroformate, or the like. In the reaction, a base(s) such as triethylamine or pyridine can be used, if necessary.

Process 8 (IX→X)

This process involves the removal of the hydroxy-protecting group $R^4$. The deprotection is carried out using tetrabutylammonium fluoride, acetic acid, or the like, in tetrahydrofuran.

Process 9 (X→XI)

This process involves the oxidation of alcohol to aldehyde. It is carried out by Swarn oxidation, Jones' oxidation or a method using an oxidizing agent such as pyridinium chlorochromate, pyridine-$SO_3$ complex, or the like.

Process 10 (XI→XII)

This process involves the production of a benzylidene derivative XII by reacting an aldehyde XI obtained in the previous process with 2,4-thiazolidinedione, 2-thioxo-4-thiazolidinone, or 2,4-oxazolidinedione. The reaction is carried out in a solvent such as benzene, toluene, or the like, under a condition for Knoevenagel reaction using acetic acid and piperidine as a catalyst for 2 to 15 hr under refluxing temperature.

Process 11 (XII→XIII)

This process involves the deprotection of the protected N-atom of pyrrolidine ring. A salt of the corresponding acid is obtained through the reaction with, for example, 5–20 equivalents of an inorganic acid, e.g., hydrochloric acid, hydrobromic acid, for 2 to 6 hr in methanol or ethyl acetate, and the removal of the solvent in vacuo.

Process 12 (XIII→I-1)

This process involves the formation of amide, sulfonamide, urea or thiourea at the N-position of pyrrolidine ring. The formation of amide bond is carried out by reacting with acyl halide in the presence of a base such as triethylamine or pyridine, if necessary. When the acylating agent is a carboxylic acid, the reaction can be conducted in a manner similar to that descried in Process 7 above. The formation of sulfonamide is carried out by reacting substituted sulfonyl chloride derivatives in the presence of a base such as triethylamine or pyridine. The formation of urea, thiourea can be carried out using isocyanates or isothiocyanates.

< Method $B_1$ >

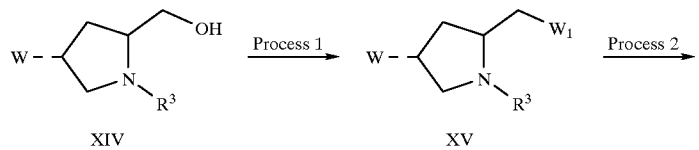

-continued
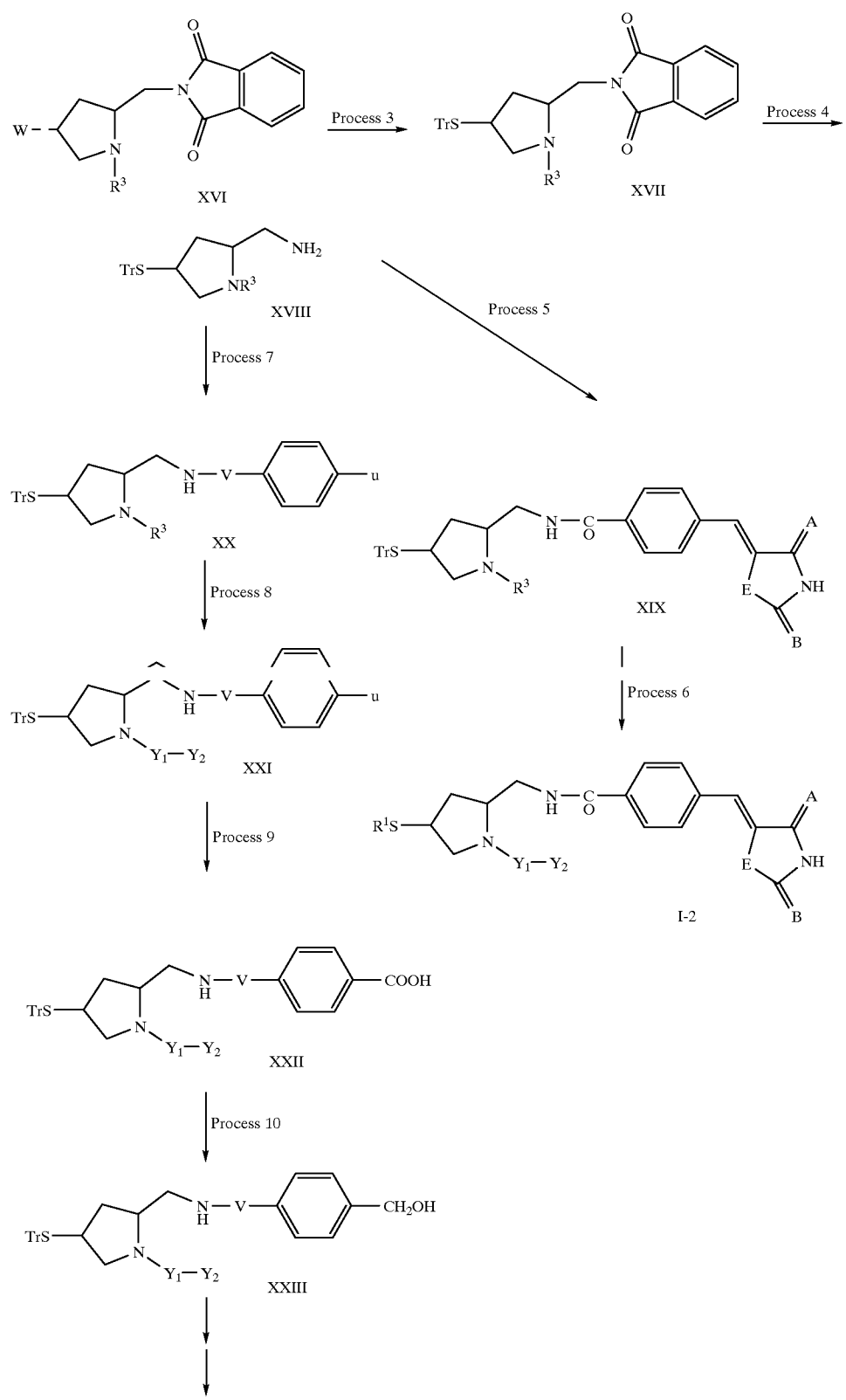

-continued

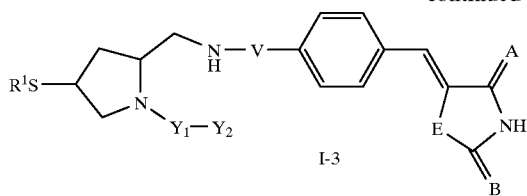

I-3 wherein $R^1$, $R^3$, A, B, E, W, $Y_1$ and $Y_2$ are as defined above and V is —$SO_2$—, —CO— or —CS—. $W_1$ is a leaving group and u is a protected carboxylic acid group.

This method is related to the synthesis of amides or sulfonamides wherein the side chain at the 2-position of pyrrolidine ring is elongated with methylene.

Process 1 (XIV→XV)

This process involves the conversion of the hydroxyl group in the 2-hydroxylmethyl group into a leaving group. This process is, for example, carried out in a manner similar to that used for the conversion of hydroxyl group into a leaving group in the Process 1 of Method A above. The starting compound can be obtained by reducing the compound obtained in process 1 of Method A.

Process 2 (XV→XVI)

This process involves the conversion of the leaving group at the 2-position into a phthalimide group. It is carried out by heating a compound XV with potassium phthalimide for 3 to 12 hr in a solvent such as dimethylformamide or tetrahydrofuran.

Process 3 (XVI→XVII)

This process involves the conversion of the leaving group at the 4-position into a tritylthio group in a manner similar to that described in Process 3 of Method A.

Process 4 (XVII→XVIII)

This process is related to the Gabriel synthesis where the phthalimide group at the 2-position is converted into an amine. The reaction is carried out by heating a starting compound XVII with hydrazine hydrate for several hours in a solvent such as methanol, dichloromethane, or the like.

Process 5 (XVIII→XIX)

This process involves the formation of an amide bond using a benzoic acid derivative having thiazolidine ring. The reaction can be carried out in a manner similar to that described in Process 12 of Method A using 4-(4-oxo-2-thioxothiazolidin-5-ylidenemethyl)benzoic acid, 4-(2,4-dioxothiazolidin-5-ylidenemethyl)benzoic acid or 4-(2,4-dioxooxazolidin-5-ylidenemethyl)benzoic acid described in JP 05306224 or can. J. Chem., 36, 1579 (1958).

Process 6 (XIX→I-2)

In this process, the substituent at the 1-position is converted into $Y_1-Y_2$ in accordance with the Processes 11 and 12 of Method A, and then the substituent at the 4-position is converted into —$SR^1$ group in accordance with the Process 5 of Method A. The order of the steps for converting the substituent at the 1- or 4-position can be reversed.

In the case of compounds I wherein $X_1$ is —$CH_2NHSO_2$— or —$CH_2NHCS$—, the aimed compound I-2 can be prepared by treating the product in Process 4 in the following manner.

Process 7 (XVIII→XX)

In this process, the product obtained in Process 4 is converted into an amide, thioamide or sulfonamide. A compound XVIII is reacted with a reactive derivative of benzoic acid, thiobenzoic acid or benzenesulfonic acid, which has the substituent u, in the presence of a base such as triethylamine or pyridine. To obtain an ureide or thioureide derivative, the compound XVIII can be reacted with an isocyanate or thiocyante. The reaction generally completes in several ten minutes to 1 hr. The substituent u stands for a protected carboxyl group, and can be an ester such as methyl ester, trimethylsilyl, and the like.

Process8 (XX→XXI)

This process can be carried out in a manner similar to those described in Processes 11 and 12 of Method A.

Process-9 (XXI→XXII)

This process is related to hydrolysis and can be carried out in a manner similar to that described in Process 6 of Method A.

Process 10 (XXII→XXIII→I-3)

In this process, the carboxylic acid moiety is first converted into a mixed acid anhydride, followed by reduction to hydroxymethyl. Thus, a mixed acid anhydride of XXII is formed using ethyl chloroformate or isobutyl chloroformate in a solvent such as tetrahydrofuran, dioxane, or the like, using a base such as triethylamine, pyridine, or the like under ice-cooling or at room temperature. The so formed mixed acid anhydride is then reduced in aqueous solution of sodium borohydride.

A compound XXIII produced in Process 10 is converted into a benzylidene in a manner similar to that described in Method A, Process 9 and processes thereafter. The product is then treated in a manner similar to that described in Process 5 of Method A to introduce —S—$R^1$ group at the 4-position to yield the aimed compound I-3. The order of step for producing benzylidene and that for or introducing —S—$R^1$ group can be reversed.

< Method $B_2$ >

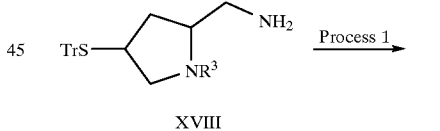

XVIII

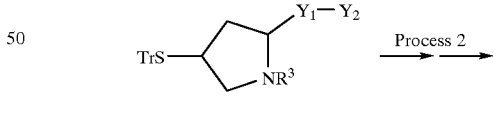

XXIV

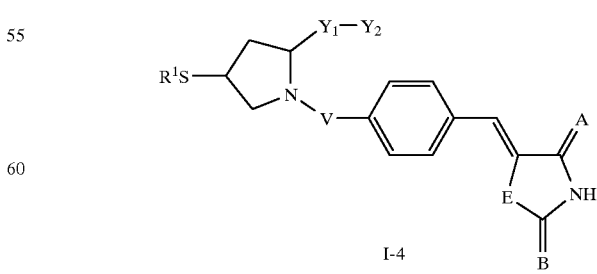

I-4 wherein $R^1$, $R^3$, A, B, E, V, $Y_1$ and $Y_2$ are as defined above. $Y_1$ is —$CH_2NHCO$— or —$CH_2NHSO_2$—.

This method is related to the synthesis of compounds having benzylidene at the 1-position of pyrrolidine ring.

Process 1 (XVIII→XXIV)

In this process, a compound XVIII prepared in Process 4 of Method $B_1$ is converted into an amide or sulfonamide in a manner similar to that of Process 12 of Method A.

Process 2 (XXIV→1-4)

This process can be effected in a manner similar to those of Process 5 of Method A and Process 8 of Method $B_1$.

< Method C >

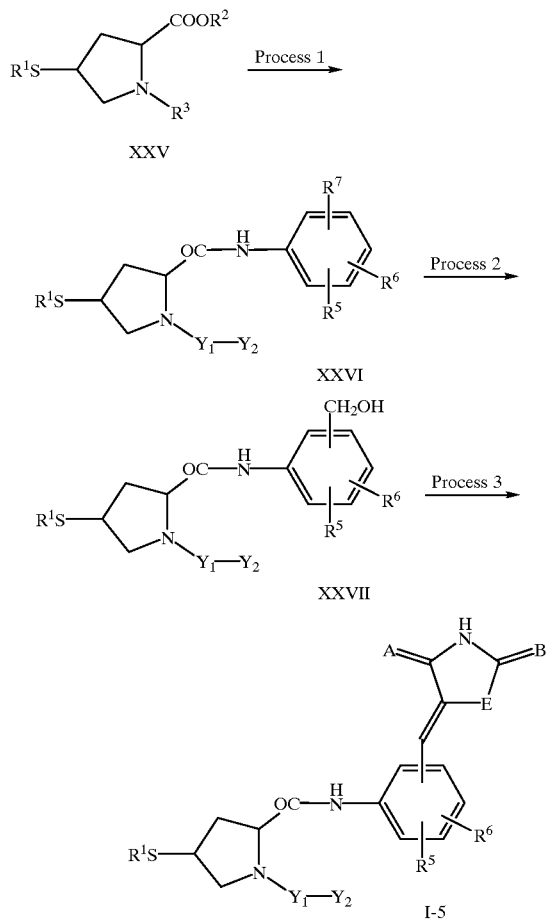

wherein $R^1$, $R^2$, $R^3$, A, B, E, $Y_1$ and $Y_2$ are as defined above, $R^7$ is t-butyldimethylsilyloxymethyl, carboxy, ester, or the like, $R^5$ and $R^6$ each are independently hydrogen, t-butyloxycarbonylamino, alkyl, alkoxy, halogen, or the like.

This method is related to the synthesis of benzylidene derivatives which are different in the binding sites, and have substituents.

Process 1 (XXV→XXVI)

This process involves the formation of an amide bond. A compound XXV is treated in a manner similar to those described in Processes 6 and 7 of Method A in this order. In addition, $R^3$ at the N-position is replaced with $Y_1$-$Y_2$ in a manner similar to those described in Processes 11 and 12 of Method A. The order of the step for amide-formation and that for $Y_1$-$Y_2$-substitution may be selected depending on the characteristics of the compound.

Process 2 (XXVI→XXVII)

This process involves the preparation of hydroxymethyl-substituted benzene derivatives. The conversion into hydroxymethyl can be carried out, when $R^7$ is t-butyl dimethylsilyloxymethyl group, in accordance with the method described in Process 8 of Method A, and, when $R^7$ is methyl ester, through the reduction with lithium hydride. In the case of other ester groups, the conversion can be carried out as described in Processes 9 and 10 of Method B.

Process 3 (XXVII→I-5)

The product of Process 2, when treated in a manner similar to that described in Method A, gives the aimed compound I-5.

< Method D >

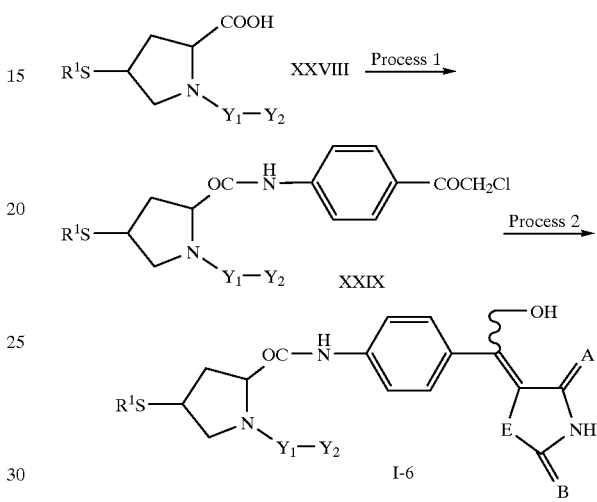

wherein $R^1$, A, B, E, $Y_1$ and $Y_2$ are as defined above.

This method is related to the synthesis of benzylidene derivatives having hydroxymethyl group on the double bond in the benzyl portion. The synthesis of p-chloroacetylaniline or formation of benzylidene can be effected in accordance with the method described in a literature such as Arie Zask et al., Tet. Lett., 34, 2719, 1993.

Process 1 (XXVIII→XXIX)

This process involves the formation of an amide bond by reacting a compound XXVIII with p-chloroacetylaniline prepared by the method described in the literature above in a manner similar to that described in Process 7 of Method A.

Process 2 (XXIX→I-6)

In this process, 2,4-thiazolidinedione is first converted into anion with n-butyllithium in tetrahydrofuran, and then allowed to react with chloroacetyl compound.

<Method $E_1$>

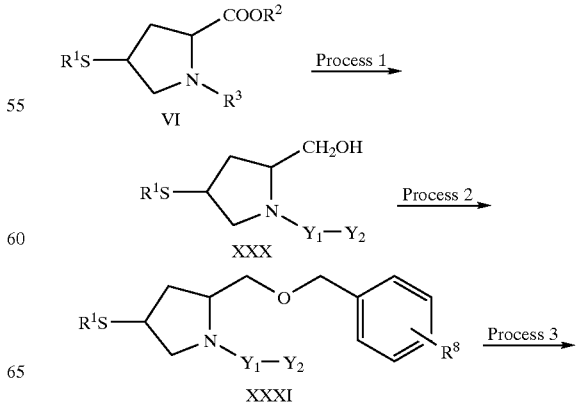

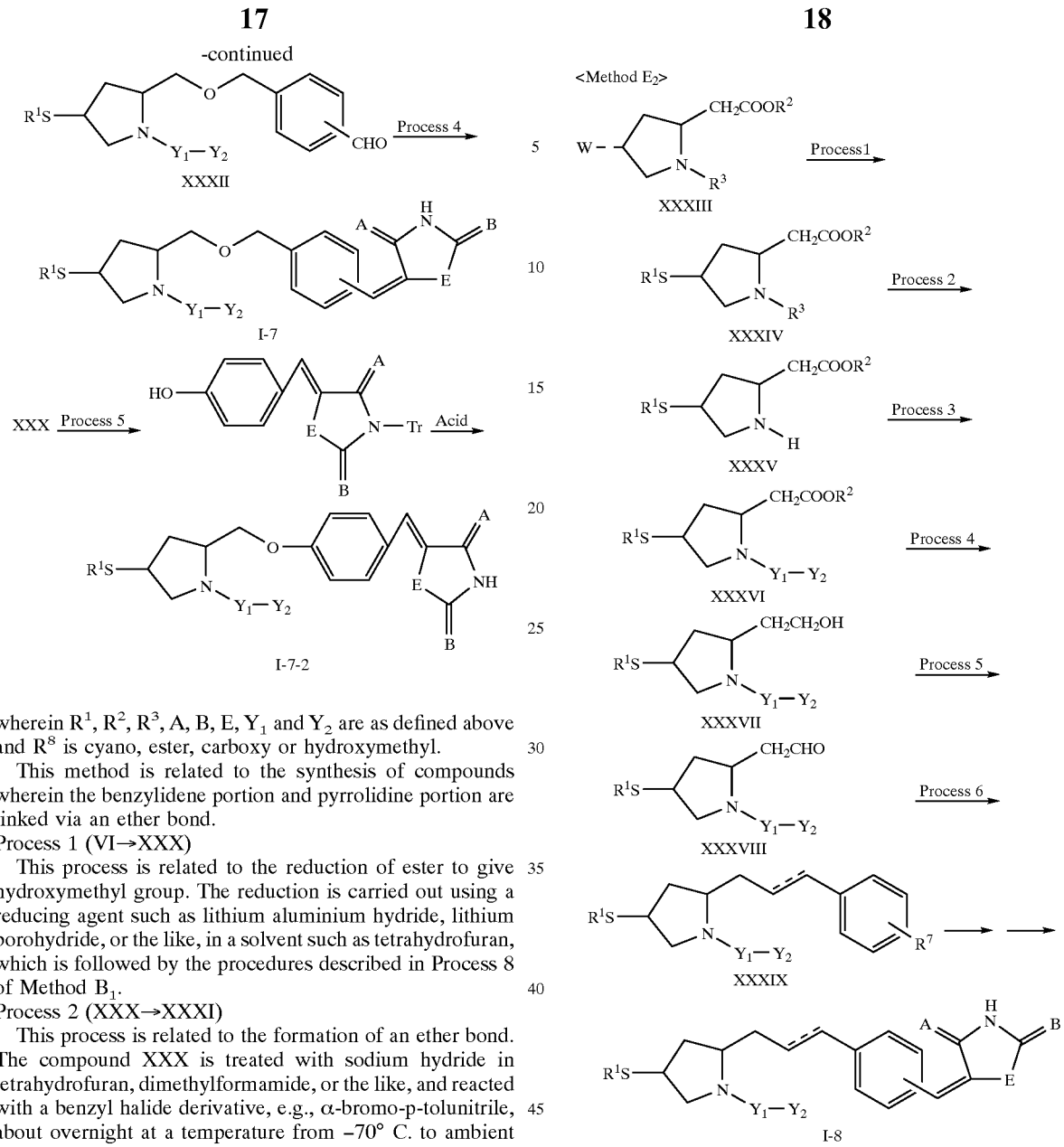

wherein $R^1$, $R^2$, $R^3$, A, B, E, $Y_1$ and $Y_2$ are as defined above and $R^8$ is cyano, ester, carboxy or hydroxymethyl.

This method is related to the synthesis of compounds wherein the benzylidene portion and pyrrolidine portion are linked via an ether bond.

Process 1 (VI→XXX)

This process is related to the reduction of ester to give hydroxymethyl group. The reduction is carried out using a reducing agent such as lithium aluminium hydride, lithium borohydride, or the like, in a solvent such as tetrahydrofuran, which is followed by the procedures described in Process 8 of Method $B_1$.

Process 2 (XXX→XXXI)

This process is related to the formation of an ether bond. The compound XXX is treated with sodium hydride in tetrahydrofuran, dimethylformamide, or the like, and reacted with a benzyl halide derivative, e.g., α-bromo-p-tolunitrile, about overnight at a temperature from −70° C. to ambient temperature to give the compound XXXI.

Process 3 (XXXI→XXXII)

In this process, the substituent $R^8$ on benzene ring is converted into aldehyde trough hydrolysis, esterification, reduction, oxidation, or the like. For example, when $R^8$ is cyano, it is carried out by reacting a starting compound XXXI with diisobutylalminium hydride in a solvent such as benzene, toluene, or the like, about overnight at a temperature from 0° C. to ambient temperature optionally under heating at about 50° C.

Process 4 (XXXII→I-7)

This process is related to the formation of benzylidene bond through the Aldol condensation in a manner similar to that described in Process 10 of Method A. The product, when treated conventionally, gives the aimed compound I-7.

Process 5 (XXX→I-7-2)

In this process, the compound I-7-2 is prepared by subjecting a starting compound XXX to Mitsunobu reaction to form phenyl ether bond, and deprotecting the trityl group on nitrogen atom on thiazolidine or oxazolidine ring by treatment with acid such as trifluroroacetic acid, or the like.

wherein $R^1$, $R^2$, $R^3$, $R^7$, A, B, E, W, $Y_1$ and $Y_2$ are as defined above.

This method is related to the synthesis of compounds wherein the pyrrolidine and benzylidene portions are linked via carbon—carbon bond including double bond.

Processes 1–5 (XXXIII→XXXVIII)

The starting compound XXXIII is prepared following the teaching of M. Sunagawa et al., Journal of Antibiotics, 44(4), 459 (1991). Processes 1–5 leading to an aldehyde can be effected in manners similar to those described in Method A.

Process 6 (XXXVIII→I-8)

In this process, the formation of benzylidene and the catalytic hydrogenation are carried out simultaneously or optionally in series to give a saturated bond(s). For example, when $R^7$ is an ester, a starting compound XXXVIII is first heated to reflux with, for example, methyl 4-(bromotriphenylphosphonium-methyl)benzoate, in a solvent such as ethanol or methanol in the presence of a base such as triethylamine for about 14 hr to yield the aimed benzylidene compound (I-8). The catalytic hydrogenation of a double bond(s) is carried out in a solvent such as methanol or ethyl acetate using platinum as a catalyst in an atmosphere of hydrogen. The resultant product, when treated in the same manner as that described in Method $E_1$, gives the aimed compound.

<Method F> (VI → I-9)

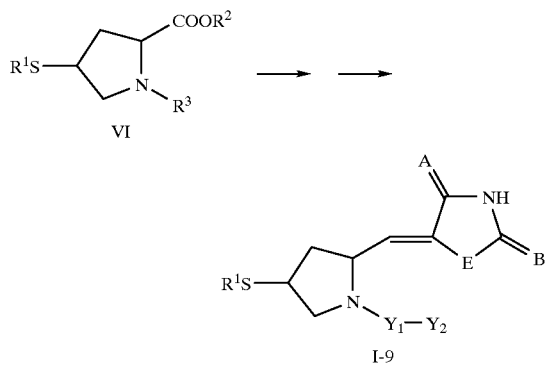

wherein $R^1$, $R^2$, $R^3$, A, B, E, $Y_1$ and $Y_2$ are as defined above.

This method is related to the synthesis of compounds having thiazolidine or oxazolidine ring linked to pyrrolidine ring at the 2-position via methylidene. The conversion of respective substituent can be carried out in manners similar to those described in Method A.

<Method G> (XL → XLI → I-10)

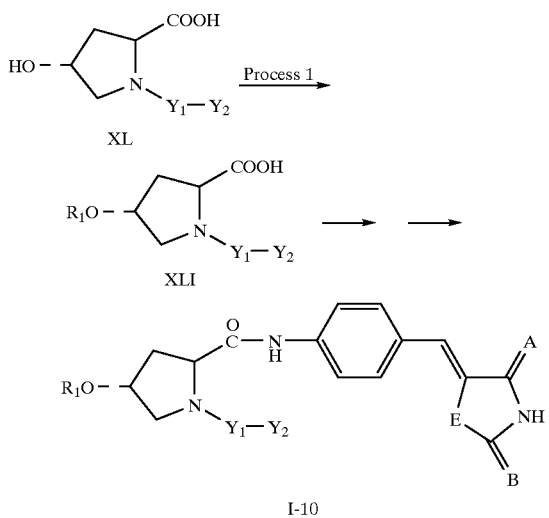

wherein $R^1$, $R^3$, A, B, E, $Y_1$ and $Y_2$ are as defined above.

This method is related to the synthesis of compounds having oxygen atom at the 4-posion of pyrrolidine ring.

Process 1

This process is related to the formation of an ether bond in a 4-hydroxy compound derived from the starting compound used in the Method A. To the 4-hydroxy compound is added a strong base such as sodium hydride in a solvent, e.g., dimethylformamide, in the presence of alkyl halide. The reaction completes in 3 to 15 hours at a temperature range of 0° C. to ambient temperature.

The rest of the processes following the Process 1 above, involving the conversion of respective substituent, can be carried out in manners similar to those described in Method A.

<Method H>

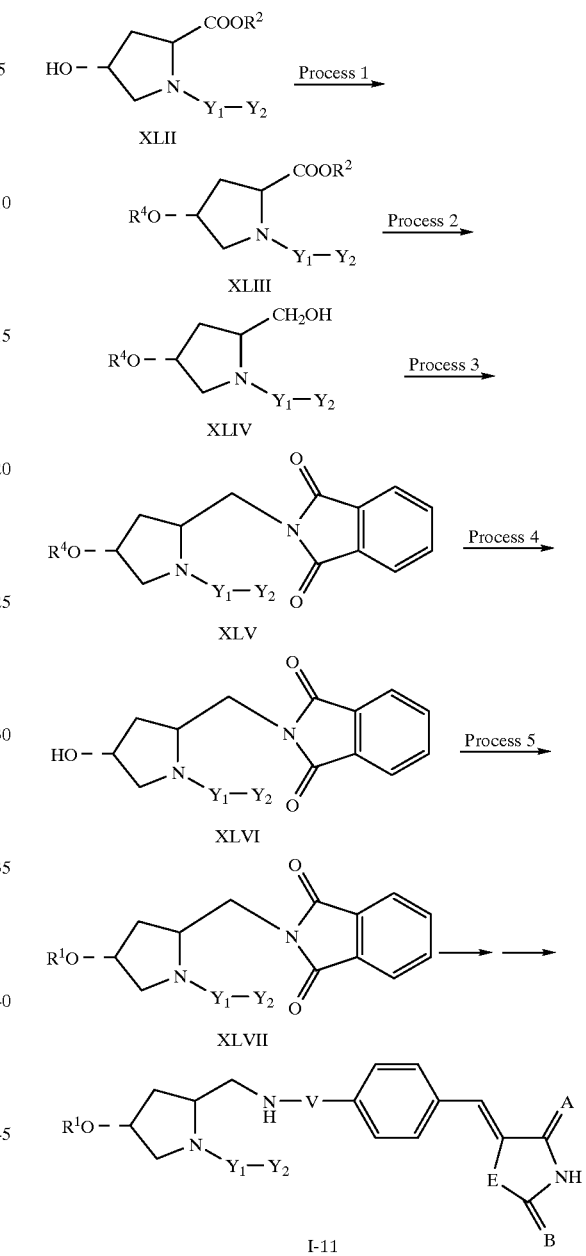

wherein $R^1$, $R^2$, $R^4$, A, B, E, V, $Y_1$ and $Y_2$ are as defined above.

This method is related to the synthesis of compounds having oxygen atom linked at the 4-posion of pyrrolidine ring and an amide formed by elongating the 2-side chain with methylene.

Process 1 (XLII→XLIII)

This process is related to the protection of hydroxyl group. For example, derivatives having a tetrahydropyranyl-protected hydroxyl group can be prepared through the treatment with 3,4-dihydro-2H-pyrane in dichloromethane in the presence of p-toluenesulfonic acid as a catalyst.

Process 2 (XLIII→XLIV)

This process is the same as Process 1 of Method $E_1$, which is related to the conversion of ester into hydroxyl group.

Process 3 (XLIV→XLV)

This process is related to the conversion of hydroxyl group into phthalimide group by means of Mitsunobu reaction. For example, after reacting triphenylphosphine and diisopropyl azodicarboxylate or diethyl azodicarboxylate in tetrahydrofuran at low temperature, phthalimide and a compound XLIV are added in series thereto and the mixture is reacted for several hours at a temperature range of ice-cooling to ambient temperature for about overnight.

Process 4 (XLV→XLVI)

This process is related to the deprotection of protected hydroxyl group through the reaction with p-toluenesulfonic acid or aqueous acetic acid in a solvent such as methanol, tetrahydrofuran, or the like, at room temperature about overnight.

Process 5 (XLVI→I-11)

This process is the same as the Process 1 of Method G and is related to the formation of an ether bond.

The resultant compound is then treated in manners similar to those described in Processes 4 and 5 of Method B to give the aimed compound.

<Method I>

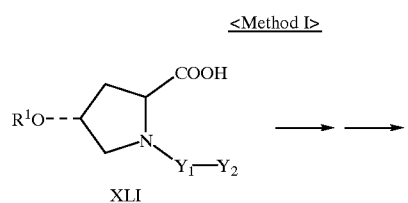

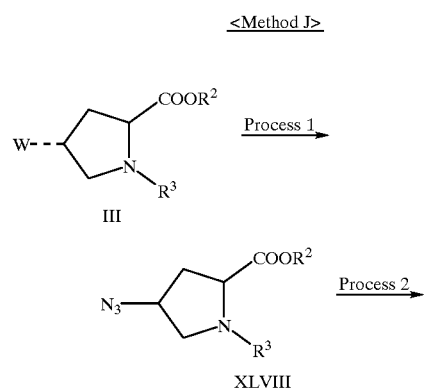

wherein $R^1$, A, B, E, $Y_1$ and $Y_2$ are as defined above.

This method is related to the synthesis of compounds having an oxygen atom at the 4-position of pyrrolidine ring and hydroxymethyl group on the double bond in the benzyl portion. This method can be effected in a manner similar to that described in Method D using a carboxylic acid obtained in Method G as a starting compound.

<Method J>

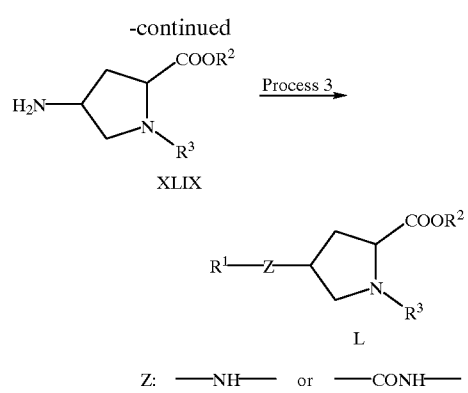

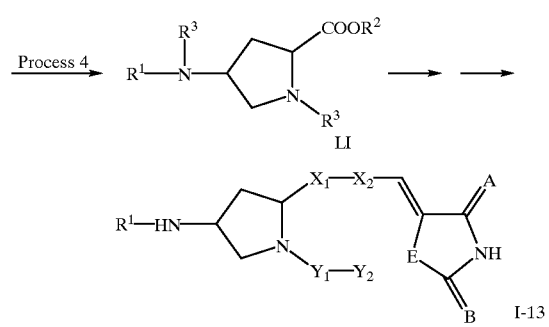

wherein $R^1$, $R^3$, $R^3$, $X_1$, $X_2$, A, B, E, W, $Y_1$ and $Y_2$ are as defined above.

This method is related to the synthesis of compounds having a nitrogen atom at the 4-posion of pyrrolidine ring.

Process 1 (III→XLVIII)

In this process, a nitrogen atom is introduced at the 4-position through the reaction with sodium azide in a solvent such as dimethylformamide at 40 to 60° C. for about 2 to 9 hr.

Process 2 (XLVIII→XLIX)

In this process, an azide group is reduced to amine through the catalytic hydrogenation with platinum in a solvent such as dioxane in the atmosphere of hydrogen gas.

Process 3 (XLIX→L)

This process is related to the alkylation, which is carried out through the reaction with an alkyl halide in the presence of a base such as potassium carbonate or sodium hydroxide in acetonitrile for about 16 hr at a temperature of ice-cooling to room temperature.

Process 4 (L→I-13)

This process is related to the protection of an amine when Z is NH. When Z is —CONH—, the objective compound I-13 can be prepared directly from a compound L without obtaining an intermediate LI. This process can be carried out by the method described in the Process 1 of Method A.

The resultant compound, when treated in manners similar to those described above, gives the aimed compound.

<Method K> (LII ⟶ I-14)

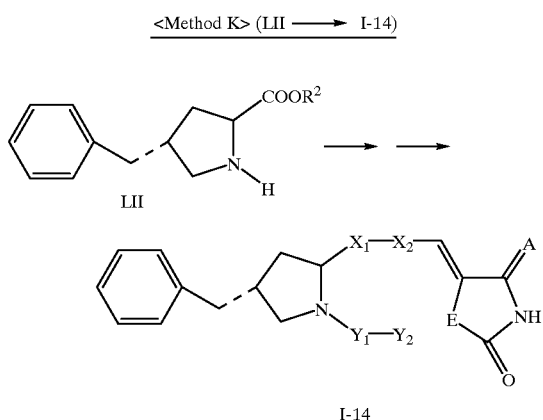

LII

I-14 wherein $R^2$, A, B, E, $X_1$, $X_2$, $Y_1$ and $Y_2$ are as defined above.

This method is related to the synthesis of compounds having substituent on the carbon atom at the 4-position. Pyrrolidines having a carbon atom at the 4-position can be synthesized in accordance with the method described in a literature (J. Org. Chem., 57, 1927, 1992). The conversion at the 1- and 2-positions can be carried out in a conventional manner.

<Method L> (LIII ⟶ I-15)

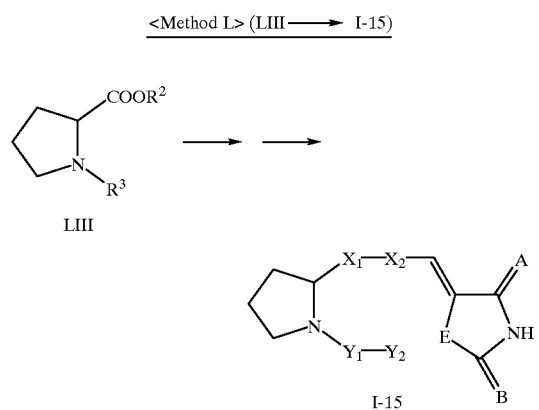

LIII

I-15 wherein $R^2$, $R^3$, A, B, E, $X_1$, $X_2$, $Y_1$ and $Y_2$ are as defined above.

This method is related to the synthesis of compounds having no substituent at the 4-position. The aimed compounds can be prepared in a manner similar to that described above except that proline is used as a starting compound.

<Method M> (LIV ⟶ I-16)

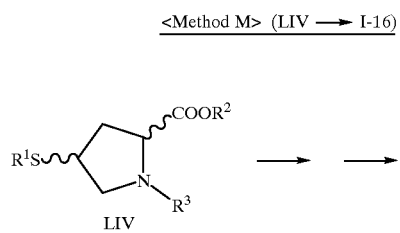

LIV

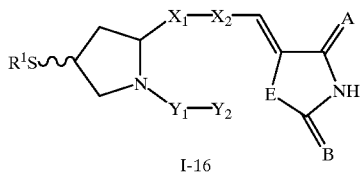

I-16 wherein $R^1$, $R^2$, $R^3$, A, B, E, $X_1$, $X_2$, $Y_1$ and $Y_2$ are as defined above.

This method is related to the synthesis of compounds which correspond to those described in Methods A and $B_1$, but are in different configuration(s) at the 2- and/or 4-position. Compounds having sulfur atom at the 4-position obtained in the above are in (2β, 4β) configuration though, those prepared by Method M are in (2β, 4α), (2α,4β), or (2α,4α) configuration.

All the starting compounds are known in Japanese Patent Publication (KOKAI) No. 294970/1993 (U.S. Pat. No. 5317016). The conversion of respective functional group can be carried out in a manner similar to that described above. Compounds having substituents in other positions are obtainable according to reactions similar to those mentioned above. When a compound contains a functional group(s) possibly interfering the reaction, it can be protected and deprotected at an appropriate stage.

The present invention is not restricted to any particular isomers but includes all possible isomers and racemic modifications.

The compound I of the present invention has an activity of inhibiting the production of prostaglandin $E_2$ through the inhibition of $cPLA_2$ activity and is expected to be useful in the prevention or treatment of diseases attributable to prostaglandin or leukotriene.

When using a compound I of the present invention in the treatment, it can be formulated into ordinary formulations for oral or parenteral administration such as intravenous injection and percutaneous administration. That is, the compound of the present invention can be formulated in the form for oral administration such as tablets, capsules, granules, powders, syrup, and the like; or parenteral administration such as injectable solution or suspension for intravenous, intramuscular or subcutaneous injection, suppositories, or percutaneous formulations such as ointment.

The formulations above can be prepared using appropriate carriers, excipients, solvents, and bases known to one of ordinary skill in the art. For example, tablets can be prepared by compressing or fomulating an active ingredient together with auxiliary components. Examples of usable auxiliary components include pharmaceutically acceptable excipients such as binders (e.g., cornstarch), fillers (e.g., lactose, microcrystalline cellulose), disintegrants (e.g., sodium glycolate starch) or lubricants (e.g., magnesium stearate). Tablets may be coated appropriately. In the case of liquid formulations such as syrups, solutions, or suspensions, they may contain suspending agents (e.g., methyl cellulose), emulsifiers (e.g., lecithin), preservatives, and the like. In the case of injectable formulations, it may be in the form of solution or suspension, or oily or aqueous emulsion, which may contain suspension-stabilizing agent or dispensing agent, and the like.

An appropriate dosage of the compound I varies depending on the administration route, age, body weight, sex, or conditions of the patient, the kind of drug(s) used together, if any, and should be determined by a physician in the end. However, in the case of oral administration, the daily dosage can generally be between about 10–100 mg/kg body weight. In the case of parenteral administration, the daily dosage can generally be between about 0.1–10 mg, preferably about 1–5 mg. The daily dosage can be administered in one to several divisions.

The following Examples are provided to further illustrate the present invention and are not to be construed as limiting the scope thereof.

EXAMPLE 1 (Method A)

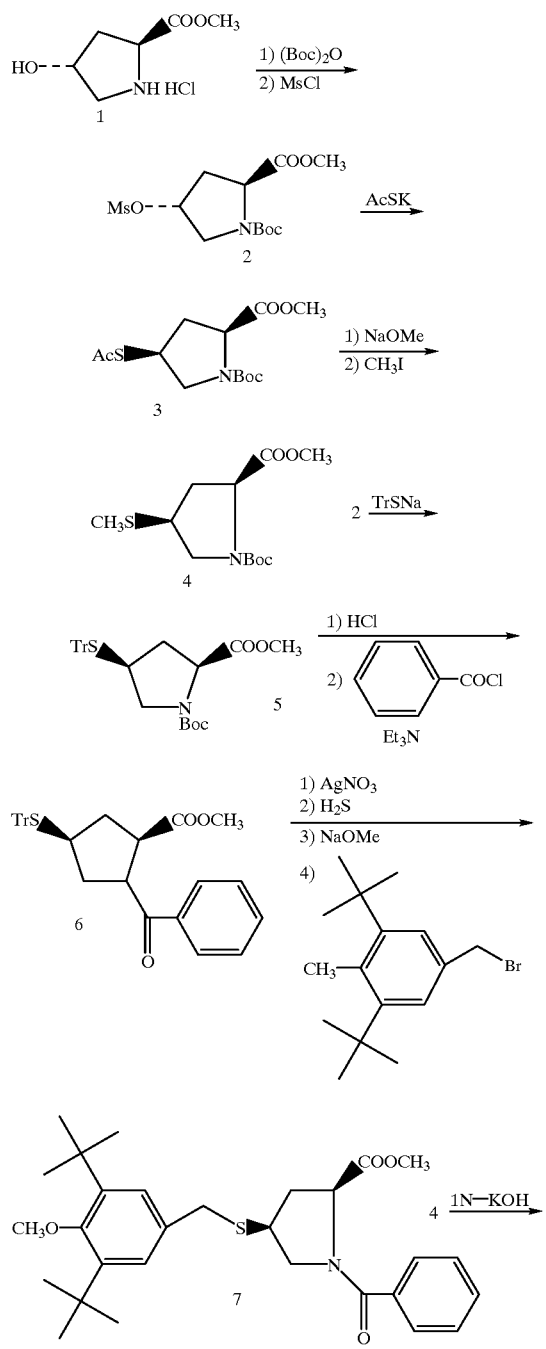

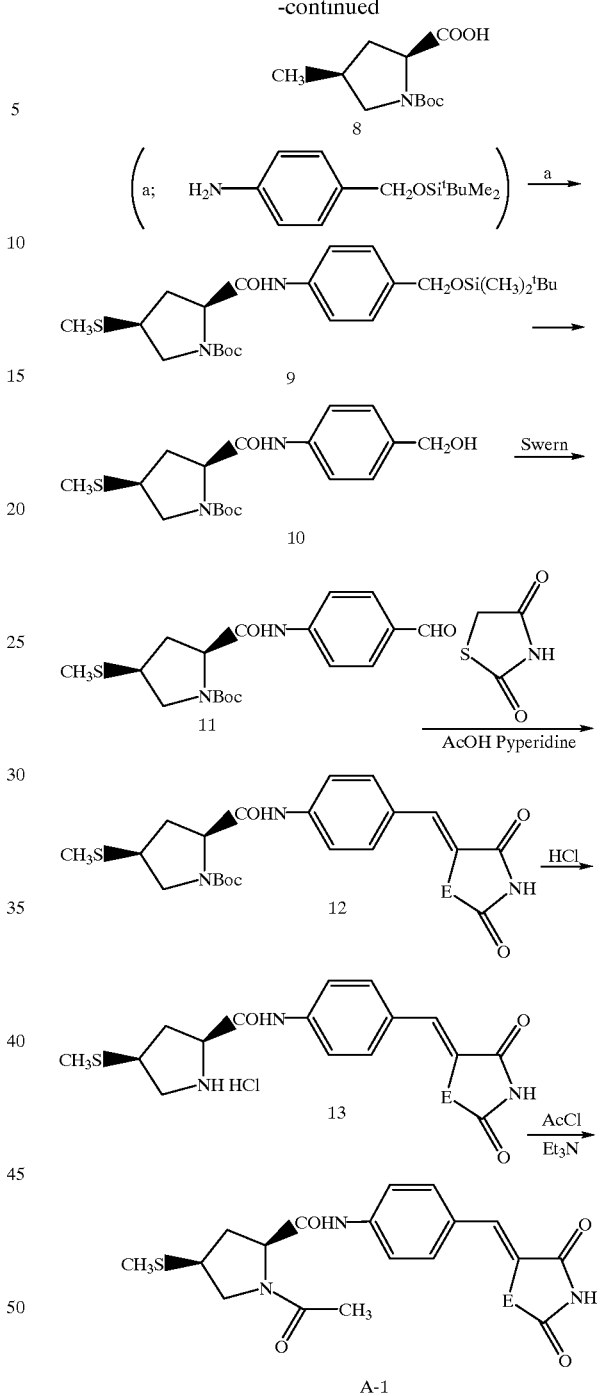

(1) 1→2

To a solution of 4-hydroxy-L-proline methyl ester hydrochloride (45.4 g, 250 mol) in methylene chloride (450 ml) were added triethylamine (70 ml, 2×250 mmol), and then di-t-butyl dicarbonate (69 ml, 1.2×250 mmol) under ice cooling. After stirring for 2 hr at room temperature, the reaction solution was washed with 2N HCl, 5% NaHCO$_3$, H$_2$O successively, dried over Na$_2$SO$_4$ and concentrated in vacuo to obtain an aimed product (72.6 g) as an oil.

The product was dissolved in methylene chloride (300 ml). To the solution were added triethylamine (38.3 ml, 1.1×250 mmol) and methanesulfonyl chloride (19.4 ml, 250 mmol) under ice-cooling, and the mixture stirred for 30 min at the same temperature. The reaction solution was washed with 2N-HCl, 5% NaHCO$_3$ and H$_2$O, successively, dried over Na$_2$SO$_4$, concentrated in vacuo and recrystallized from ethyl ether/hexane to obtain mesylate (69.5 g). Yield 86%.

(2) 2→3

To a solution of mesylate (5.0 g, 15.46 mmol) in dimethylformamide (15 ml) was added potassium thioacetate (2.12 g, 1.2×15.46 mmol) and heated at 60° C. for 90 min. After pouring into water, the mixture was extracted with ethyl acetate. The extract was washed with H$_2$O, dried over Na$_2$SO$_4$, and concentrated in vacuo. The residue was subjected to silica gel column chromatography and the fractions eluting with hexane/ethyl acetate (3:1) were collected to yield acetate (3.18 g) as an oil. Yield 67.8%.

Elemental analysis (C$_{13}$H$_{21}$NO$_5$S) Calcd.: C, 51.47; H, 6.98; N, 4.62; S, 10.57 Found: C, 51.24; H, 6.95; N, 4.64; S, 10.54. IR (CHCl$_3$): 1752,1695.

(3) 3→4

To a solution of thioacetate (22.38 g, 73.7 mmol) in toluene (74 ml) was added 1M-NaOMe/MeOH (74 ml, 73.7 mmol) over 8 min at −25° C. After standing for 5 min at the same temperature, iodomethane (9. 2 ml, 2×73.7 mmol) was added thereto and the mixture stirred for another 1 hr at room temperature. The reaction mixture was poured into water and extracted with ethyl acetate. The extract was washed with 2N HCl, 5% NaHCO$_3$ and H$_2$O, successively, dried over Na$_2$SO$_4$, and concentrated in vacuo. The residue was subjected to silica gel column chromatography and the fractions eluting with hexane/ethyl acetate (3:1) were collected to yield methylthio compound (20.3 g) as an oil. Yield 100%.

Elemental analysis (C$_{12}$H$_{21}$NO$_4$S) Calcd.: C, 52.34; H, 7.69; N, 5.09; S, 11.64 Found: C, 52.14; H, 7.61; N, 5.11; S, 11.57. IR (CHCl$_3$): 1752,1695.

(4) 2→5

To a suspension of 60% sodium hydride (2.9 g, 1.3×55.67 mmol) in tetrahydrofuran (50 ml) was added a solution of triphenylmethylmercaptane (21.5 g, 1.4×55.67 mmol) in tetrahydrofuran (10 ml) over 15 min in an atmosphere of argon under ice-cooling. The mixture was stirred for 10 min at the same temperature.

A solution of a starting compound (18 g, 55.67 mmol) in tetrahydrofuran (60 ml) was stirred in an atmosphere of argon under ice-cooling. To the solution was added the previously prepared solution and the mixture stirred for 24 hr at room temperature. The reaction solution was poured into water and extracted with ethyl acetate. The extract was washed with water and concentrated in vacuo. The residue was subjected to silica gel column chromatography. The fractions eluting with hexane/ethyl acetate (4:1 to 1:1) were collected and recrystallized from dichloromethane/hexane to obtain the objective compound (22.4 g). mp. 163–164° C., yield 80%.

Elemental analysis (C$_{30}$H$_{33}$NO$_4$S) Calcd.: C, 71.54; H, 6.60; N, 2.78; S, 6.37 Found: C, 71.58; H, 6.66; N, 2.83; S, 6.30. IR (CHCl$_3$): 1749,1690,1596,1489,1446. NMR (CDCl$_3$): 1.34 (s, 9/2H), 1.39 (s, 9/2H), 1.66 (m, 1H), 1.85 (m, 1/2H), 2.20 (m, 1/2H), 2.66–2.95 (m, 2H), 3.17 (m, 1/2H), 3.47 (m, 1/2H), 3.68 (s, 3/2H), 3.70 (s, 3/2H), 3.98 (m, 1H), 7.18–7.50 (m, 15H).

(5) 5→6

Hydrogen chloride gas (31 g, 17 equivalent) was bubbled into a solution containing a starting compound (25.5 g, 50.6 mmol) in a mixture of dried methanol (300 ml) and dried dichloromethane (150 ml) under ice-cooling. After stirring for 2 hr at room temperature, the mixture was concentrated in vacuo. The residue was flushed with toluene (×2) to obtain hydrochloride, which was dissolved in dichloromethane (150 ml). To the solution were added triethylamine (21.3 ml, 3×50.6 mmol) and then benzoyl chloride (6.5 ml, 1.1×50.6 mmol) under ice-cooling and a nitrogen atmosphere. After stirring for 1 hr at room temperature, the reaction solution was washed with 2N-HCl, 5% NaHCO$_3$ and H$_2$O, successively, dried over Na$_2$SO$_4$, and concentrated in vacuo. The residue was subjected to silica gel column chromatography and the fractions eluting with hexane/ethyl acetate (2:1) were collected to yield the objective product as a foam quantitatively. NMR (CDCl$_3$): 1.85 (m, 1H), 2.28 (m, 1H), 2.52 (m, 1H), 2.75 (m, 1H), 3.03 (t, J=10.8 Hz, 1H), 3.74 (s, 3H), 4.47 (d. d, J=10.0,7.8 Hz, 1H), 7.00–7.52 (m, 20H).

(6) 6→7

To a solution of a starting compound (26 g, 51.2 mmol) in methanol (300 ml) was added pyridine (10.4 ml, 5×51.2 mmol) under ice-cooling. Silver nitrate (20 g, 2.3×51.2 mmol) in a mixture of methanol (40 ml) and water (40 ml) was then added to the solution over 10 min, followed by stirring for another 10 min. After addition of water, the reaction mixture was extracted with dichloromethane (500 ml). The extract was washed with water, and dried over Na$_2$SO$_4$ to obtain a solution of silver salt in dichloromethane, which was used in the next step as it is.

Hydrogen sulfide was bubbled into the solution with stirring and under ice-cooling over 10 min. The precipitated silver sulfide was filtered off and the filtrate was concentrated in vacuo. The residue was subjected to silica gel column chromatography and the fractions eluting with hexane/ethyl acetate (2:1) were collected to yield the thiol compound (13.13 g) as a gum.

NMR (CDCl$_3$): 1.74 (d, J=7.5 Hz, 1H), 1.97 (m, 1H), 2.83 (m, 1H),3.25 (m, 1H), 3.57 (t, J=10.0 Hz, 1H), 3.79 (s, 3H), 3.90 (m, 1H), 4.72 (d. d, J=9.2,8.0 Hz, 1H), 7.34–7.62 (m, 5H).

A solution of the resultant thiol compound (13.13 g, 49.5 mmol) in dimethylformamide (130 ml) was stirred under cooling at −50° C. under argon. To the mixture was added 2.55M/L sodium methylate/methanol solution (18.4 ml, 0.95×49.5 mmol) over 1 min. Three-minute later, a solution of 3,5-di-t-butyl-4-methoxybenzyl bromide (19.6 g, 1.2× 49.5 mmol) in dimethylformamide (20 ml) was added over 7min. The mixture was stirred for another 20 min, poured into water and extracted with dichloromethane. The extract was washed with water, dried over Na$_2$SO$_4$, and concentrated in vacuo. The residue was subjected to silica gel column chromatography and the fractions eluting with hexane/ethyl acetate (2:1) were collected to yield an aimed product (12.97 g) as a gum. Yield, 51%. A portion was lyophilized from benzene and subjected to elemental analysis.

Elemental analysis (C$_{29}$H$_{39}$NO$_4$S 0.4C$_6$H$_6$) Calcd.: C, 71.30; H, 7.88; N, 2.65; S, 6.06 Found: C, 71.22; H, 7.92; N, 2.77; S, 5.81. IR (CHCl$_3$): 1749,1632,1603,1578,1413. NMR (CDCl$_3$): 1.35 (s, 18H), 1.93 (m, 1H), 2.60 (m, 1H), 3.08 (m, 1H), 3.50 (m, 1H), 3.59 (s, 3H), 3.66 (s, 2H), 3.76 (s, 3H), 4.65 (d.d, J=7.8,9.4 Hz, 1H), 7.09 (s, 2H), 7.32–7.58 (m, 5H).

(7) 7→8

To a solution of methyl ester (20.3 g, 73.7 mmol) in methanol (148 ml) was added 1N KOH 148 ml (2×73.7 mmol) and the mixture stirred for 3 hr at room temperature. The reaction mixture was poured into water, acidified with 2N HCl, and extracted with ethyl acetate. The extract was washed with brine, dried over Na$_2$SO$_4$, and concentrated in vacuo. The residue was recrystallized from ethyl ether/ hexane to obtain carboxylic acid (18.68 g). mp. 88–89° C., yield 96.9%.

Elemental analysis ($C_{11}H_{19}NO_4S$) Calcd.: C, 50.56; H, 7.33; N, 5.36; S, 12.27 Found: C, 50.34; H, 7.28; N, 5.40; S, 12.17. IR ($CHCl_3$)::1758,1725 1695.

(8) 8→9

To a solution of carboxylic acid (18.55 g, 70.98 mmol) in methylene chloride (190 ml) were added triethylamine (23.7 ml, 2.4×70.98mmol) and then ethyl chlorocarbonate (8.1 ml, 1.2×70.98 mmol) under ice-cooling, and the mixture stirred for 30 min at the same temperature. After the addition of a solution of 4-(dimethyl-t-butylsilyloxymethyl)aniline (20.22 g, 1.2×70.98 mmol) in dimethylformamide (20 ml), the mixture was stirred for 1 hr at the same temperature. The reaction mixture was washed with 2N HCl, 5% $NaHCO_3$ and $H_2O$ successively, dried over $Na_2SO_4$, and concentrated in vacuo. The residue was subjected to silica gel column chromatography and fractions eluting with hexane/ethyl acetate (4:1 to 2:1) were collected to obtain a silyl ether (33.57 g) as a foam. Yield 98.4%.

(9) 9→10

To a solution of the silyl ether (33.57 g, 69.8 mmol) in tetrahydrofuran (340 ml) was added 1N tetra-n-butylammonium fluoride (77 ml, 1.1×69.8 mmol) under ice-cooling and the mixture stirred for 5 hr at room temperature. The reaction mixture was poured into water and extracted with ethyl acetate. The extract was washed with 2N HCl, 5% $NaHCO_3$ and $H_2O$ successively, dried over $Na_2SO_4$ and concentrated in vacuo. The residue was subjected to silica gel column chromatography and fractions eluting from hexane/ethyl acetate/methylene chloride (1:1:0.5) to ethyl acetate were collected. Recrystallization from methylene chloride/n-hexane gives an alcohol (24.21 g). MP. 164.6–165° C., yield 94.6%.

Elemental analysis ($C_{18}H_{26}N_2O_4S$) Calcd.: C, 58.99; H, 7.15; N, 7.64; S, 8.75 Found: C, 59.17; H, 7.26; N, 7.53; S, 8.50. IR ($CHCl_3$): 3610,3410,3330,1690,1602,1523.

(10) 10→11

A solution of oxalyl chloride (3.7 ml, 1.5×27.29 mmol) in methylene chloride (100 ml) was stirred at =78° C. To the solution was added dropwise a solution of dimethyl sulfoxide (5.8 ml, 3×27.29 mmol) in methylene chloride (58 ml) over 10 min. The mixture was stirred for anther 15 min and a solution of the alcohol (10.0 g, 27.29 mmol) in methylene chloride (100 ml) was added over 5 min. After stirring for 30 min at the same temperature, triethylamine (19 ml, 5×27.29 mmol) was added. The reaction solution was warmed to room temperature over 30 min, washed with 2N HCl, 5% $NaHCO_3$ and $H_2O$ successively, dried over $Na_2SO_4$ and concentrated in vacuo. The residue was subjected to silica gel column chromatography and fractions eluting with hexane/ethyl acetate (1;1)to obtain an aldehyde (9.35g) as a foam. Yield94.0%.

Elemental analysis ($C_{18}H_{24}N_2O_4S$ $0.2H_2O$) Calcd: C, 58.74; H, 6.68; N, 7.61; S, 8.71 Found: C, 58.62; H, 6.66; N, 7.49; S, 8.82. IR ($CHCl_3$): 3400,1695,1592. NMR ($CDCl_3$): 1.48 (S, 9H), 2.15 (s, 3H), 7.70 (d, J=8.6 Hz, 2H), 7.85 (d, J=8.6 Hz, 2H), 9.91 (s, 1H).

(11) 11→12

To a solution of the aldehyde (6.3 g, 17.29 mol) in dry toluene (63 ml) were added 2,4-thiazolizinedione (2.02 g, 17.29 mmol), 1M piperidine/toluene (0.86 ml, 0.05×17.29 mmol) and 1M acetic acid/toluene (0.86 ml, 0.05×17.29 mmol). The mixture was heated to reflux for 2 hr with stirring and dehydrating with molecular sieves. After the reaction mixture was cooled, methyl ethyl ketone was added thereto. The mixture was washed with 2N HCl and then $H_2O$, dried over $Na_2SO_4$ and concentrated in vacuo. The residue was subjected to silica gel column chromatography and fractions eluting with methylene chloride/methanol (10:1) were collected and recrystallized from methylene chloride/ethyl ether to obtain an aimed product (7.42 g). mp. 216–217° C. (decomp.), yield 92.5%.

Elemental analysis ($C_{21}H_{25}N_3O_5S_2$) Calcd.: C, 54.41; H, 5.44; N, 9.06; S, 13.83 Found: C, 54.23; H, 5.53; N, 8.91; S, 13.60. IR (Nujol):3250,1742,1710,1692,1670,1600,1535. NMR ($CDCl_3$):1.49 (s, 9H), 2.16 (s, 3H).

(12) 12→13

To a suspension of a starting compound (3.0 g, 6.47 mmol) in methanol (30 ml) and methylene chloride (12 ml) was added 10N HCl/MeOH (13 ml, 20×6.47 mmol) under ice-cooling. After stirring for 3 hr at room temperature, the precipitated crystals were filtered off and rinsed with ethyl ether to give hydrochloride (2.514 g). mp. (decomp.) >245° C., yield 97.2%.

Elemental analysis ($C_{16}H_{18}N_3O_3S_2Cl$ $0.3H_2O$) Calcd.: C, 47.41; H, 4.63; N, 10.37; S, 15.82 Cl; 8.75 Found: C, 47.38; H, 4.65; N, 10.35; S, 15.65 Cl; 9.15. IR (Nujol):3350,1728, 1690,1590. NMR ($d_6$-DMSO): 2.12(s, 3H), 4.52 (t, J=8.2 Hz, 1H), 7.62 (d, J=8.6 Hz, 2H) 7.78 (d, J=8.6 Hz, 2H), 7.84 (s, 1H).

(13) 13→A-1

To a solution of a starting compound (300 mg, 0.75 mmol) in methylene chloride (12 ml) were added triethylamine (0.23 ml, 2.2×0.75mmol)and then acetyl chloride (64 μl, 1.2×0.75mmol) under ice-cooling and the mixture stirred for 2 hr at the same temperature. After the addition of methyl ethyl ketone, the reaction solution was washed with 2N HCl and $H_2O$ in series, dried over $Na_2SO_4$ and concentrated in vacuo. The residue was subjected to silica gel column chromatography and fractions eluting with methylene chloride/methanol (10:1) were collected and recrystallized from acetone/ethyl ether to obtain an aimed product (261 mg). mp. 143–146° C., yield 85.8%.

Elemental analysis ($C_{18}H_{19}N_3O_4S_2$ $0.6H_2O$) Calcd.: C, 51.93; H, 4.89; N, 10.09; S, 15.40 Found: C, 52.05; H, 5.01; N, 10.05; S, 15.23. IR (Nujol):3275,1740,1702,1675,1590. NMR ($d_6$-DMSO): 1.83 (s, 3H×17/100 E or Z), 2.01 (s, 3H×83/100 E or Z), 2.10 (s, 13H×7/100 E or Z), 2.12 (s , 3H×83/100 E or Z).

Various compounds were synthesized from the corresponding starting materials in a manner similar to those described in Examples above. Physicochemical values of the resultant compounds are shown in Table A, 1 to 5.

TABLE A-1

| | Y₁—Y₂ | R¹ | B | IR (Nujol cm⁻¹) | NMR (CDCl₃ ppm) |
|---|---|---|---|---|---|
| A-1 | COCH₃ | CH₃ | O | 1740, 1702 | 2.01(s, CH₃), 2.12(s, CH₃), d-DMSO |
| -2 | OC-C₆H₅ | H₂C-C₆H₅ | S | 1705, 1588 | 3.81(s, —CH₂—), 7.60(s, —CH=), d-DMSO |
| -3 | | | O | 1746, 1708, 1596 | 3.74(s, —CH₂—), 7.62(s, —CH=) |
| -4 | | H₂C—C₆H₂(tBu)₂(OCH₃) | O | 1748, 1705, 1587 | 1.35(s, tBu), 3.62(s, CH₃), 7.62(s, =CH=), CHCl₃ |
| -5 | | H₂C-naphthyl | O | 1738, 1704, 1595 | 3.88(s, —CH₂—), 7.60(s, —CH=) |
| -6 | | H₂C-C₆H₄-C₆H₅ | O | 1735, 1695, 1673 | 3.78(s, —CH₂—), 7.68(s, —CH=) |
| -7 | | H₂C-C₆H₄-CF₃ | O | 1738, 1704, 1590 | 3.79(s, —CH₂—), 7.62(s, —CH=) |
| -8 | | H₂C-C₆H₃(CF₃)₂ | O | 1738, 1704, 1590 | 3.73(s, —CH₂—), 7.63(s, —CH=) |
| -9 | | H₂C-C₆H₂(OCH₃)₃ | O | 1739, 1704, 1591 | 3.77(s, CH₃ × 2), 3.81(s, CH₃), 7.62(s, —CH=) |
| -10 | | H₂C-C₆H₂(CH₃)₃ | O | 1738, 1703, 1587 | 2.21(s, CH₃), 2.32(s, CH₃ × 2), 7.68(s, —CH=) |

TABLE A-1-continued

Structure: R¹S-[pyrrolidine with N-Y₁-Y₂]-C(=O)-NH-[phenyl]-CH=[thiazolidinone with =B and NH]

| | Y₁-Y₂ | R¹ | B | IR (Nujol cm⁻¹) | NMR (CDCl₃ ppm) |
|---|---|---|---|---|---|
| -11 | | H₂C-CH=C(CH₃)-CH₂-CH₂-CH=C(CH₃)-CH₃ | O | 1738<br>1704<br>1590 | 1.51(s, CH₃)<br>7.68(s, —CH=)<br>1.58(s, CH₃)<br>1.66(s, CH—) |
| -12 | | HC(C₆H₅)₂ | O | 1738<br>1704<br>1592 | 5.19(s, —CH<)<br>7.63(s, —CH=) |
| -13 | COH | H₂C-C₆H₅ | S | 1705<br>1655<br>1587 | 3.81(s, —CH₂—)<br>7.68(s, —CH=)<br>8.21(s, CHO) |
| -14 | COCH₃ | | S | 1710<br>1695<br>1590 | 1.96(s, CH₃)<br>3.86(s, —CH₂—)<br>7.68(s, —CH=)<br>d-DMSO |
| -15 | OC-C₆H₄-CF₃ | CH₃ | S | 1700<br>1615<br>1584 | 2.15(s, —CH₃)<br>7.45(s, —CH=) |

TABLE A-2

Structure: R¹S-[pyrrolidine with N-Y₁-Y₂]-C(=O)-NH-[phenyl]-CH=[thiazolidinone with =B and NH]

| | Y₁-Y₂ | R¹ | B | IR (Nujol cm⁻¹) | NMR (d-DMSO ppm) |
|---|---|---|---|---|---|
| A-16 | COOᵗBu | —CH(CH₃)₂ | S | 1730<br>1688<br>1672 | 1.27(d, CH₃)<br>1.30(d, CH₃)<br>1.49(s, ᵗBu)<br>CDCl₃ |
| -17 | | H₂C-C₆H₅ | S | 1720<br>1690<br>1668 | 1.47(s, ᵗBu)<br>3.79(s, —CH₂=)<br>CDCl₃ |
| -18 | H.HCl | | S | 1720<br>1684<br>1590 | 3.87(s, —CH₂—)<br>7.61(s, —CH=) |
| -19 | CO(CH₂)₁₂CH₃ | CH₃ | S | 1715<br>1702<br>1592 | 2.14(s, CH₃ × 1/5)<br>2.47(s, CH₃ × 4/5)<br>CD₃OD |

TABLE A-2-continued
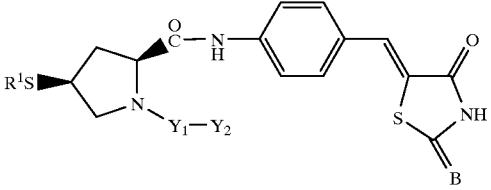
| | $Y_1-Y_2$ | $R^1$ | B | IR (Nujol cm$^{-1}$) | NMR (d-DMSO ppm) |
|---|---|---|---|---|---|
| -20 | 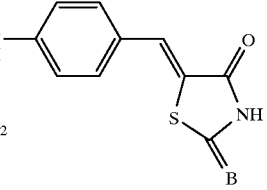 | | O | 1738<br>1695<br>1594 | 2.09(s, CH$_3$) |
| -21 | | | S | 1701<br>1585 | 2.09(s, CH$_3$) |
| -22 | 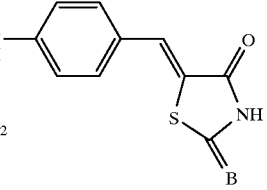 | | S | | 2.13(s, CH$_3$)<br>7.47(s, —CH=) |
| -23 | 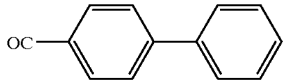 | 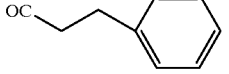 | S | 1694<br>1630<br>1574 | 3.82(s, —CH$_2$— ×<br>85/100)<br>3.88(s, —CH$_2$— ×<br>15/100)<br>KBr |
| -24 | 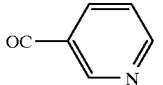 | | S | 1704<br>1625<br>1588 | 3.80(s, —CH$_2$— × 4/5)<br>3.88(s, —CH$_2$— × 1/5)<br>KBr |
| -25 | 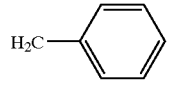 | CH$_3$ | O | 1745<br>1710<br>1695 | 2.09(s, CH$_3$ × 1/5)<br>2.12(s, CH$_3$ × 4/5)<br>7.72(s, —CH=) |
| -26 | | | S | 1700<br>1585 | 2.13(s, CH$_3$)<br>3.71(s, —CH$_2$—) |
| -27 | | 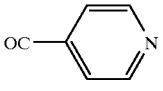 | S | 1705<br>1632<br>1585 | 1.23(d, CH$_3$)<br>1.24(d, CH$_3$) |
| -28 | 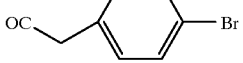 | 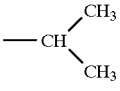 | S | 1702<br>1647<br>1585 | 3.87(s, —CH$_2$—)<br>CDCl$_3$ |
| -29 | 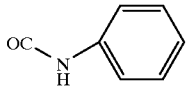 | | S | 1699<br>1586 | 3.86(s, —CH$_2$—)<br>7.58(s, —CH=) |
| -30 | 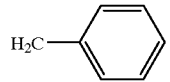 | | S | 1709<br>1584 | 3.80(s, —CH$_2$—)<br>7.57(s, —CH=) |

TABLE A-3

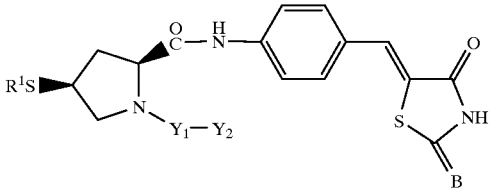

| | $Y_1$–$Y_2$ | $R^1$ | B | IR (Nujol cm$^{-1}$) | NMR (d-DMSO ppm) |
|---|---|---|---|---|---|
| A-31 | 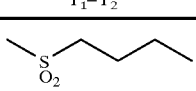 | 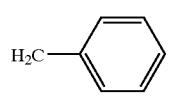 | S | 1710<br>1588 | 0.90(t, CH$_3$)<br>3.86(s, —CH$_2$—)<br>7.56(s, —CH=) |
| -32 | 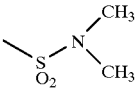 | | S | 1705<br>1588 | 2.70(s, CH$_3$ × 2)<br>3.87(s, —CH$_2$—)<br>7.54(s, —CH=) |
| -33 | 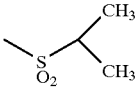 | | S | 1705<br>1585 | 1.32(d, CH$_3$)<br>1.36(d, —CH$_2$)<br>3.79(s, —CH$_2$—)<br>CDCl$_3$ |
| -34 | 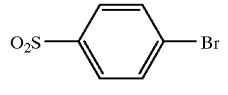 | CH$_3$ | S | 1710<br>1698 | 2.05(s, CH$_3$)<br>7.57(s, —CH=) |
| -35 | | | O | | 2.05(s, CH$_3$)<br>7.74(s, —CH=) |
| -36 | 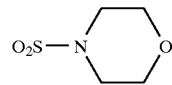 | 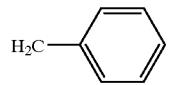 | S | 1695<br>1688 | 3.79(s, —CH$_2$—)<br>7.54(s, —CH=)<br>CDCl$_3$ |
| -37 | 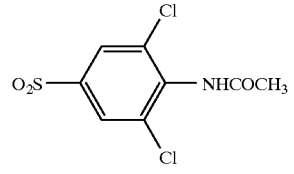 | | S | 1703<br>1580 | 2.14(s, CH$_3$)<br>3.80(s, —CH$_2$)<br>7.59(s, —CH=)<br>KBr |
| -38 | 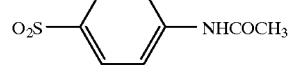 | | S | 1700<br>1589 | 2.15(s, CH$_3$)<br>3.73(s, —CH$_2$)<br>7.59(s, —CH=)<br>KBr |
| -39 | 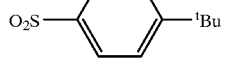 | | S | 1702<br>1592 | 1.33(s, $^t$Bu)<br>7.60(s, —CH=)<br>KBr |
| -40 | 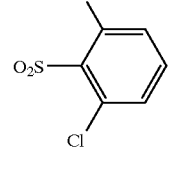 | CH$_3$ | O | 1740<br>1702<br>1588 | 2.13(s, —CH$_2$—)<br>7.80(s, —CH=)<br>CDCl$_3$ |
| -41 | |  | S | 1711<br>1580 | 3.74(s, —CH$_2$—)<br>8.05(s, —CH=)<br>CDCl$_3$ |

TABLE A-3-continued

| | Y₁–Y₂ | R¹ | B | IR (Nujol cm⁻¹) | NMR (d-DMSO ppm) |
|---|---|---|---|---|---|
| -42 | O₂S—C₆H₄—C₆H₅ (4-biphenylsulfonyl) | | O | 1741<br>1702<br>1593 | 3.69(s, —CH₂—)<br>7.77(s, —CH=)<br>CDCl₃ |
| -43 | | | S | 1701<br>1591 | 3.76(s, —CH₂—)<br>KBr<br>CDCl₃ |
| -44 | | CH₃ | O | 1742<br>1700<br>1595 | 2.07(s, CH₃)<br>7.75(s, —CH=)<br>CD₃OD |
| -45 | | | S | 1722<br>1695<br>1592 | 2.07(s, CH₃)<br>7.77(s, —CH=)<br>CD₃OD |
| -46 | | H₂C—C₆H₂(OCH₃)₃ (3,4,5-trimethoxybenzyl) | O | 1741<br>1702<br>1592 | 3.66(s, —CH₂—)<br>3.88(s, —CH₃)<br>3.82(s, CH₃ × 2) |

TABLE A-4

| | Y₁–Y₂ | R¹ | B | IR (KBr cm⁻¹) | NMR (CDCl₃ ppm) |
|---|---|---|---|---|---|
| A-47 | O₂S—C₆H₄—CH₂—C₆H₅ | CH₃ | S | 1701<br>1592 | 2.05(s, CH₃)<br>7.62(s, —CH=) |
| -48 | | H₂C—C₆H₅ (benzyl) | S | 1700<br>1592 | 3.67(s, —CH₂—)<br>7.62(s, —CH=) |
| -49 | O₂S—C₆H₄—N(CH₃)₂ | CH₃ | S | | 2.06(s, CH₃)<br>3.08(s, —CH₂—)<br>7.74(s, —CH=) |
| -50 | O₂S-2-naphthyl | CH₃ | O | 1742<br>1700 | 2.04(s, CH₃) |

TABLE A-4-continued
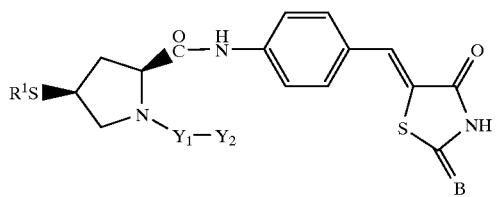
| | Y₁—Y₂ | R¹ | B | IR (KBr cm⁻¹) | NMR (CDCl₃ ppm) |
|---|---|---|---|---|---|
| -51 | 8-quinolinyl-SO₂ | H₂C—C₆H₅ | S | 1706<br>1581 | 3.64(s, —CH₂—)<br>7.60(s, —CH=)<br>d-DMSO |
| -52 | 5-(N(CH₃)₂)-naphth-1-yl-SO₂ | | S | 1700<br>1586 | 2.80(s, CH₃ × 2)<br>d-DMSO |
| -53 | 2,6-dichlorobenzyl-SO₂ | | S | 1702<br>1581 | 3.88(s, —CH₂—)<br>4.79(AB-d, 1H)<br>4.86(AB-d, 1H)<br>d-DMSO |
| -54 | 4-bromobenzyl-SO₂ | | S | 1709<br>1578 | 3.71(s, —CH₂—)<br>7.56(s, —CH=) |
| -55 | 4-fluorobenzyl-SO₂ | | S | 1703<br>1591 | 3.82(s, —CH₂—)<br>7.59(s, —CH=)<br>d-DMSO |
| -56 | 4-bromobenzyl-SO₂ | H₂C—C₆H₄—O(CH₂)₃CN | S | 1703 | 3.68(s, —CH₂—) |

TABLE A-5
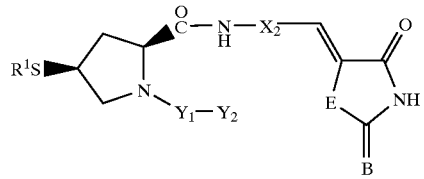
| | Y¹–Y² | R¹ | X₂ | B | E | IR (Nujol cm⁻¹) | NMR (DMSO ppm) |
|---|---|---|---|---|---|---|---|
| A-57 | O₂S–C₆H₄–N=N–C₆H₅ | H₂C–(o-tolyl) | –p-C₆H₄– | S | S | 1719 1694 1591 | 3.76(s, —CH₂—) 10.40(s, NH) |
| -58 | O₂S–(cyclopentadienyl)–SO₂–C₆H₅ | | | S | S | 1703 1584 | 3.77(s, —CH₂—) 10.41(s, NH) |
| -59 | O₂S–(4-Me-thiazol-5-yl, 2-NHAc) | | | S | S | 1686 1588 | 2.20(s, CH₃) 2.46(s, CH₃) 3.80(s, —CH₂—) 7.59(s, —CH=) |
| -60 | –C(O)–O–C₆H₅ | | 1-methylindol-3-yl | S | S | 1711 1600 1537 | 3.75(s, —CH₂—) 8.41(s, —CH= × 1/2) 8.45(s, —CH= × 1/2) CDCl₃ |
| -61 | | | | S | O | 1749 1714 1619 | 3.77(s, —CH₂—) 8.35(s, —CH=) CDCl₃ |
| -62 | –C(O)–O–C(CH₃)₃ | –C(C₆H₅)₃ | –p-C₆H₄– | S | O | 1753 1665 1594 | 1.41(s, —C(CH₃)₃) 6.42(s, NH) CDCl₃ |
| -63 | O₂S–C₆H₄–C₆H₅ | | | S | O | 1752 1672 1594 | 6.70(s, NH) 10.30(s, NH) |
EXAMPLE 2 (Method B₁)
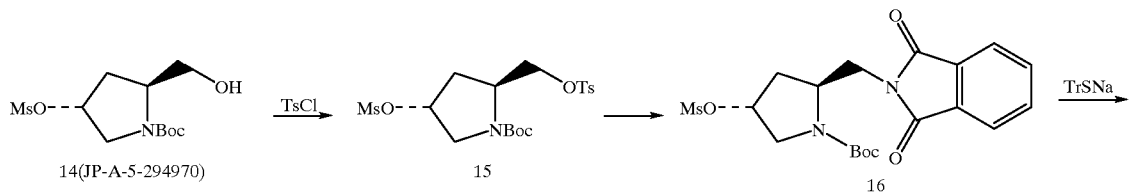

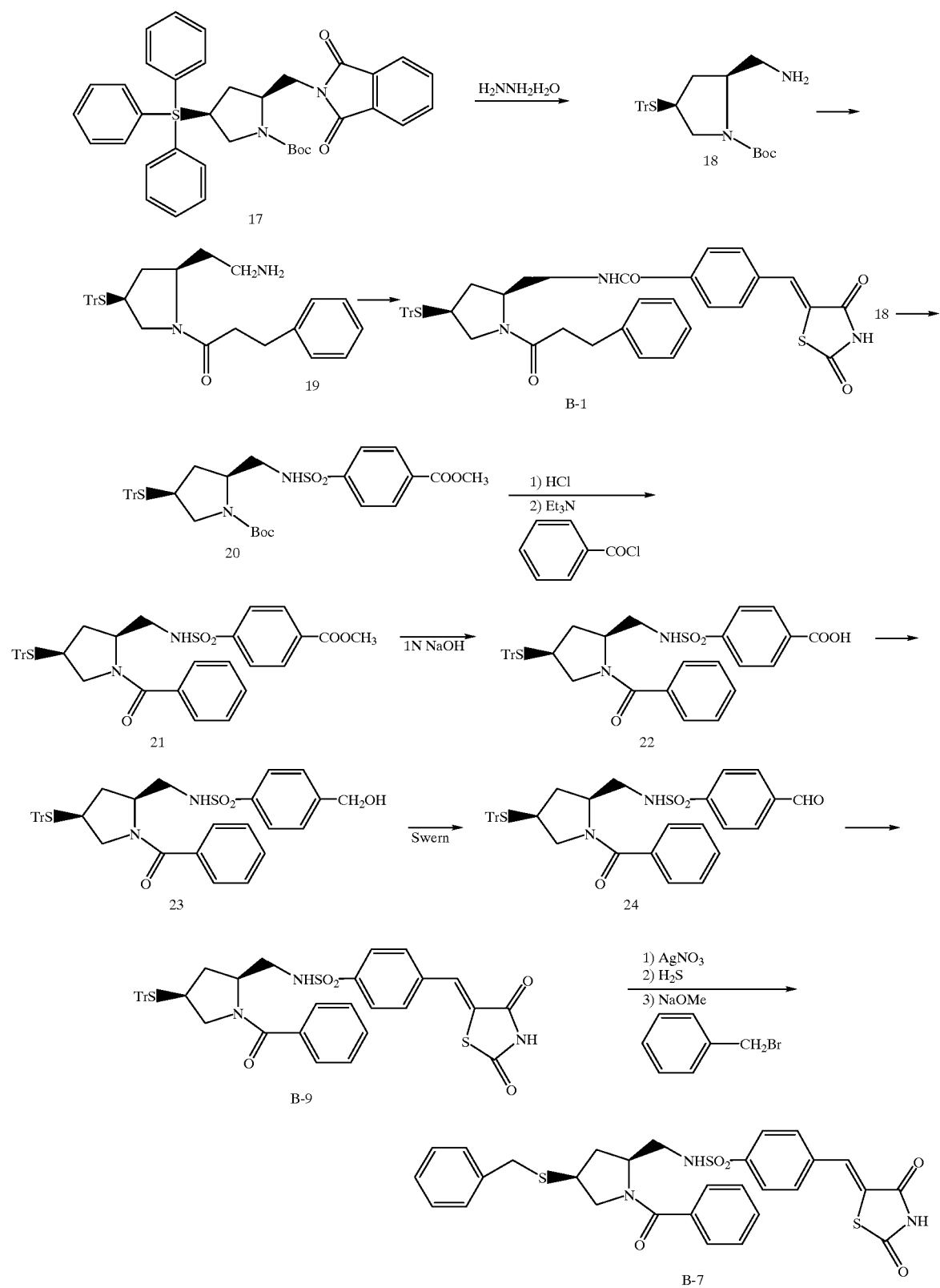
(1) 14→15
To a solution of a starting compound (44.38 g, 150 mmol) in methylene chloride (170 ml) were added triethylamine (25 ml, 1.2×150 mmol), p-toluenesulfonyl chloride (28.6 g, 150 mmol) and dimethylaminopyridine (0.91 g, 0.05×150 mmol) under ice-cooling. After stirring overnight at room temperature, the reaction solution was washed with 1N HCl, 5% NaHCO$_3$ and H$_2$O successively, dried over Na$_2$SO$_4$ and concentrated in vacuo. The residue was subjected to silica gel column chromatography and fractions eluting with hexane/ethyl acetate (1:1) were collected to obtain the tosyl compound (43.4 g) as a gum. Yield 64.4%. A portion was lyophilized from benzene and subjected to elemental analysis.

Elemental analysis (C$_{18}$H$_{27}$NO$_8$S$_2$O 0.4C$_6$H$_6$) Calcd.: C, 50.96; H, 6.16; N, 2.91; S, 13.34 Found: C, 50.88; H, 6.21; N, 3.11; S, 13.31. IR (CHCl$_3$): 1760,1692,1600. NMR (CDCl$_3$):1.41 (S, 9H), 2.45 (s, 3H), 3.03 (s, 3H), 5.19 (br-s, 1H).

(2) 15→16

To a solution of a starting compound (43.4 g, 96.5 mmol) in dimethylformamide (300 ml) was added potassium phthalimide (19.7 g). The mixture was stirred for 6 hr at 60° C., poured into water and extracted with ethyl acetate. The extract was washed with H$_2$O, dried over Na$_2$SO$_4$ and concentrated in vacuo. The residue was subjected to silica gel column chromatography and fractions eluting with hexane/ethyl acetate (1:1) were collected to obtain an aimed product (27.16 g) as foam. Yield 66.3%. A portion was lyophilized from benzene and subjected to elemental analysis.

Elemental analysis (C$_{19}$H$_{24}$N$_2$O$_7$S 0.1C$_6$H$_6$) Calcd.: C, 54.46; H, 5.74; N, 6.48; S, 7.42 Found: C, 54.75; H, 5.71; N, 6.08; S, 7.61. IR (CHCl$_3$): 1775,1718,1694. NMR (CDCl$_3$): 1.20–1.50 (m, 9H), 3.02 (s, 3H), 5.23 (m, 1H).

(3) 16→17

To a suspension of 60% sodium hydride (3.3 g, 1.3×64 mol) in dry tetrahydrofuran (100 ml) was added a solution of triphenylmethylmercaptane (24.8 g, 1.4×64 mmol) in dry tetrahydrofuran (100 ml) under stirring and ice-cooling over 10 min under a nitrogen atmosphere. The solution was stirred for another 10 min and added to a solution of a starting compound (27.16 g, 64 mmol) in dry tetrahydrofuran (100 ml) under ice-cooling. After stirring overnight at room temperature, the mixture was poured into water and extracted with ethyl acetate. The extract was washed with water, dried over Na$_2$SO$_4$ and concentrated in vacuo. The residue was subjected to silica gel column chromatography and fractions eluting with hexane/ethyl acetate (1:1) were collected to obtain an aimed product (30.22 g) as a foam. Yield 74.0%. A portion was lyophilized from benzene and subjected to elemental analysis.

Elemental analysis (C$_{37}$H$_{36}$N$_2$O$_4$S 0.3C$_6$H$_6$) Calcd.: C, 74.18; H, 6.06; N, 4.46; S, 5.10 Found: C, 74.18; H, 6.15; N, 4.33; S, 5.18. IR (CHCl$_3$): 1775,1715,1685.

(4) 17→18

To a solution of a starting compound (30.22 g, 50 mmol) in methylene chloride (50 ml) and methanol (300 ml) was added hydrazine hydrate (4.85 ml, 2×50 mmol) and the mixture was heated for 5 hr at 65° C., while distilling methylene chloride away. After cooling, methylene chloride (300 ml) was added to the mixture and the precipitated crystals were filtered off. The filtrate was washed with H$_2$O, dried over Na$_2$SO$_4$ and concentrated in vacuo. The residue was subjected to silica gel column chromatography and fractions eluting with methylene chloride/methanol (10:1) were collected to obtain the amine (23.7 g) as a foam. Yield 100%.

(5) 19→B-1

To a suspension of 4-(2,4-dioxothiazolidin-5-ylidenemethyl)benzoic acid (1.08 g, 1.1×3.95 mmol) in dimethylformamide (20 ml) were added 1-ethyl-3-(3-dimethylaminopropyl)carbodiimide hydrochloride (833 mg, 1.1×3.95 mmol) and then 1-hydroxybenzotriazole (534 mg, 3.95 mmol) and the mixture stirred for 10 min at room temperature. After addition of a starting compound (2 g, 3.95 mmol) in dimethylformamide (6 ml), the mixture was stirred overnight. The reaction mixture was poured into water and extracted with ethyl acetate. The extract was washed with 2N HCl, 5% NaHCO$_3$ and water successively, dried over Na$_2$SO$_4$ and concentrated in vacuo. The resultant residue was subjected to silica gel column chromatography. Fractions eluting with hexane/ethyl acetate/dichloromethane (1:2:0.58) were collected and recrystallized from dichloromethane/ethyl ether to obtain an aimed product (1.675 g). mp. (decomp.) 164–165° C., yield 57%.

Elemental analysis (C$_{44}$H$_{39}$N$_3$O$_4$S$_2$ 1.1CH$_2$Cl$_2$) Calcd.: C, 65.15; H, 5.00; N, 5.05 Found: C, 65.25; H, 5.07; N, 5.13. IR (CHCl$_3$): 3388,1752,1709,1658,1618,1524,1423. NMR (CDCl$_3$): 1.65 (m, 1H), 1.90 (m, 1H), 2.40–2.80 (m, 5H), 2.90 (t, J=5 Hz, 2H), 3.28 (m, 1H), 3.60 (m, 1H), 4.20 (m, 1H), 6.90–7.55 (m, 24H), 7.90 (s, 1H), 9.04 (s, 1H).

(6) 18→20

To a solution of the amine (8 g, 16.85 mmol) in methylene chloride (170 ml) were added triethylamine (3.5 ml,1.5× 16.85 mmol) and methyl p-chlorosulfonylbenzoate (4.74 g, 1.2×16.85 mmol) and the mixture stirred over night at room temperature. The reaction mixture was washed with 2N HCl and then water, dried over Na$_2$SO$_4$ and concentrated in vacuo. The residue was subjected to silica gel column chromatography and fractions eluting with ethyl acetate /methanol (4:1) were collected to obtain methyl ester (10.18 g) as a foam. Yield 97.0%.

Elemental analysis (C$_{37}$H$_{40}$N$_2$O$_6$S$_2$) Calcd.: C, 66.05; H, 5.99; N, 4.16; S, 9.53 Found: C, 65.98; H, 5.99; N, 4.16; S, 9.36. IR (CHCl$_3$): 1728,1673,1598.

(7) 20→21

To a solution of the methyl ester (10.18g, 15.12mmol) in methanol (150 ml) and methylene chloride (10 ml) was added hydrochloric acid (27 g) under ice-cooling. The mixture was allowed to stand for 10 min at room temperature and concentrated in vacuo. To the residue was added toluene and concentrated in vacuo, which procedure was repeated twice. To a solution of the residue in methylene chloride (150 ml) were added triethylamine (6.3 ml, 3×15.12 mmol), then benzoyl chloride (1.93 ml, 1.1×15.12 mmol) under ice-cooling. After stirring overnight at room temperature, the reaction mixture was washed with 2N HCl, 5% NaHCO$_3$ and H$_2$O successively, dried over Na$_2$SO$_4$, and concentrated in vacuo. The residue was subjected to silica gel column chromatography and fractions eluting with hexane/ethyl acetate (1:1) were collected to obtain an aimed product (9.9 g) as a foam. Yield 96.7%. A portion was lyophilized from benzene and subjected to elemental analysis.

Elemental Analysis (C$_{39}$H$_{36}$N$_2$O$_5$S$_2$ 0.2C$_6$H$_6$) Calcd.: C, 69.73; H, 5.41; N, 4.05; S, 9.26 Found: C, 69.72; H, 5.55; N, 4.14; S, 8.90. IR (CHCl$_3$): 3202,1728,1614,1577. NMR (CDCl$_3$):3.95 (s,—COOCH$_3$), 4.10 (m, 1H).

(8) 21→22

To a solution of a starting compound (methyl ester) (9.4 g, 13.9 mmol) in methanol (100 ml) was added 1N KOH (28 ml, 213.9 mmol) and the mixture was warmed at 50° C. for 7 hr. The reaction solution was acidified with 2N HCl in the presence of ethyl acetate. The organic layer was washed with brine, and concentrated in vacuo to obtain the carboxylic acid (9.2 g) as a foam. Yield 99.9%. A portion was lyophilized from benzene and subjected to the elemental analysis.

Elemental analysis (C$_{38}$H$_{34}$N$_2$O$_5$S$_2$ 0.6 C$_6$H$_6$, 0.5 H$_2$O) Calcd.: C, 69.01; H, 5.36; N, 3.98; S, 9.12 Found: C, 69.11; H, 5.44; N, 4.01; S, 8.87. IR (CHCl$_3$): 2500–3500br,1703, 1601,1571.

(9) 22→23

To a solution of a starting compound (carboxylic acid) (8.56 g, 13.57 mmol) in dry tetrahydrofuran (90 ml) were added triethylamine (2 ml, 1.1×13.57 mmol), and then ethyl chlorocarbonate (1.42 ml, 1.1×13.57 mmol) under ice-cooling. The mixture was stirred for 30 min at the same temperature, and poured into a suspension of sodium borohydride (1.28 g, 2.5×13.57 mmol) in water (30 ml) under ice-cooling. The mixture was stirred for 1 hr at the same temperature and partitioned into a mixture of water and ethyl acetate containing 2N HCl. The organic layer was washed with brine, dried over $Na_2SO_4$, and concentrated in vacuo. The residue was subjected to silica gel column chromatography and fractions eluting with hexane/ethyl acetate (1:2) were collected to obtain the alcohol (7.70 g) as a foam. Yield 87.5%. A portion was lyophilized from benzene and subjected to elemental analysis.

Elemental Analysis ($C_{38}H_{36}N_2S_2O_4$ $0.5H_2O$) Calcd.: C, 71.59; H, 5.71; N, 4.07; S, 9.32 Found: C, 71.44; H, 5.78; N, 3.96; S, 9.02. IR ($CHCl_3$): 3610,3380,1616,1576. NMR ($CDCl_3$): 1.54–2.05 (m, 3H), 2.30–2.79 (m, 3H), 2.90–3.03 (m, 1H), 3.20–3.30 (m, 1H), 4.09 (m, 1H), 4.72 (s, arom-$CH_2$—) 6.00 (br, 1H), 6.90–7.54 (m, 22H), 7.76 (d, J=8.5 Hz, 2H).

(10) 23→24

Under a nitrogen atmosphere, to a solution of oxalyl chloride (1.35 ml, 1.3×11.87 mmol) in methylene chloride (40 ml) was added a solution of dimethyl sulfoxide (2.2 ml, 2.6×11.86 mmol) in methylene chloride (5 ml) at −78° C. over 5 min with stirring. After stirring for 15 min at the same temperature, a solution of a starting compound (7.70 g, 11.87 mmol) in methylene chloride (20 ml) was added thereto over 5 min. The mixture was stirred for another 15 min and triethylamine (8.24 ml, 5×11.87 mmol) was added thereto. The reaction solution was allowed to warm up to room temperature slowly, washed with 2N HCl, 5% $NaHCO_3$ and $H_2O$, successively, dried over $Na_2SO_4$, and concentrated in vacuo. The residue was subjected to silica gel column chromatography and fractions eluting with hexane/ethyl acetate (1:1) were collected to obtain the aldehyde (6.21 g) as a foam. Yield 80.9%. A portion was lyophilized from benzene and subjected to elemental analysis.

Elemental Analysis ($C_{38}H_{34}N_2O_4S_2$ $0.6C_6H_6$ $0.3H_2O$) Calcd.: C, 71.47; H, 5.51; N, 4.01; S, 9.17 Found: C, 71.26; H, 5.44; N, 4.23; S, 8.90. IR ($CHCl_3$): 3381, 1709, 1616, 1577. NMR ($CDCl_3$): 1.60 (m, 1H), 2.00 (m, 1H), 2.33–2.78 (m, 3H), 2.98 (m, 1H), 3.35 (m, 1H), 4.12 (m, 1H), 6.58 (m, 1H), 6.92–7.57 (m, 20H), 7.90–8.00 (m, 2H), 10.02 (s, 1H).

(11) 24→B-9

Compound B-9 was prepared according to the Knoevenagel reaction in a manner similar to that described in Example 1, (11) for the preparation of compound (12) from compound (11). Yield 65.7%.

Elemental Analysis ($C_{41}H_{35}N_3S_3O_5$ $0.3H_2O$) Calcd.: C, 65.54; H, 4.78; N, 5.59; S, 12.80 Found: C, 65.61; H, 4.92; N, 5.59; S, 12.59. IR ($CHCl_3$): 3388,1754,1710,1609,1574. NMR ($CDCl_3$): 1.56 (m, 1H), 2.00 (m, 1H), 2.35–2.84 (m, 3H), 3.04 (m, 1H), 3.36 (m, 1H), 4.12 (m, 1H), 6.10 (m, 1H), 6.90–7.58 (m, 22H), 7.71 (s, 1H), 7.89 (d, J=8 Hz, 2H), 9.47 (s, 1H).

EXAMPLE 3 (Method B; B-9→B-7)

To a solution of tritylthio derivative (600 mg, 0.8 mmol) in methanol (7 ml) and tetrahydrofuran (2 ml) was added pyridine (0.16 ml, 2.5×0.8 mmol) and the mixture stirred under ice-cooling. After the addition of silver nitrate (313 mg, 2.3×0.8 mmol) in methanol (1 ml) and water (1 ml), the mixture was stirred for 10 min. The precipitated crystals were filtered off and rinsed with methanol and ethyl ether successively. Hydrogen sulfide gas was bubbled into a suspension of the resultant silver salt in methylene chloride (15 ml) under ice-cooling and stirring for 10 min. The mixture was stirred for another 30 min at room temperature and filtered through Hyflo Super-Cel™ to remove silver salt. The filtrate was concentrated in vacuo to give a thiol as a foam. To a solution of the thiol in methylene chloride (7 ml) were added 1N sodium methoxide solution(1.52 ml, 1.9×0.8 mmol) in methanol under ice-cooling, and 5 min later, benzyl bromide (143 μl, 1.5×0.8 mmol). After stirring for 30 min, the mixture was poured into water/methyl ethyl ketone containing 2N HCl for partition. The organic layer was washed with water, dried over $Na_2SO_4$, and concentrated in vacuo. The residue was subjected to silica gel column chromatography and fractions eluting with methylene chloride/methanol (25:1) were collected and recrystallized from acetone/hexane to give an aimed product (289 mg). mp. 212–214° C.

Elemental analysis ($C_{29}H_{27}N_3O_5S_3$) Calcd.: C, 58.67; H, 4.58; N, 7.08; S, 16.20 Found: C, 58.57; H, 4.63; N, 7.00; S, 16.00. IR (Nujol):3300,1764,1705,1588,1560,1455. NMR (d-DMSO): 3.73 (s, 2H), 4.15 (m, 1H), 7.80 (s, 1H).

The compounds prepared in a manner similar to that described in Examples 2 and 3 are shown in Table $B_1$, 1 to 2.

TABLE $B_1$-1

| | $Y_1-Y_2$ | $R^1$ | B | IR ($CHCl_3$ ppm) | NMR ($CDCl_3$ ppm) |
|---|---|---|---|---|---|
| B-1 | OC~~⟨Ph⟩ | —C—(Ph)$_3$ | O | 1752<br>1709<br>1658 | 2.91(t, —$CH_2$—)<br>7.89(s, —CH=) |

TABLE B₁-1-continued
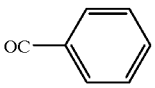
| Y₁–Y₂ | R¹ | B | IR (CHCl₃ ppm) | NMR (CDCl₃ ppm) |
|---|---|---|---|---|
| -2 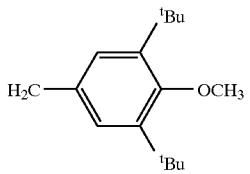 | 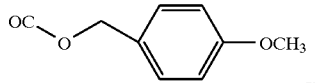 | O | 1751 1709 1648 1579 | 1.34(s, ᵗBu × 2) 3.62(s, CH₃) 3.67(s, —CH₂—) |
| -3 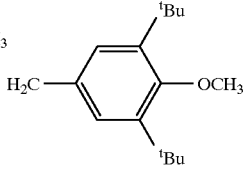 | 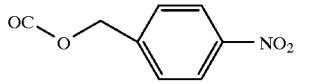 | O | 1751 1709 1667 | 1.42(s, ᵗBu × 2) 4.88(s, —CH₂—) |
| -4 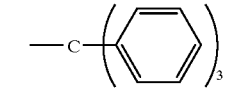 | 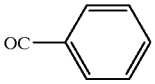 | O | 1751 1710 1611 | 5.17(s, —CH₂—) 7.78(s, —CH=) |
| -5 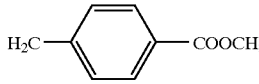 | 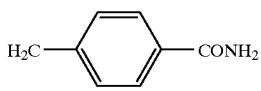 | S | 1722 1655 1032 1576 | 3.86(s, CH₃) Nujol |
| -6 | 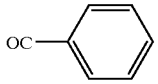 | S | 1703 1639 1563 | 3.77(s, —CH₂—) Nujol d-DMSO |
TABLE B₁-2
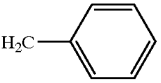
| | Y₁–Y₂ | R¹ | IR (Nujol cm⁻¹) | NMR (CDCl₃ ppm) |
|---|---|---|---|---|
| B-7 | (OC-phenyl) | (H₂C-phenyl) | 1764 1705 1588 | 3.64(s, —CH₂—) d-DMSO |
| -8 | | 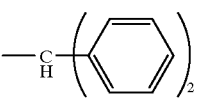 | 1748 1706 1605 | 5.35(s, —CH<) |

TABLE B₁-2-continued
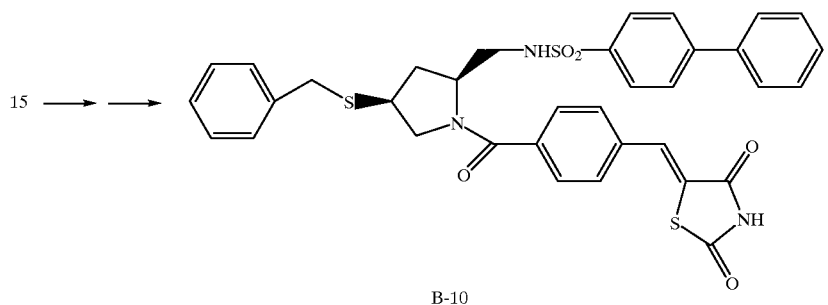
| Y₁-Y₂ | R¹ | IR (Nujol cm⁻¹) | NMR (CDCl₃ ppm) |
|---|---|---|---|
| -9 | —C(C₆H₅)₃ | 1754<br>1710<br>1574 | 7.71(s, —CH=) |
EXAMPLE 4 (Method B₂)
The compounds prepared in a manner similar to that described in Example 2 are shown in Table B₂.
TABLE B₂
| | | IR (Nujol cm⁻¹) | NMR (CDCl₃ ppm) |
|---|---|---|---|
| B-10 | | 1752<br>1708<br>1592 | 3.70(s, —CH₂—)<br>4.27(m, 1H)<br>7.77(s, —CH=) |

TABLE B₂-continued

| | | IR (Nujol cm⁻¹) | NMR (CDCl₃ ppm) |
|---|---|---|---|
| -11 | 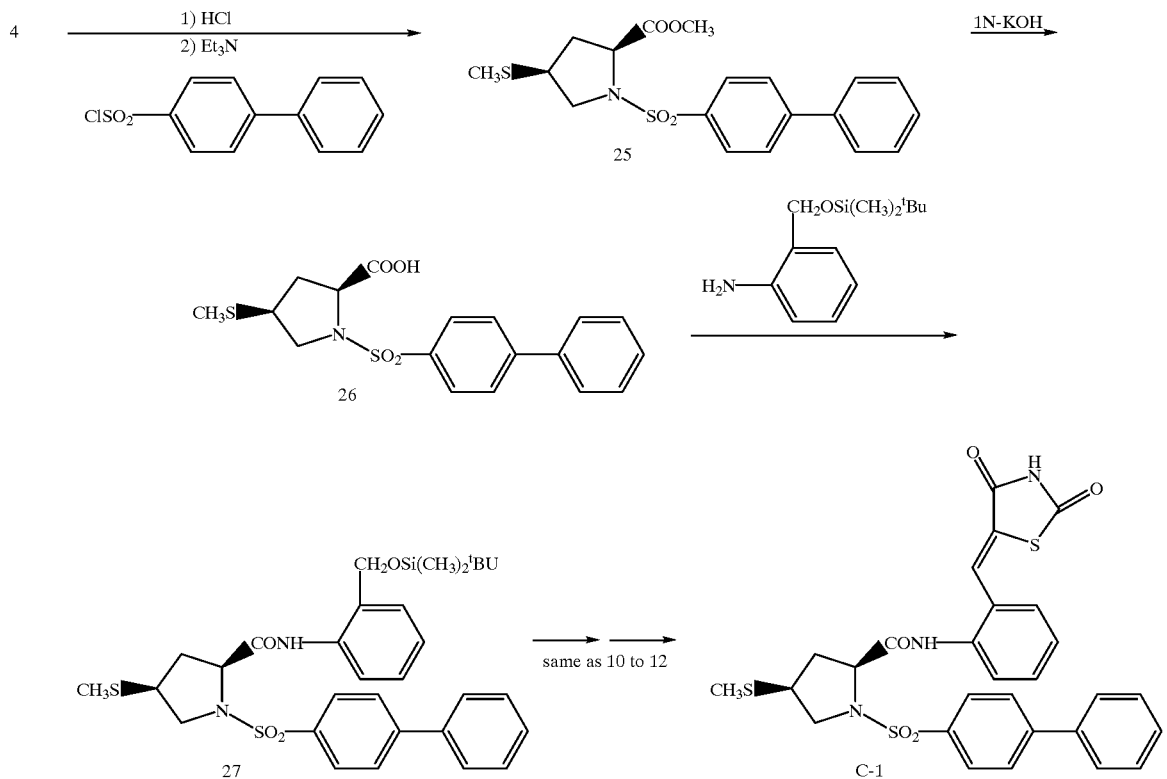 | 1745<br>1706<br>1617 | 3.85(m, 1H)<br>4.48(m, 1H)<br>5.14(s, —CH<) |

EXAMPLE 5 (Method C)

(1) 4→25

To a solution of a starting compound (methyl ester) (7.53 g, 27.35 mmol) in ethyl acetate (15 ml) was added 4N HCl (34.2 ml, 5×27.35 mmol) under ice-cooling and the mixture stirred for 2 hr at room temperature. After removing the hydrogen chloride gas under reduced pressure, ethyl ether and hexane were added. The precipitated crystals were filtered off and rinsed with ethyl ether to give hydrochloride (5.42 g). To a solution of the hydrochloride (2.0 g, 9.4 mmol) in methylene chloride (40 ml) were added triethylamine (4 ml, 3×9.4 mmol), and then p-phenylbenzenesulfonyl chloride (3.73 g, 1.1×9.4 mmol) under ice-cooling. The mixture was stirred for 2 hr at room temperature. The reaction solution was washed with 2N HCl, 5% NAHCO₃ and H₂O, successively, dried over Na₂SO₄, and concentrated in vacuo. The residue was subjected to silica gel column chromatography and fractions eluting with hexane/ethyl acetate (1:1) were collected and recrystallized from benzene/hexane to give an aimed product (3.64 g). mp. 95.5–97.5° C., yield 98.9%.

Elemental analysis ($C_{19}H_{21}NO_4S_2$) Calcd.: C, 58.29; H, 5.41; N, 3.58; S, 16.38 Found: C, 58.24; H, 5.43; N, 3.57; S, 16.40. IR (Nujol): 1735,1697,1594,1562,1480,1460, 1439. NMR (CDCl₃): 2.03 (m, 1H), 2.08 (s, 3H), 2.54 (m, 1H), 3.02 (m, 1H), 3.27 (d.d, J=8.6,10.6 Hz, 1H), 3.74 (s, 3H), 3.90 (d.d, J=7.2,10.6 Hz, 1H), 4.47 (t, J=7.8 Hz, 1H), 7.40–7.55 (m, 3H), 7.57–7.66 (m, 2H), 7.70–7.79 (m, 2H), 7.92–8.01 (m, 1H).

(2) 25→26

To a mixture of the methyl ester (3.64 g, 9.3 mmol) in methanol (20 ml) and dimethyl sulfoxide (10 ml) was added 1N KOH (19 ml, 2×9.3 mmol) and the mixture stirred for 2 hr at room temperature. The reaction mixture was acidified with 2N HCl in the presence of ethyl acetate for partition, washed with brine, dried over $Na_2SO_4$, and concentrated in vacuo to obtain the carboxylic acid quantitatively.

(3) 26→27

To a solution of a starting compound (755 mg, 2 mmol) in dry tetrahydrofuran (5 ml) were added triethylamine (0.42 ml, 3 mmol) and then isobutyl chlorocarbonate(328 mg, 2.4 mmol) in dry tetrahydrofuran (1 ml) under ice-cooling. The mixture was stirred for 20 min. After the addition of 2-t-butyldimethylsilyloxymethylaniline (950 mg, 4 mmol), the mixture was stirred for 2 hr at room temperature. The reaction solution was poured into water and extracted with ethyl acetate. The extract was washed with 2N HCl, 5% $NaHCO_3$ and $H_2O$, successively, dried over $Na_2SO_4$, and concentrated in vacuo. The residue was subjected to silica gel column chromatography and fractions eluting with hexane/ethyl acetate (4:1) were collected to obtain an aimed product (1 g). Yield 84.2%.

Elemental analysis ($C_{31}H_{40}N_2O_4S_2Si$) Calcd.: C, 62.38; H, 6.75; N, 4.69; S, 10.74 Found: C, 62.29; H, 6.68; N, 4.74; S, 10.75. IR ($CHCl_3$): 3332,1678,1591,1525,1453,1358, 1164,1133. NMR($CDCl_3$): 0.11(s, 3H), 0.17(s, 3H), 0.94(s, 9H), 2.06(s, 3H), 2.15–2.43(m,2H), 2.87(m, 1H), 3.52(d.d, J=11.6, 6.6 Hz, 1H), 3.85(d.d, J=11.6, 7.0 Hz, 1H), 4.24(d.d, J=8.2, 6.4 Hz, 1H), 4.74(d, J=13.0 Hz, 1H), 4.97(d,J=13.0 Hz, 1H), 7.05–8.05(m, 13H), 9.48(brs, 1H).

The objective compound C-1 was obtained in a manner similar to that described in Example 1, (10) and (12). The compound C-1 and other compounds prepared in a similar manner are shown in Table C.

TABLE C-1

| | | IR (KBr cm$^{-1}$) | NMR (CDCl$_3$ ppm) |
|---|---|---|---|
| C-1 | 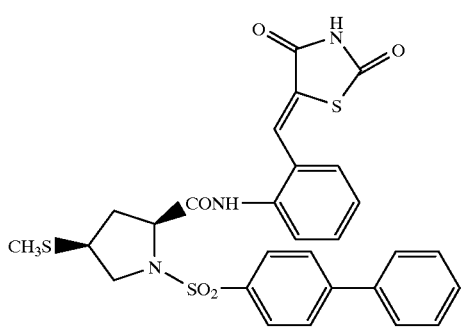 | 1745<br>1704<br>1596 | 2.11(s, CH$_3$) |
| -2 | 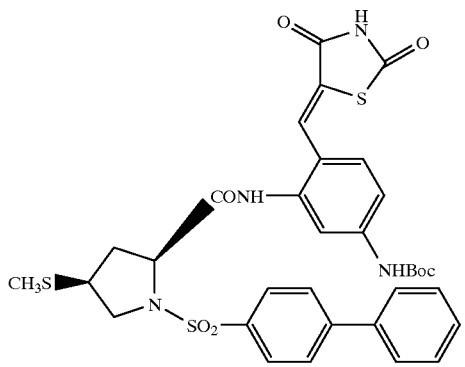 | 1743<br>1704<br>1609<br>1542 | 1.55(s, $^t$Bu)<br>2.09(s, CH$_3$)<br>7.80(s, —CH=) |
| -3 | 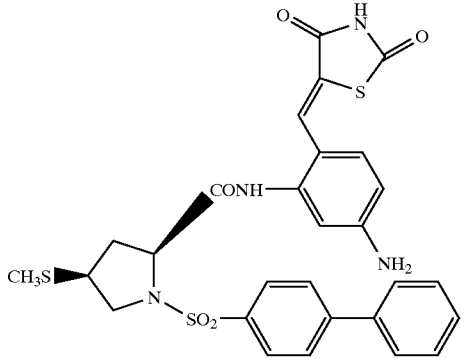 | 1742<br>1701<br>1609<br>1544 | 2.05(s, CH$_3$) |

TABLE C-2
| | | IR (Nujol cm$^{-1}$) | NMR (CDCl$_3$ ppm) |
|---|---|---|---|
| C-4 | | 1751<br>1705<br>1612<br>1572 | 3.92(s, —CH$_3$)<br>5.30(s, —CH<) |
| -5 | | 1741<br>1709<br>1613<br>1573 | 3.66(s, —CH$_3$)<br>5.29(s—CH<)<br>7.80(s, —CH=) |
| -6 | | 1742<br>1703<br>1610<br>1571 | 5.55(s, —CH=)<br>DMSO |
EXAMPLE 6 (Method D)
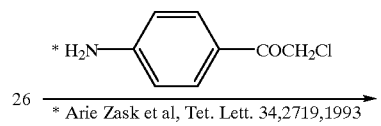
* Arie Zask et al, Tet. Lett. 34,2719,1993
-continued
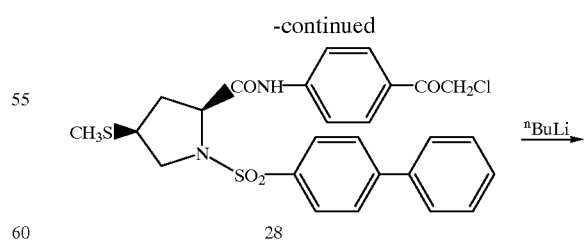

-continued

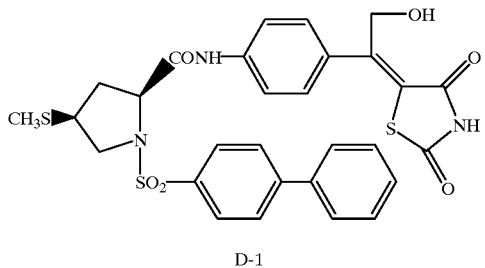

D-1

1) 26→28

To a solution of a starting compound (3.5 g, 9.3 mmol) in methylene chloride (35 ml) were added triethylamine (2.85 ml, 9.3 mmol) and isobutyl chlorocarbonate (1.33 ml, 1.1× 9.3 mmol) under ice-cooling, and the mixture stirred for 20 min. A solution of 4-amino-2-chloroacetophenone (1.74 g, 1.1×9.3 mmol) in dimethylformamide (10 ml) was added to the mixture. After stirring overnight at room temperature, ethyl acetate was added to the reaction solution. The solution was washed with 2N HCl, 5% $NaHCO_3$ and $H_2O$, successively, dried over $Na_2SO_4$, and concentrated in vacuo. The residue was subjected to silica gel column chromatography and fractions eluting with hexane/ethyl acetate (1:1) were collected and recrystallized from acetone/ethyl ether to obtain an aimed product (2.185 g). mp. 131–134° C., yield 44.4%.

Elemental analysis ($C_{26}H_{25}N_2O_4S_2Cl$) Calcd.: C, 59.03; H, 4.76; N, 5.29; S, 12.12 Cl; 6.70 Found: C, 58.99; H, 4.83; N, 5.27; S, 12.11 Cl; 6.61. IR (Nujol): 3358,1707,1693, 1595,1560,1521,1480,1459. NMR ($CDCl_3$): 2.07 (s, 3H), 2.20 (m, 1H), 2.43 (m, 1H), 3.07 (m, 1H), 3.65 (m, 1H), 4.23 (d.d, J=6,8 Hz, 1H), 4.70 (s, 3H), 7.40–8.00 (m, 13H), 9.02 (s, 1H).

(2) 28→D-1

To a solution of 2,4-thiazolidinedione (470 mg,4 mmol) in dry tetrahydrofuran (24 ml) was added 1.62 M n-butyllithium solution (4.94 ml, 2×4 mmol) in hexane at −78° C. in an atmosphere of argon and the mixture stirred for 30 min at 0° C. To the reaction mixture was added a solution of a starting compound (2.12 g, 5 mmol) in dry tetrahydrofuran (8 ml) at −78° C. over 3 min. After stirring overnight at room temperature, the mixture was poured into water/ methylene chloride containing 2N HCl for partition, washed with water, dried over $Na_2SO_4$, and concentrated in vacuo. The residue was subjected to silica gel column chromatography and fractions eluting with methylene chloride/ethyl acetate (3:1) were collected, and pulverized with methylene chloride/ethyl ether to obtain an aimed product (408 mg). Yield 16.7%.

Elemental analysis ($C_{29}H_{27}N_3S_3O_6$ 0.2 $(C_2H_5)_2O$) Calcd.: C, 57.31; H, 4.68; N, 6.73; S, 15.40 Found: C, 57.11; H, 4.58; N, 6.64; S, 15.14. IR (Nujol); 3460,3336,1736, 1696,1594,1560,1523,1479. NMR ($CDCl_3$): 2.03(s, 3/2H), 2.05(s, 3/2H), 2.20–2.34(m, 2H), 2.93(m, 1H), 3.30–3.57 (m, 2H), 3.71(m, 1H), 4.23(t, J=7 Hz, 1H), 4.44(s, 2H), 7.16(d, J=8.6 Hz, 2H),7.40–7.65(m, 7H), 7.78(d, J=8.6 Hz, 2H), 7.93(d, J=8.6 Hz, 2H), 8.94(s, 1H),9.09(s, 1H).

The compounds prepared in a manner similar to the above are shown in Table D.

TABLE D

| | $Y_1$–$Y_2$ | $R^1$ | IR (Nujol cm$^{-1}$) | NMR ($CDCl_3$ ppm) |
|---|---|---|---|---|
| D-1 | $O_2S$–C$_6$H$_4$–C$_6$H$_5$ | $CH_3$ | 1736 1696 1594 | 2.08(s, $CH_3$) 4.82(d, —$CH_2$—) |
| -2 | $H_2C$–C$_6$H$_5$ | | 1734 1693 1593 | 3.68(s, —$CH_2$—) 4.81(d, —$CH_2$—) |
| -3 | OC–CH$_2$–C$_6$H$_4$–Br | | 1734 1690 1630 1599 | 3.57(s, —$CH_2$— × 1/2) 3.75(d, —$CH_2$— × 1/2) 4.75(d, —$CH_2$—) |

EXAMPLE 7 (Method E₁)

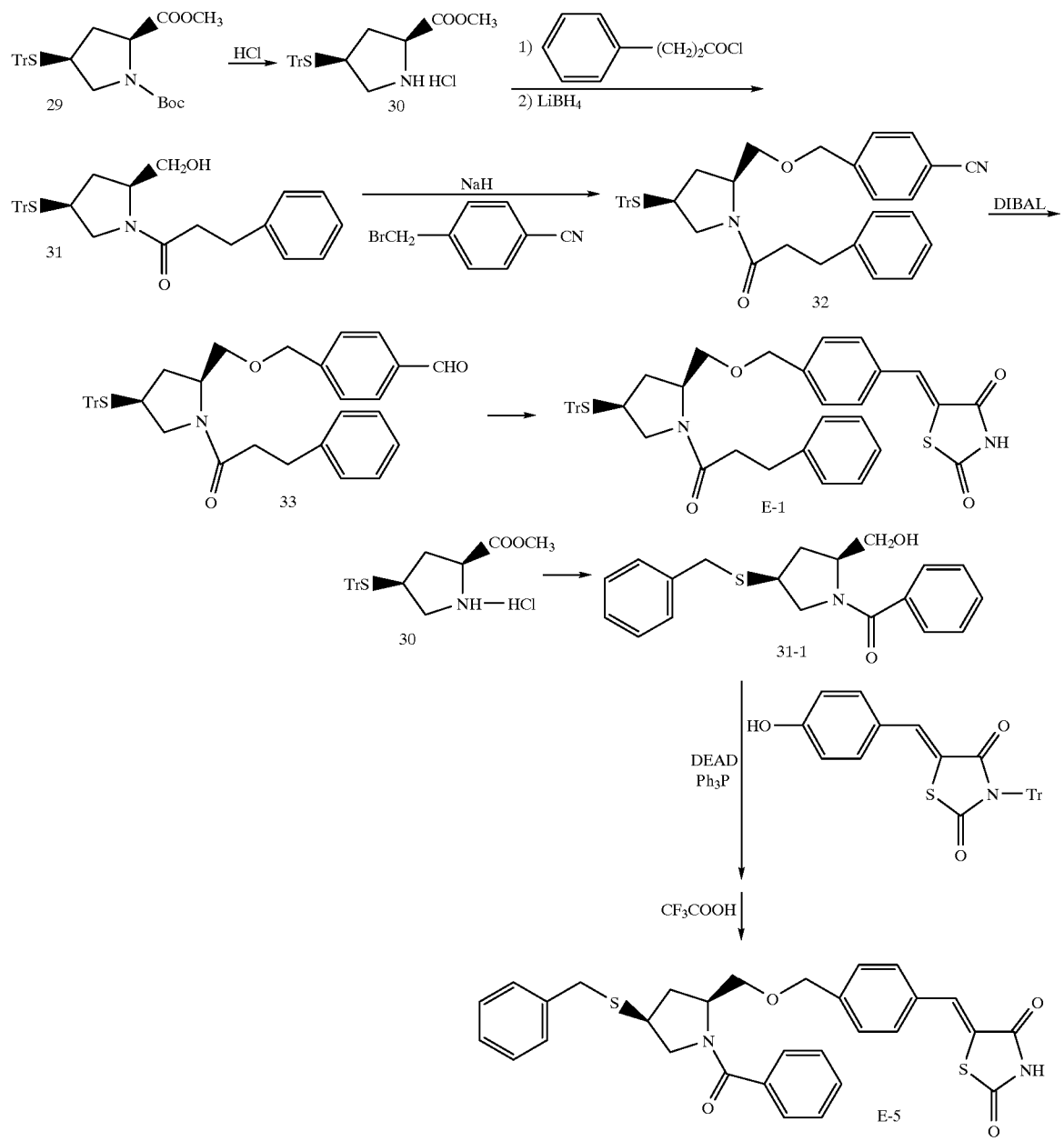

(1) 29→30

Under a nitrogen atmosphere, to a solution of the compound 29 described in Japanese Patent Publication (KOKAI) 5-294970 (U.S. Pat. No. 5317016) (5.036 g, 10 mmol) in methanol (12 ml) and dichloromethane (30 ml) was added 3.66M HCl/MeOH (55 ml, 0.2 mole) under ice-cooling with stirring. The mixture was stirred for 5 hr at room temperature. After allowing to stand for 63 hr in a refrigerator, the reaction mixture was concentrated in vacuo, followed by azeotropic distillation with dry toluene to dryness. The aimed product was obtained quantitatively.

NMR (CDCl₃): 1.78–1.93 (1H, m), 2.05–2.30 (1H, m), 3.02 (3H, m), 3.70 (3H, s), 4.18 (1H, bs), 7.18–7.45 (15H, m), 8.78 (1H, bs), 10.88 (1H, bs).

(2) 30→31

Under a nitrogen atmosphere, to a solution of the hydrochloride (30) (4.78 g, 10.885 mmol) obtained above in dry dichloromethane (20 ml) were added TEA (triethylamine) (3.6 ml, 26 mmol) and then 3-phenylpropionyl chloride (1.94 ml, 13 mmol) with stirring and under ice-cooling. The mixture was stirred for 2 hr at room temperature, poured into ice-water, and extracted with dichloromethane. The extract was washed with water, dried over Na₂SO₄, and concentrated in vacuo. The residue was subjected to silica gel column chromatography and fractions eluting with toluene/ethyl acetate were collected to obtain an aimed product (5.27 g). Yield 90.6%.

NMR (CDCl₃): 1.66–1.82 (1H, m), 2.22–2.37 (3H, m), 2.51–2.56 (1H, m), 2.73–2.99 (4H, m), 3.70 (3H, s), 4.16 (1H, t, J=8.6 Hz), 7.18–7.46 (20H, m).

The resultant ester (5.27 g, 9.84 mmol) was dissolved in dry tetrahydrofuran (33 ml). Under a nitrogen atmosphere, to the solution was added lithium borohydride (321 mg, 14.8 mmol) with stirring and under ice-cooling. After stirring for 3 hr at room temperature, the reaction mixture was poured into ice-water containing ammonium chloride, and extracted with ethyl acetate. The extract was washed with brine, dried over $Na_2SO_4$, and concentrated in vacuo. The resultant residue was subjected to silica gel column chromatography and fractions eluting with toluene/ethyl acetate were collected, and recrystallized from ether/pentane to obtain an aimed product (4.68 g). mp. 108–112° C., yield 93.7%.

Elemental analysis ($C_{33}H_{33}NO_2S$) Calcd.: C, 78.07; H, 6.55; N, 2.76; S, 6.32 Found: C, 78.06; H, 6.68; N, 2.79; S, 6.19. IR ($CHCl_3$): 3328,1616. NMR ($CDCl_3$):1.25–1.42 (1H, m), 2.12–2.26 (3H, m), 2.35–2.86 (5H, m), 3.40–3.62 (2H, m), 3.85–3.99 (1H, m), 7.14–7.46 (20H, m).

(3) 31→32

Under a nitrogen atmosphere, to a solution of a starting compound (254 mg, 0.5 mmol) obtained above in dry tetrahydrofuran (3 ml) was added sodium hydride (60%, 30 mg, 0.75 mmol) at −70 ° C. with stirring, and the mixture was stirred for 30 min at room temperature. After cooling to −70° C., α-bromo-p-tolunitrile (147 mg, 0.75 mmol) was added with stirring, and the mixture stirred for another 18 hr at room temperature. The reaction mixture was poured into water, and extracted with ethyl acetate. The extract was washed with water, dried over $Na_2SO_4$, and concentrated in vacuo. The resultant residue was crystallized from ether/pentane to obtain the product (195 mg, mp 83–85 ° C.). The mother liquor was subjected to silica gel column chromatography (eluting with toluene/ethyl acetate), and crystallized from ether/pentane to obtain an aimed product (61 mg). Yield, 82%.

IR ($CHCl_3$): 2224,1630. NMR ($CDCl_3$): 1.84–2.00 (1H, m), 2.11–2.27 (2H, m), 2.31–2.39 (2H, m), 2.55–2.82 (4H, m), 3.54–3.69 (2H, m), 4.00–4.12 (1H, m), 4.50 (2H, s), 7.15–7.63 (20H, m).

(4) 32→33

The starting compound (32) (480 mg, 0.771 mmol) prepared in the above was dissolved in dry toluene (3 ml). Under a nitrogen atmosphere, to the solution was added 1M diisobutyl aluminium hydride solution (1.62 ml, 1.62 mmol) in hexane with stirring and under ice-cooling, and the mixture was stirred for 17 hr at room temperature, and for 1 hr while warming at 50° C. The reaction mixture was poured into ice-water (containing 3.3 ml 1N HCl, pH 4–5), and extracted with ethyl acetate. The extract was washed with water, dried over $Na_2SO_4$, and concentrated in vacuo. The resultant residue was subjected to silica gel column chromatography (eluting with toluene/ethyl acetate) to obtain an aimed product (106 mg, 22%, powder).

IR ($CHCl_3$): 1697,1626,1609. NMR ($CDCl_3$): 1.53–1.63 (1H, m), 1.86–2.03 (1H, m), 2.10–2.20 (1H, m), 2.28–2.63 (1H, m), 2.50–2.95 (5H, m), 3.54–3.70 (2H, m), 4.05 (1H, bs), 4.54 (2H, s), 7.10–7.50 (22H, m), 7.82–7.87 (2H, m), 10.00 (1H, s).

(5) 33→E-1

To a solution of the starting compound (33) (95 mg, 0.152 mmol) obtained in the above in dry toluene (2.6 ml) were added 0.1M piperidine solution (119 μl, 0.0119 mmol) in toluene, 0.1M acetic acid solution (119 μl, 0.0119 mmol) in toluene and 2,4-thiazolidinedione (27 mg, 0.228 mmol). The mixture was heated to reflux for 14 hr, poured into ice-water, extracted with ethyl acetate, washed with water, dried over $Na_2SO_4$, and concentrated in vacuo. The resultant residue was subjected to silica gel column chromatography (eluting with toluene/ethyl acetate) to obtain an aimed product (65 mg, foam, 59%).

IR ($CHCl_3$): 3386,2858,2756,1742,1702,1619,1604. NMR ($CDCl_3$): 1.86–2.02 (1H, m), 2.13–2.91 (8H, m), 3.53–3.70 (2H, m), 4.03–4.15 (1H, m), 4.50 (2H, s), 7.13–7.47 (24H, m), 7.76 (1H, s), 9.51 (1H, s).

(6) 31-1→E-5

To a solution of the compounds (31-1) (98 mg, 0.3 mmol) and (31-2) (175 mg, 0.38 mmol) prepared in accordance with the method described in Example 1 above, and triphenylphosphine (88 mg, 0.33 mmol) in THF (5 ml) was added dropwise diethyl azodicarboxylate (DEAD) (50 μl, 0.32 mmol) under ice-cooling. After stirring for 10 min at the same temperature, the reaction mixture was allowed to warm to room temperature and stirred overnight. The solvent was removed by distillation in vacuo. The residue was subjected to silica gel column chromatography (eluting with toluene/ethyl acetate (10:1)) to obtain the ether (56 mg, 24%). To a solution of the ether in dichloromethane (2 ml) was added trifluoroacetic acid (0.1 ml, 1.3 mmol) under ice-cooling, and the mixture stirred for 1 hr. The mixture was then stirred for 2 hr at room temperature. The solvent was removed in vacuo to leave a residue, which was subjected to preparative thin-layer chromatography (developing with dichloromethane/ethyl acetate (3:1)) to obtain an aimed product (30 mg, 78%).

IR (KBr): 1739,1700,1596,1509. NMR ($CDCl_3$) :1.95–2.18 (1H, m), 2.40–2.59 (1H, m), 2.90–3.10 (1H, m), 3.20–3.55 (2H, m), 3.72 (2H, s), 4.25–4.65 (3H, m), 7.00–7.50 (14H, m), 7.56 (1H, s) 8.55–8.75 (1H, brs).

EXAMPLE 8 (Method $E_2$)

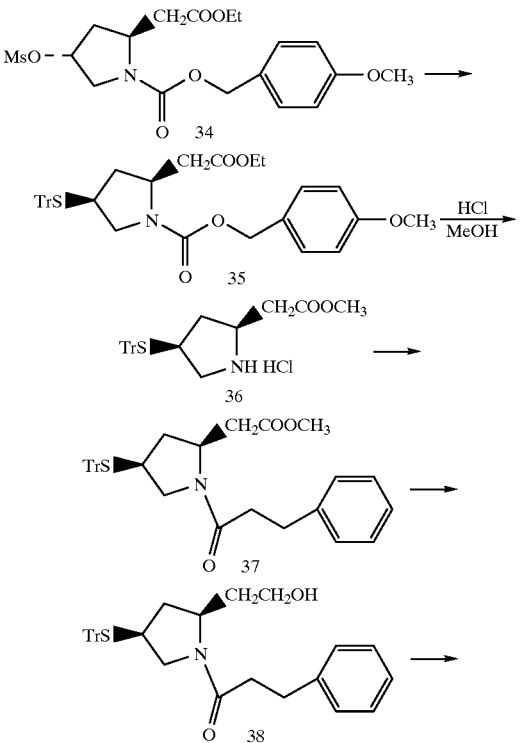

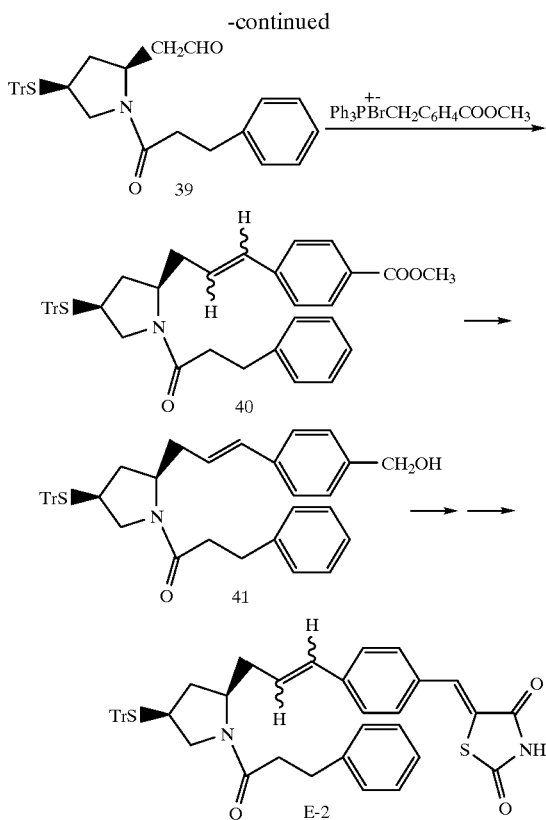

(1) 34→35

Under a nitrogen atmosphere, to a suspension of sodium hydride (1.129 g, 60%, 28.2 mmol) in dry tetrahydrofuran (26 ml) was added a solution of triphenylmethylmercaptane (8.4 g, 30.4 mmol) in tetrahydrofuran (26 ml) with stirring and under ice-cooling. After the addition of a solution of a starting compound (34) (9.02 g, 21.72 mmol) in tetrahydrofuran (26 ml), the mixture was stirred for 21 hr at room temperature. The reaction solution was poured into ice-water, extracted with ethyl acetate, washed with brine, dried over Na₂SO₄, and concentrated in vacuo. The resultant residue was subjected to silica gel column chromatography (eluting with hexane/ethyl acetate) to obtain the compound (35) (8.44 g, 65%).

NMR (CDCl₃): 1.23 (3H, t, J=7.0 Hz), 1.48–1.65 (1H, m), 2.37 (2H, q, J=7.0 Hz), 2.68–3.25 (4H, m), 3.78–3.96 (1H, m), 3.84 (3H, s), 4.05–4.15 (2H, m), 4.84–5.08 (2H, m), 6.80–6.95 (2H, m), 7.20–7.45 (17H, m).

(2) 35→36

The compound (36) was prepared in quantitative yield by treating the compound (35) (5.861 g, 9.84 mmol) in a manner similar to that used for the synthesis of the compound (30). The resultant compound (36) was dried by azeotropic distillation with dry toluene before subjecting to the synthesis of the compound (37).

(3) 36→37

The compound (36)(9.84 mmol) obtained in the above as a residue was treated in exactly the same manner as that for the synthesis of the compound (31) to give the compound (37) in 97% yield.

IR (CHCl₃): 1731,1631. NMR (CDCl₃): 1.52–1.68 (1H, m), 2.10–3.08 (10H, m), 3.65 (3H, s), 4.07–4.1 (1H, m), 7.12–7.47 (20H, m).

(4) 37→38

The foamy compound (37) (1.774 g, 3.23 mmol) obtained above reduced by treating in exactly the same manner as that for the synthesis of the compound (31) to give the compound (38) in 55% yield.

IR (CHCl₃): 3396,1616. NMR (CDCl₃): 1.43–1.58 (2H, m), 1.64–1.86 (1H, m), 2.13–2.21 (2H, m), 2.39–2.59 (2H, m), 2.67–2.83 (4H, m), 2.93 (1H, bs), 3.24–3.51 (2H, m), 4.23 (1H, bs), 7.12–7.45 (20H, m).

(5) 38→39

Under a nitrogen atmosphere, to a solution of dimethyl sulfoxide (371 µl, 5.23 mmol) in dry dichloromethane (1.2 ml) was added a solution of oxalyl chloride (227 µl, 2.6 mmol) in dichloromethane (3.6 ml) with stirring and under cooling −45° C. The mixture was stirred for 45 min at −45° C. After the addition of a solution of a starting compound (38) (961 mg, 1.84 mol) in dichloromethane (1.2 ml) over 10 min., the reaction mixture was stirred for 45 min at the same temperature. To the mixture was added a solution of triethylamine (1.28 ml, 9.2 mmol) in dichloromethane (1.2 ml), and the mixture allowed to stand overnight at room temperature. The reaction solution was washed with dilute hydrochloric acid, dried over Na₂SO₄, and concentrated in vacuo. The resultant residue was subjected to silica gel column chromatography (eluting with hexane/ethyl acetate) to obtain an aimed compound (690 mg). Yield 72%.

IR (CHCl₃): 1718,1629. NMR (CDCl₃): 1.41–1.61 (2H, m), 2.12–2.20 (2H, m), 2.32–2.82 (6H, m), 2.95–3.07 (1H, m), 4.06–4.20 (1H, m), 7.13–7.49 (20H, m), 9.69 (1H, s).

(6) 39→40

Under a nitrogen atmosphere, to a solution of a starting compound (312 mg, 0.6 mmol) obtained above in ethanol (7 ml) were added separately prepared methyl 4-(bromotriphenylphosphoniummethyl)benzoate (442 mg, 0.9 mmol) and triethylamine (251 µl, 1.8 mmol) with stirring. The mixture was heated to reflux for 14 hr. The reaction solution was poured into ice-water, extracted with ethyl acetate, washed with water, dried over Na₂SO₄, and concentrated in vacuo. The resultant residue was subjected to silica gel column chromatography (eluting with toluene/ethyl acetate) to obtain an aimed product as a mixture of E- and Z-compounds (269 mg). Yield 69%.

IR (CHCl₃): 1713,1628. NMR (CDCl₃): 1.40–1.69 (1H, m), 2.11–3.00 (10H, m), 3.91 (3H, s), 3.90–4.0 (1H, m), 5.51–5.64 & 6.07–6.22 & 6.40–6.55 (2H, m, E & Z mix), 7.15–7.49 (22H, m), 7.96–8.02 (2H, m).

(7) 40→41

The starting compound (40) (239 mg, 0.367 mmol) prepared in the above was reduced with lithium borohydride (80 mg, 10 mmol ) in exactly the same manner as that for the synthesis of the compounds (27, 34) to obtain the aimed product (41) (158 mg) as a mixture of E- and Z-compounds. Yield. 69%.

IR (CHCl₃): 3596,3408,1626. NMR (CDCl₃): 1.44–1.65 (1H, m), 2.09–2.95 (10H, m), 3.89–4.03 (1H, m), 4.67 (2H,s), 5.39–5.53 & 5.94–6.10 & 6.36–6.52 (2H, m, E & Z mix), 7.11–7.44 (24H, m).

The resultant compound (41) was then treated in a manner similar to that described in Example 1 to obtain an aimed compound E-2.

The compounds obtained in a manner similar to that described in Examples 7 and 8 are shown in Table E.

TABLE E

| | | IR (cm$^{-1}$) | NMR (CDCl$_3$ ppm) |
|---|---|---|---|
| E-1 | | 1742<br>1702<br>1619<br>1604 | 4.50(s, —CH$_2$—)<br>7.76(s, —CH=)<br>CHCl$_3$ |
| -2 | | 1743<br>1703<br>1622<br>1600 | 5.60(m, —CH=)<br>6.48(d, —CH=)<br>7.72(s, —CH=)<br>CHCl$_3$ |
| -3 | | 1740<br>1701<br>1619<br>1601 | 7.78(s, —CH=)<br>Nujol |
| -4 | | 1740<br>1700<br>1620<br>1600 | 5.13(s, —CH<)<br>7.79(s, —CH=)<br>Nujol |
| -5 | | 1739<br>1700<br>1596 | 3.72(s, —CH$_2$—)<br>7.56(s, —CH=)<br>Nujol |

EXAMPLE 9 (Method F)

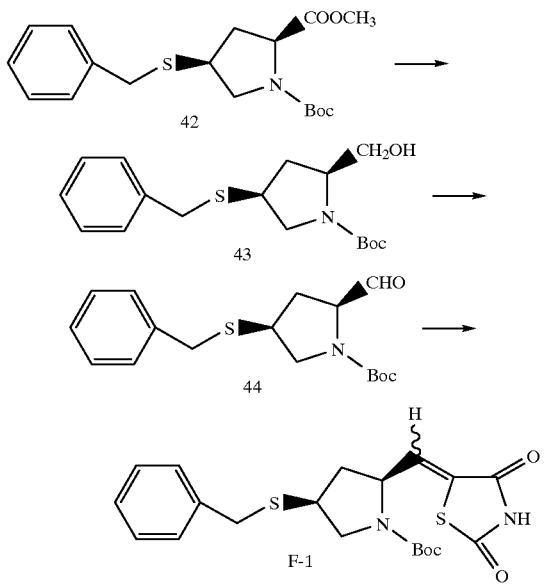

(1) 42→43

To a solution of methyl ester (632 mg, 180 mmol) in dry tetrahydrofuran (20 ml) was added lithium borohydride (59 mg, 1.5×1.8 mmol) with stirring and under ice-cooling. The mixture was stirred for 30 min at the same temperature and then for 4 hr at room temperature. To the reaction solution were added methanol (0.5 ml) and then ice-water (50 ml) under ice-cooling. After adjusting the pH to 2 with 10% HCl, and the reaction solution was extracted with ethyl acetate. The extract was washed with water, brine, dried over $Na_2SO_4$, and concentrated in vacuo. The residue was subjected to silica gel column chromatography and fractions eluting with hexane/ethyl acetate (2:1) were collected to obtain the alcohol (578 mg). Yield 99.3%.

NMR ($CDCl_3$): 1.44 (S, 9H), 2.30 (m, 1H), 3.01 (m, 1H), 3.63 (m, 3H), 3.76 (s, 2H), 3.90 (m, 1H), 4.80 (br. s, 1H), 7.31 (m, 5H).

(2) 43→44

To a solution of the alcohol (1.08 g) in dimethyl sulfoxide (2 ml) was added triethylamine (1.5 ml) under ice-cooling, followed by addition of a solution of sulfur trioxide-pyridine complex (1.63 g) in dimethyl sulfoxide (15 ml). The mixture was stirred for 20 min at room temperature, diluted with ethyl acetate (200 ml) for partition, washed with water and brine, dried over $Na_2SO_4$, and concentrated in vacuo. The residue was subjected to silica gel column chromatography and fractions eluting with hexane/ethyl acetate (2:1) were collected to obtain the aldehyde (607 mg). Yield 56.3%.

The starting compound was then recovered (33.4%).

Elemental analysis ($C_{17}H_{23}NO_3S$ $0.2H_2O$) Calcd.: C, 62.82; H, 7.26; N, 4.31; S, 9.86 Found: C, 62.99; H, 7.33; N, 4.34; S, 9.81. IR (Film): 1732,1696,1394,1255,1163, 1117. NMR($CDCl_3$) :1.44(s,9×5/8H),1.47(s,9×3/8H),2.12 (m,1H),2.37(m,1H), 3.18(m,1H),3.29(m,3/8H),3.42(d.d,J= 4.2,11.7 Hz,5/8H),3.56–3.77(m,3H),4.03(m,5/8H),4.14(m, 3/8H),7.22–7.37(m,5H), 9.61(d,J=2.1 Hz,5/8H), 9.66(d,J= 1.5 Hz,3/8H).

(3) 44→F-1

A mixture of aldehyde (570 mg), rhodanine (240 mg), 1M acetic acid (in toluene, 0.1 ml) and 1M piperidine (in toluene, 0.1 ml) in toluene (25 ml) was heated to reflux for 3 hr, and distilled under reduced pressure to remove the solvent. The resultant residue was subjected to silica gel column chromatography and fractions eluting with hexane/ ethyl acetate (2:1) were collected to obtain an aimed product (597 mg). Yield 77.1%.

Elemental analysis ($C_{20}H_{24}N_2O_3S_3$ $0.4H_2O$) Calcd.: C, 54.13; H, 5.63; N, 6.31; S, 21.67 Found: C, 54.17; H, 5.56; N, 6.36; S, 21.77 IR (KBr): 3439,1728,1699,1631,1392, 1207. NMR($CDCl_3$): 1.30–1.55 (m,9H), 1.71(m,1/2H), 1.95 (m,1/2H), 2.10 (m,1/2), 2.48(m,1/2H), 2.98–3.34(m,2H), 4.40–4.00 (m,1H) ,3.75 (s,1/2H), 3.76 (s,1/2H), 4.30–4.80 (m,1H), 6.76 (d,J=5.4 Hz,1/2H), 6.89 (d,J=6.1 Hz,1/2H), 7.31(m,5H), 9.60(br.s,1H).

The compounds obtained in a manner similar to that described in Example 9 above are shown in Table F.

TABLE F

| | $Y_1$—$Y_2$ | IR (KBr cm$^{-1}$) | NMR ($CDCl_3$ ppm) |
|---|---|---|---|
| F-1 | COO$^t$Bu | 1728 | 3.75(s, —CH$_2$— × 1/2) |
| | | 1699 | 3.76(s, —CH$_2$— × 1/2) |
| | | 1631 | 6.76(s, —CH= × 1/2) |
| | | | 6.89(s, —CH= × 1/2) |
| -2 | O$_2$S—⟨phenyl⟩—⟨phenyl⟩ | 1727 | 3.64(s, —CH$_2$— × 1/2) |
| | | 1630 | 3.66(s, —CH$_2$— × 1/2) |
| | | | 4.29(s, —CH= × 1/2) |
| | | | 4.43(s, —CH= × 1/2) |

EXAMPLE 10 (Method G)

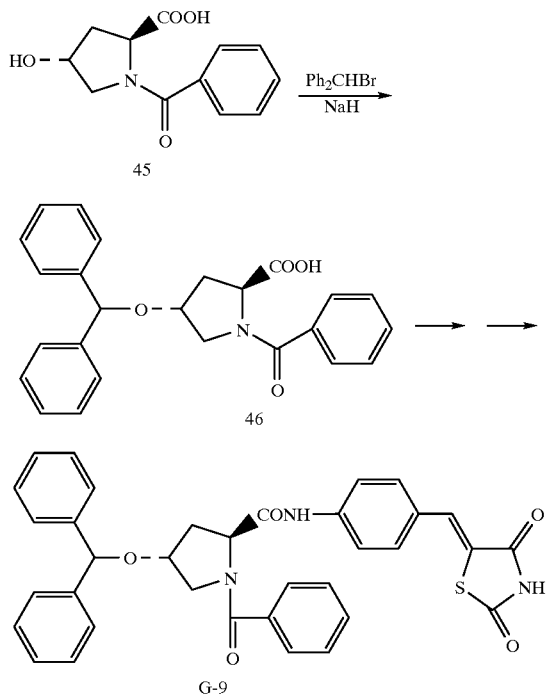

(1) 45→46

Under a nitrogen atmosphere, to a solution of a starting compound (5.34 g, 22.7 mmol) in dimethylformamide (23 ml) were added bromodiphenylmethane (6.73 g, 1.2×22.7 mmol), and then 60% sodium hydride (1.81 g, 2×22.7 mmol) under ice-cooling. The mixture was stirred overnight at room temperature. After the addition of water, the reaction mixture was washed with ethyl ether. The aqueous layer was acidified with 2N HCl in the presence of ethyl acetate for partition, washed with brine, dried over $Na_2SO_4$, and concentrated in vacuo. The residue was subjected to silica gel column chromatography and fractions eluting with methylene chloride/methanol (25:1) were collected to obtain an aimed product (3.97 g). Yield 43.6%.

NMR ($CDCl_3$): 2.46 (d.d, J=5.0,8.4 Hz, 2H), 3.58 (d.d, J=11.8,4.0 Hz, 1H), 3.71 (d, J=12.6 Hz, 1H), 4.18 (m, 1H), 4.45 (m, 1H), 4.96 (t, J=8.4 Hz, 1H), 5.30 (s, 1H), 7.13–7.54 (m, 15H).

The product above was treated in a manner similar to that described in Example 1 to yield the objective compound G-9.

The compounds obtained in a manner similar to that described in Example 10 above are shown in Table G.

TABLE G

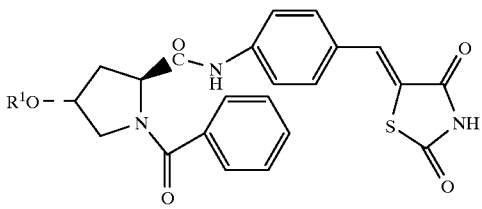

| | $R^1$ | IR ($CHCl_3$ ppm) | NMR ($CDCl_3$ ppm) |
|---|---|---|---|
| G-1 | H₂C⌬⌬ (geranyl) | 1739<br>1705<br>1615 | 1.58(s, $CH_3$)<br>1.59(s, $CH_3$)<br>1.66(s, $CH_3$) |
| -2 | $H_2C$—C₆H₄—F | 1739<br>1704<br>1615 | 4.32(d, 1H)<br>4,42(d, 1H) |
| -3 | $H_2C$—C₆H₄—Cl | 1738<br>1693<br>1608 | 4.35(d, 1H)<br>4.42(d, 1H) |
| -4 | $H_2C$—C₆H₄—$CF_3$ | 1748<br>1706<br>1615 | 4.47(d, 1H)<br>4.60(d, 1H) |

TABLE G-continued
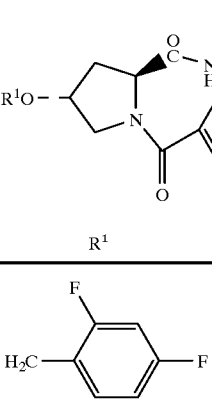
| | R¹ | IR (CHCl₃ ppm) | NMR (CDCl₃ ppm) |
|---|---|---|---|
| -5 | 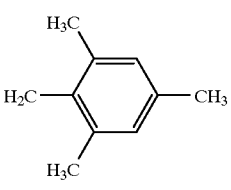 | 1739<br>1704<br>1620 | 4.38(d, 1H)<br>4.47(d, 1H) |
| -6 | 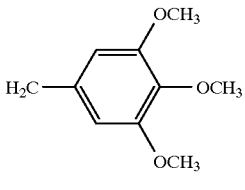 | 1747<br>1705<br>1614 | 2.20(s, CH₃)<br>2.24(s, CH₃ × 2)<br>4.33(d, 1H)<br>4.46(d, 1H) |
| -7 | 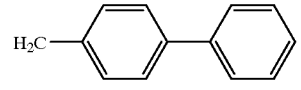 | 1747<br>1705<br>1614 | 3.81(s, CH₃)<br>3.82(s, CH₃ × 2)<br>4.33(d, 1H)<br>4.42(d, 1H) |
| -8 | 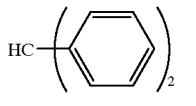 | 1745<br>1704<br>1589 | 4.39(d, 1H)<br>4.49(d, 1H) |
| -9 | 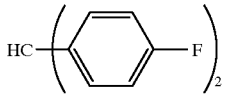 | 1748<br>1706<br>1601 | 5.34(s, 1H) |
| -10 | 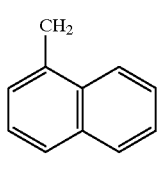 | 1746<br>1705<br>1600 | 5.28(s, 1H)<br>6.90(d, 1H)<br>6.99(d, 1H) |
| -11 | 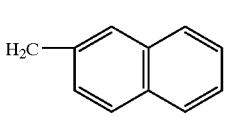 | 1745<br>1704<br>1589 | 4.80(d, 1H)<br>4.89(d, 1H) |
| -12 |  | 1742<br>1703<br>1618 | 4.48(d, 1H)<br>4.56(d, 1H) |

EXAMPLE 11 (Method H)

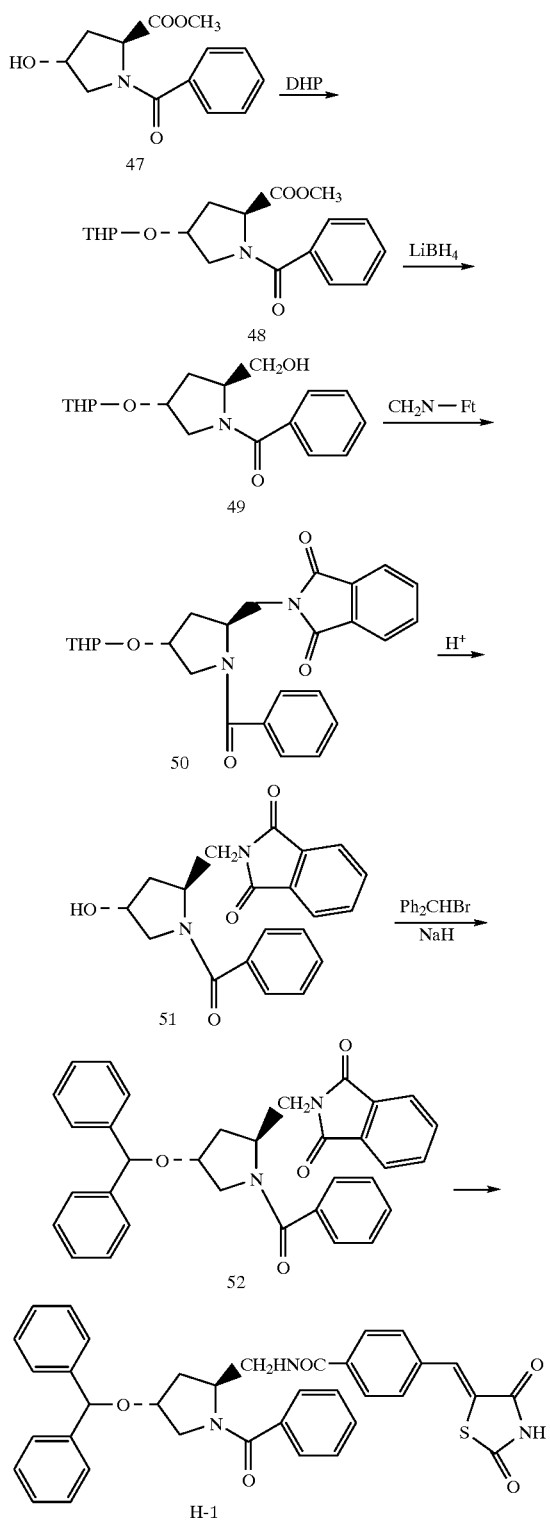

(1) 47→48

To a solution of methyl ester (20 g, 80.2 mmol) in methylene chloride (80 ml) were added 3,4-dihydro-2H-pyrane (8 ml, 1.1×80.2 mmol) and p-toluenesulfonic acid (0.3 g), and the mixture stirred for 7 hr at room temperature. After the addition of triethylamine (0.2 g), the mixture was washed with water, dried over Na$_2$SO$_4$, and concentrated in vacuo. The residue was subjected to silica gel column chromatography and fractions eluting with hexane/ethyl acetate (1:2) were collected to obtain an aimed product as a gum quantitatively.

NMR(CDCl$_3$): 1.35–1.90 (m, 6H), 2.14 (m, 1H), 2.46 (m, 1H), 3.30–3.90 (m, 4H), 3.79 (s, 3H), 4.36–4.87 (m, 3H), 7.35–7.90 (m, 5H).

(2) 48→49

To a solution of the ester in dry tetrahydrofuran (120 ml) was added lithium borohydride (2.62 g, 1.5×80.2 mmol) under ice-cooling. After stirring for 1 hr at room temperature, ethanol and 2N HCl were added under ice-cooling (pH=about 5). The mixture was extracted with ethyl acetate, washed with 5% NaHCO$_3$ and H$_2$O, successively, dried over Na$_2$SO$_4$, and concentrated in vacuo. The residue was subjected to silica gel column chromatography and fractions eluting with ethyl acetate were collected to obtain the aldehyde (22.86 g) as a gum. Yield 93.3%. A portion was lyophilized from benzene and subjected to the elemental analysis.

Elemental analysis (C$_{17}$H$_{23}$NO$_4$ 0.1C$_6$H$_6$) Calcd.: C, 67.50,; H, 7.60; N, 4.47 Found: C, 67.73; H, 7.69; N, 4.29. IR (CHCl$_3$): 3351br,1610,1602,1574. NMR(CDCl$_3$): 1.30–1.88 (m, 7H), 2.30 (m, 1H), 2.70 (m, 1H), 3.26–3.90 (m, 6H), 4.26 (m, 1H) 4.43–4.70 (m, 2H), 7.35–7.58 (m, 5H). (3) 49→50

Under a nitrogen atmosphere, to a solution of triphenylphosphine (24.13 g, 1.2×74.7 mmol) in dry tetrahydrofuran (150 ml) was added a solution of diisopropyl azodicarboxylate (16. 9ml, 1.15×74.7 mmol) in dry tetrahydrofuran (120 ml) at −78° C. over 15 min. To the mixture was then added a solution of phthalimide (12.64 g, 1.15×74.7 mmol) in dry tetrahydrofuran (250 ml) at −53° C. over 15 min. A solution of a starting compound (22.8 g, 74.7 mmol) in dry tetrahydrofuran (150 ml) was then added over 10 min and the mixture stirred for 1 hr at 0° C. and then overnight at room temperature. The reaction solution was concentrated in vacuo and flushed with toluene. The residue was subjected to silica gel column chromatography and fractions eluting with hexane/ethyl acetate (1:1) were collected to obtain an aimed product as an oil quantitatively.

Elemental analysis (C$_{25}$H$_{26}$N$_2$O$_5$) Calcd.: C, 69.11; H, 6.03; N, 6.45 Found: C, 69.36; H, 6.19; N, 6.44. IR (CHCl$_3$): 1774,1715,1629,1578.

(4) 50→51

To a solution of the previously prepared starting compound in methanol (150 ml) were added water (3 ml) and p-toluenesulfonic acid (1.42 g, 0.1×74.7 mmol), and the mixture stirred for 15 hr at room temperature. After the addition of triethylamine (1 ml), the reaction mixture was concentrated in vacuo. Water was added to the residue, followed by extraction with methylene chloride. The extract was washed with water, dried over Na$_2$SO$_4$, and concentrated in vacuo. The residue was subjected to silica gel column chromatography and fractions eluting with hexane/ethyl acetate (1:1) were collected and recrystallized from methylene chloride/ethyl ether to obtain an aimed product (22.94 g). mp. 180–181° C., yield 87.8% from compound 47.

Elemental analysis (C$_{20}$H$_{18}$ N$_2$O$_4$) Calcd.: C, 68.56; H, 5.18; N, 8.00 Found: C, 68.30; H, 5.34; N, 7.95. IR (Nujol): 3472,1774,1712,1610,1578. NMR (CDCl$_3$): 1.60–2.30 (m, 3H), 3.39 (d, J=10 Hz, 1H), 3.60 (d. d, J=10,4 Hz, 1H), 3.95 (d, J=6 Hz, 2H), 4.30 (s, 1H), 5.08 (m, 1H), 7.27–7.45 (m, 5H), 7.60–7.88 (m, 4H).

(5) 51→52

To a solution of a starting compound (4 g, 11.4 mmol) in dimethylformamide (20 ml) was added 60% sodium hydride (457 mg, 11.4 mmol), and the mixture stirred for 5 min under ice-cooling. After adding bromodiphenylmethane (2.96 g, 1.05×11.4 mmol), the mixture was stirred for 2 days at room temperature and then for 6 hr at 65° C. The reaction solution was poured into water/ethyl acetate for partition. The organic layer was washed with water and dried over $Na_2SO_4$ and concentrated in vacuo. The residue was subjected to silica gel column chromatography and fractions eluting with hexane/ethyl acetate (1:1) were collected to obtain an aimed product (1.857 g) as a foam. Yield 31.5%.

Elemental analysis ($C_{33}H_{28}N_2O_4$) Calcd.: C, 76.72; H, 5.46; N, 5.42 Found: C, 76.76; H, 5.64; N, 5.22. IR ($CHCl_3$): 1774,1725,1630,1603,1427. NMR ($CDCl_3$):1.88 (m, 1H), 2.34 (m, 1H), 3.50 (d, J=4 Hz, 2H), 3.93 (m, 2H), 4.08 (m, 1H), 5.04 (m, 1H), 5.18 (s, 1H), 7.05–7.40 (m, 15H), 7.60–7.87 (m, 4H).

(6) 52→H-1

A starting compound (1.8 g, 3.48 mmol) was treated in a manner similar to that described in Example 2 for the preparation of compound (18) from compound (17) to yield the amine. To a suspension of 4-(2,4-dioxothiazolidin-5-ylidenemethyl)benzoic acid (1.04 g, 1.2×3.48 mmol) in dimethylformamide (10 ml) were added water soluble carbodiimide hydrochloride (0.8 g, 1.2×3.48 mmol) and hydroxybenzotriazole (0.56 g, 1.2×3.48 mmol), and the mixture stirred for 30 min. After adding the amine in dimethylformamide (5 ml), the mixture was stirred overnight. The reaction solution was poured into water and extracted with methyl ethyl ketone. The extract was washed with water, dried over $Na_2SO_4$ and concentrated in vacuo. The residue was subjected to silica gel column chromatography, and fractions eluting with ethyl acetate were collected to yield an aimed product (879 mg) as a foam. Yield 40.9%.

Elemental analysis ($C_{36}H_{31}N_3O_5S$ $0.3H_2O$) Calcd.: C, 69.39; H, 5.11; N, 6.74; S, 5.15 Found: C, 69.43; H, 5.14; N, 6.58; S, 4.94. IR ($CHCl_3$): 3390,3323,1750,1709,1650,1610, 1533,1498. NMR ($CDCl_3$):1.84 (m, 1H), 2.53 (m, 1H), 3.35–3.95 (m, 4H), 4.10 (m, 1H), 4.82 (m, 1H), 5.24 (s, 1H), 7.10–7.55 (m, 18H), 7.74 (s, 1H), 7.94 (d, J=8 Hz, 2H), 8.76 (m, 1H).

The compounds prepared in a manner similar to those described above are shown in Table H.

TABLE H-1

|   | $Y_1-Y_2$ | $R^1$ | B | IR (Nujol cm$^{-1}$) | NMR (d-DMSO ppm) |
|---|---|---|---|---|---|
| H-1 | OC—Ph | HC—(Ph)$_2$ | O | 1750<br>1709<br>1650 | 5.24(s, —CH<)<br>7.74(s, —CH= × 3/4)<br>7.80(s, —CH= × 1/4)<br>CHCl$_3$<br>CDCl$_3$ |
| -2 | O$_2$S—CH$_2$—C$_6$H$_4$—Br | H$_2$C—C$_6$H$_3$F$_2$ | O | 1748<br>1707<br>1654 | 4.35(ABd, 1H)<br>4.41(ABd, 1H)<br>4.52(ABd, 1H)<br>4.55(ABd, 1H) |
| -3 | O$_2$S—CH$_2$—C$_6$H$_4$—CH$_3$ |  | O | 1749<br>1707<br>1655<br>1619 | 2.31(s, CH$_3$)<br>4.54(s, —CH$_2$—)<br>7.84(s, —CH=)<br>KBr |
| -4 | O$_2$S—C$_6$H$_4$—CH$_2$—Ph | CH$_3$ | O | 1748<br>1707<br>1654<br>1612 | 2.67(s, CH$_3$)<br>4.04(s, —CH$_2$—)<br>7.71(s, —CH=)<br>KBr |
| -5 |  | H$_2$C—C$_6$H$_3$F$_2$ | O | 1749<br>1709<br>1658<br>1620 | 3.94(s, —CH$_2$—)<br>4.02(ABd, 1H)<br>4.13(ABd, 1H)<br>7.84(s, —CH=)<br>KBr |
| -6 | COO$^t$Bu |  | O | 1743<br>1724<br>1665<br>1625 |  |
| -7 |  |  | S | 1733<br>1716 |  |

TABLE H-1-continued
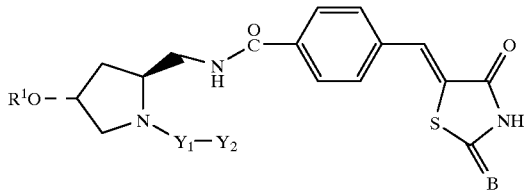
| Y₁-Y₂ | R¹ | B | IR (Nujol cm⁻¹) | NMR (d-DMSO ppm) |
|---|---|---|---|---|
| | | | 1666 | |
| | | | 1625 | |
TABLE H-2
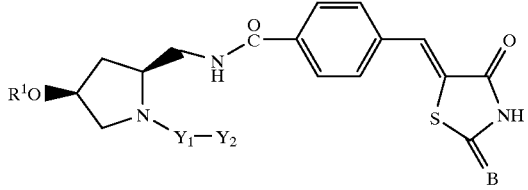
| | Y₁-Y₂ | R¹ | B | IR (Nujol cm⁻¹) | NMR (CDCl₃ ppm) |
|---|---|---|---|---|---|
| H-8 | 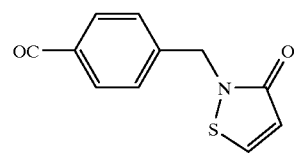 | 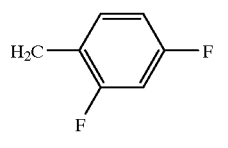 | O | 1746 1706 1619 1542 | 4.99(s, —CH₂—) 7.73(s, —CH=) |
| -9 | 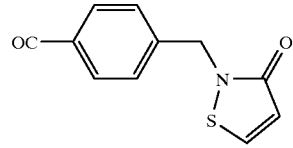 | 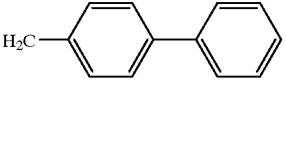 | O | 1746 1706 1612 1542 | 4.96(s, —CH₂—) 7.75(s, —CH=) |
| -10 | 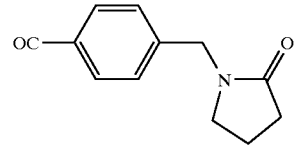 | 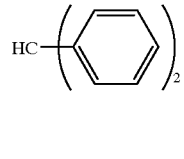 | O | 1745 1705 1637 1605 | 4.50(s, —CH₂—) 5.25(s, —CH<) 7.75(s, —CH=) KBr |
| -11 | 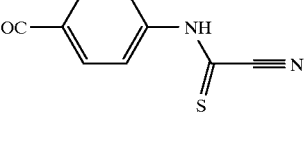 | 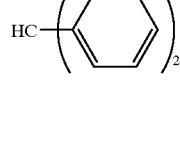 | O | 2230 1747 1698 1647 1610 | 5.48(s, —CH<) 7.82(s, —CH=) acetone KBr |
| -12 | 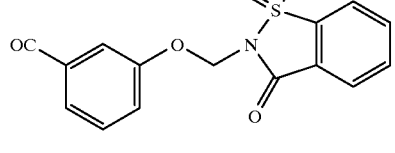 | 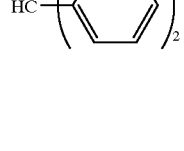 | O | 1746 1707 1607 | 5.26(s, —CH<) 5.74(ABd, —CH₂—) 5.78(ABd, —CH₂—) 7.75(s, —CH=) KBr |

TABLE H-2-continued
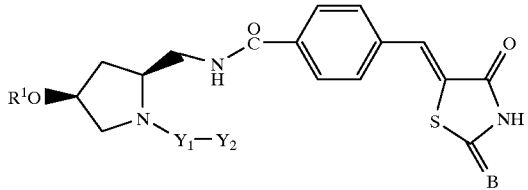
| Y₁–Y₂ | | R¹ | B | IR (Nujol cm⁻¹) | NMR (CDCl₃ ppm) |
|---|---|---|---|---|---|
| -13 | 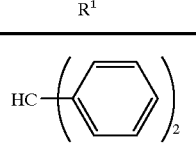 | 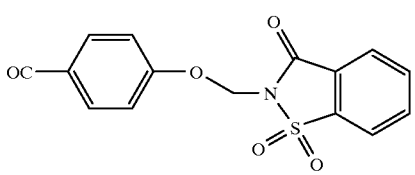 | O | 1747<br>1707<br>1610 | 5.24(s, —CH<)<br>5.86(s, —CH₂—)<br>7.71(s, —CH=)<br>KBr |
| -14 | 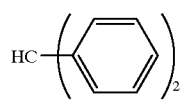 | 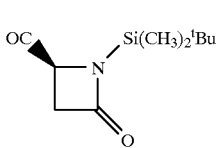 | O | 1750<br>1708<br>1646 | 0.14(s, —CH₃)<br>0.34(s, —CH₃)<br>1.01(s, —C(CH₃)₃)<br>5.43(s, —CH<)<br>7.81(s, —CH=)<br>KBr |
TABLE H-3
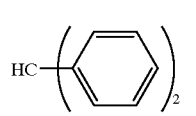
| | Y₁–Y₂ | R¹ | B | IR (KBr cm⁻¹) | NMR (CDCl₃ ppm) |
|---|---|---|---|---|---|
| H-15 | 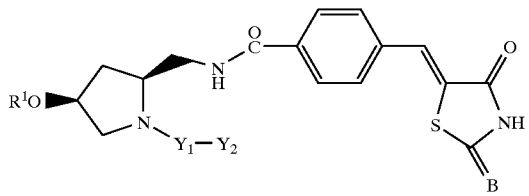 | 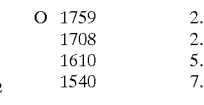 | O | 1759<br>1708<br>1610<br>1540 | 2.27(s, —CH₃)<br>2.28(s, —CH₃)<br>5.41(s, —CH<)<br>7.78(s, —CH=) |
| -16 | 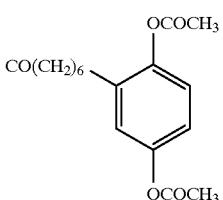 | 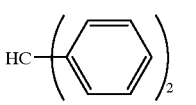 | O | 1752<br>1708<br>1610<br>1541 | 2.26(s, —CH₃)<br>5.41(s, —CH<)<br>7.75(s, —CH=) |
| -17 | 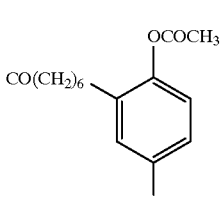 | 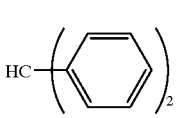 | O | 1748<br>1707<br>1655<br>1540 | 5.42(s, —CH<)<br>7.79(s, —CH=) |

TABLE H-3-continued

| Y₁–Y₂ | R¹ | B | IR (KBr cm⁻¹) | NMR (CDCl₃ ppm) |
|---|---|---|---|---|
| -18 CO(CH₂)₆-[naphthoquinone] | H₂C-[2,4-difluorophenyl] | O | 1749<br>1708<br>1662<br>1619 | 4.54(s, —CH₂—)<br>7.73(s, —CH=)<br>CHCl₃ |

TABLE H-4

| | Y₁–Y₂ | IR (KBr cm⁻¹) | NMR (ppm) |
|---|---|---|---|
| H-19 | O₂S-[CH₂-phenyl-Br] | | 4.30(ABd, 1H)<br>4.32(ABd, 1H)<br>4.38(ABd, 1H)<br>4.53(ABd, 1H)<br>7.83(—CH=)<br>d-DMSO |
| -20 | O₂S-[phenyl-CH₂-phenyl] | 1750<br>1710<br>1620<br>1605 | 3.92(s, —CH₂—)<br>4.04(ABd, 1H)<br>4.12(ABd, 1H)<br>7.85(s, —CH=)<br>CDCl₃ |

EXAMPLE 2 (Method I)

46 → → I-1

Compound I-1 having a hydroxymethyl group was prepared using the compound (46) described in Example 10 in a manner similar to that used for the preparation of compound (28). Physicochemical values of the compound I-1 and those obtained in a similar manner are shown in Table I

TABLE I

| | R¹ | IR (CHCl₃ cm⁻¹) | NMR (CDCl₃ ppm) |
|---|---|---|---|
| I-1 | HC-(phenyl)₂ | 1738<br>1700<br>1600<br>1532 | 4.37(m, 1H)<br>4.74(m, 1H)<br>5.14(m, —CH₂—) |

TABLE I-continued

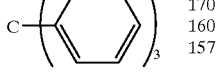

| R¹ | IR (CHCl₃ cm⁻¹) | NMR (CDCl₃ ppm) |
|---|---|---|
| -2 ![C(Ph)₃] | 1738<br>1700<br>1600<br>1578 | 4.50(m, 1H)<br>4.74(m, 1H) |

EXAMPLE 13 (Method J)

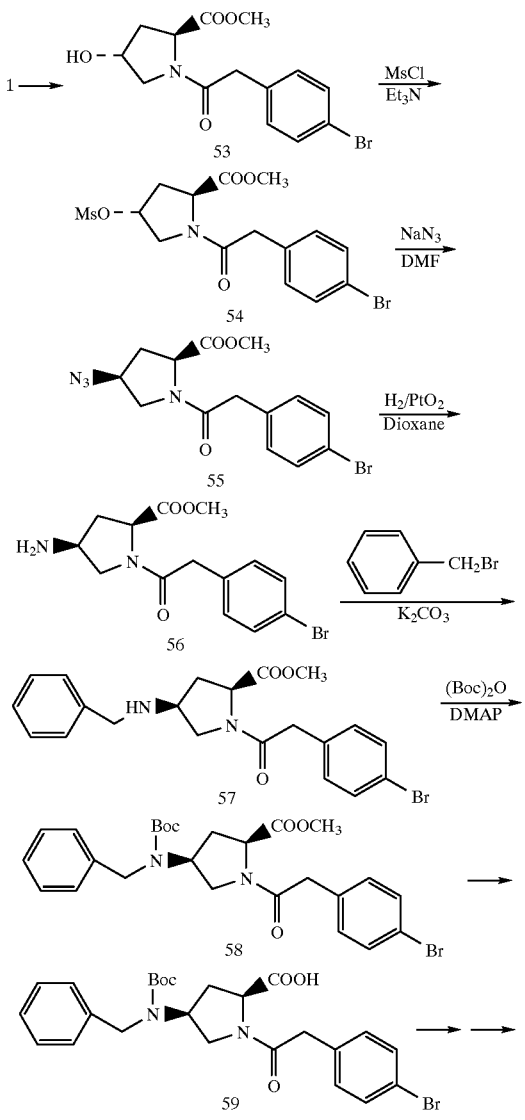

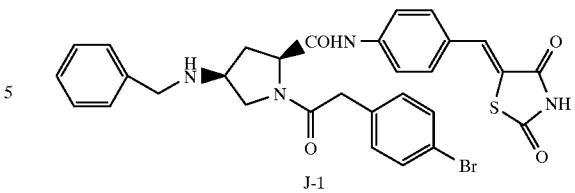

(1) 1→53

To a solution of 4-hydroxy-L-proline methyl ester hydrochloride (15.16 g, 83.47 mmol) in dichloromethane (448 ml) were added triethylamine (52.4 ml, 4.5×83.47 mmol), 4-bromo-p-phenylacetic acid (21.54 g, 1.2×83.47 mmol), and then 2-chloro-1,3-dimethylimidazolinium chloride (21.17 g, 1.5×83.47 mmol) under ice-cooling. The mixture was stirred for 10 min at the same temperature, then allowed to warm up to room temperature, stirred for 1 hr and 40 min, and poured into water/dichloromethane containing dil. HCl for partition. The dichloromethane layer was washed with water, saturated aqueous sodium bicarbonate, and water, dried over MgSO₄, and concentrated in vacuo. The residue was subjected to silica gel column chromatography and fractions eluting with ethyl acetate were collected and recrystallized from dichloromethane/ethyl ether to obtain prism-like crystals (15.74 g, mp. 135.0–136.0° C.). Yield 55.1%.

Elemental analysis ($C_{14}H_{16}BrNO_4$) Calcd.: C, 49.14; H, 4.71; N, 4.09 Br; 23.35 Found: C, 49.23; H, 4.73; N, 4.19 Br; 23.25. IR (CHCl₃): 3615,3440,1747,1650,1596,1490,1419, 1403. NMR (CDCl₃): 1.94–2.12 (m, 1H), 2.14–2.33 (m, 1H), 2.55 (d, J=4 Hz, 1H), 3.42–3.87 (m, 2H), 3.62 (s, 2H), 3.72 (s, 3H), 4.39–4.60 (m, 1H), 4.58 (t, J=8 Hz, 1H), 7.14 (d, J=8 Hz, 2H), 7.44 (d, J=8 Hz, 2H).

(2) 53→54

To a solution of 4-hydroxyproline derivative (53) (16.326 g, 47.71 mmol) in dichloromethane (56 ml) were added triethylamine (8.65 ml, 1.3×47.71 mmol), and then methanesulfonyl chloride (4.06 ml, 1.1×47.71 mmol) under ice-cooling. After stirring for 1 hr at the same temperature, the reaction solution was poured into water/dichloromethane containing dil. HCl for partition. The dichloromethane layer was washed with water, saturated aqueous sodium bicarbonate and water, dried over Na₂SO₄ and concentrated in vacuo. The residue was subjected to silica gel column chromatography and fractions eluting with toluene/ethyl acetate (1:1) were collected to obtain a mesylated compound (19.98 g). Yield 99.6%. A portion was lyophilized from benzene and subjected to elemental analysis.

Elemental analysis ($C_{15}H_{18}BrNO_6S$ 0.1$C_6H_6$) Calcd.: C, 43.77; H, 4.38; N, 3.27; Br, 18.67; S, 7.49 Found: C, 44.03; H, 4.49; N, 3.47; Br, 19.08; S, 7.50. IR (CHCl₃): 1748,1658, 1598,1490,1427. NMR (CDCl₃):2.13–2.32 (m, 1H), 2.48–2.66 (m, 1H), 3.00 (s, 3H), 3.50–3.94 (m, 2H), 3.65 (s, 2H), 3.75 (s, 3H), 4.62 (t, J=8 Hz), 5.22–5.36 (m, 1H), 7.15 (d, J=8 Hz, 2H), 7.46 (d, J=8 Hz, 2H).

(3) 54→55

To a solution of the mesylate (19.81 g, 47.14 mmol) in dimethylformamide (154 ml) was added sodium azide (9.19 g, 3×47.14 mmol). The mixture was heated at 60 ° C. with stirring for 9 hr, and poured into water/ethyl acetate for partition. The organic layer was washed with water (×2) and brine, dried over MgSO₄ and concentrated in vacuo to obtain an azide compound (17.08 g, oil). Yield 98.7%.

IR (CHCl₃): 2102,1747,1652,1593,1487,1424. NMR (CDCl₃): 2.10–2.25 (m, 1H), 2.37–2.57 (m, 1H), 3.44–3.86 (m, 2H), 3.65 (s, 2H), 3.75 (s, 3H), 4.15–4.29 (m, 1H), 4.48

(d.d, J1=8 Hz, J2=2 Hz, 0.3H), 4.63 (d.d, J1=9 Hz, J2=5 Hz, 0.7H), 7.17 (d, J=9 Hz, 2H), 7.46 (d, J=9 Hz, 2H).

(4) 55→56

To a solution of the azide compound (16.61 g, 45.23 mmol) in dioxane (220 ml) was added platinum oxide (2 g), and catalytic reduction was carried out. The reaction solution was filtered and concentrated in vacuo to yield an amine (18.97 g) as a syrup.

IR (CHCl$_3$): 3372,1742,1646,1487,1434. NMR (CDCl$_3$): 1.70–1,94 (m, 3H), 2.31–2.53 (m, 1H), 3.34 (d.d, J1=10 Hz, J2=4 Hz, 1H), 3.46–3,80 (m, 2H), 3.64 (s, 2H), 3.75 (s, 3H), 4.38–4.53 (m, 1H), 7.16 (d, J=8 Hz, 2H), 7.45 (d, J=8 Hz, 2H).

(5) 56→57

To a solution of the amine (18.97 g, 45.23 mmol) in acetonitrile (222 ml) were added potassium carbonate (9.38 g, 1.5×45.23 mmol) and then benzyl bromide (5.92 ml, 1.1×45.23 mmol) under ice-cooling. The mixture was stirred for 10 min at the same temperature, warmed up to room temperature and stirred for 16 hr. The reaction solution was filtered, washed with dichloromethane, and concentrated in vacuo. The residue was poured into water/ethyl acetate for partition. The organic layer was washed with brine, dried over MgSO$_4$ and concentrated in vacuo. The residue was subjected to silica gel column chromatography and fractions eluting with toluene/ethyl acetate (1:1 to ethyl acetate) were collected to obtain an N-benzyl compound (10.654 g, yield 54.6%) as an oil.

IR (CHCl$_3$): 3320,1741,1646,1488,1434. NMR (CDCl$_3$); 1.86–2.06 (m, 1H), 2.28–2.48 (m, 1H), 3.30–3.50 (m, 2H), 3.51–3.80 (m, 3H), 3.61 (s, 2H), 3.72 (s, 3H), 4.37–4.53 (m, 1H), 7.14 (d, J=9 Hz, 2H), 7.42 (d, J=9 Hz, 2H), 7.20–7.39 (m, 5H).

(6) 5→58

To a solution of the N-benzyl compound (10.782 g, 25.00 mol) in dichloromethane were added di-t-butyl dicarbonate (12.42 g, 2.2×25.00 mmol) and then 4-dimethylaminopyridine (640 mg, 0.4×25.00 mmol) under ice-cooling. The mixture was stirred for 10 min at the same temperature, then warmed up to room temperature and stirred for 22 hr. The reaction solution was poured into water/dichloromethane containing dil. HCl for partition. The dichloromethane layer was washed with water, saturated aqueous sodium bicarbonate, and water, dried over MgSO$_4$ and concentrated in vacuo. The residue was subjected to silica gel column chromatography and fractions eluting with toluene/ethyl acetate (3:1) were collected to obtain a Boc-compound as a foam (5.412 g). Yield 42.7%.

IR (CHCl$_3$): 1792,1744,1684,1648,1489,1474,1450, 1426. NMR (CDCl$_3$): 1.47 (S, 9H), 1.88–2.14 (m, 1H), 2.22–2.50 (m, 1H), 3.24–3.75 (m, 3H), 3.54 (s, 2H), 3.70 (s, 3H), 4.23–4.55 (m, 1H), 4.40 (s, 2H), 7.03 (d, J=9 Hz, 2H) 7.41 (d, J=9 Hz, 2H), 6.98–7.35 (m, 5H).

(7) 58→59

To a solution of methyl ester (5.410 g, 10.180 mmol) in methyl alcohol (67 ml) was added 1 N potassium hydroxide aqueous solution (20.3 ml, 2×10.180 mmol) and the mixture stirred for 2 hr and 35 min at room temperature. The reaction solution was poured into water/ethyl ether for partition. The ethyl ether layer was washed with water. Aqueous layers were combined and poured into water/ethyl acetate containing dil. HCl for partition. The organic layer was washed with water, dried over MgSO$_4$ and concentrated in vacuo to obtain a carboxylic acid (4.434 g) as a foam. Yield 84.2%.

IR (CHCl$_3$): 3350,2600,1728,1683,1647,1487,1474, 1451,1417,1392. NMR (CDCl$_3$): 1.41 (s, 9H), 2.10–2.45 (m, 2H), 3.29 (t, J=10 Hz, 1H), 3.40–3.72 (m, 1H), 3.56 (s, 2H), 4.24–4.56 (m, 4H), 5.40–6.00 (m, 1H), 7.03 (d, J=9 Hz, 2H), 7.39 (d, J=9 Hz, 2H), 7.07–7.19 (m, 2H), 7.21–7.35 (m, 3H).

The product was treated in a manner similar to those described in the Examples above to yield thiazolidinedione derivative (J-1). The Physicochemical values of the compound (J-1) are shown in Table below.

TABLE J

| IR (CHCl$_3$ cm$^{-1}$) | NMR (CDCl$_3$ ppm) |
|---|---|
| 1738 | 4.60(m, 1H) |
| 1702 | 4.73(d, 1H) |
| 1632 | |
| 1590 | |

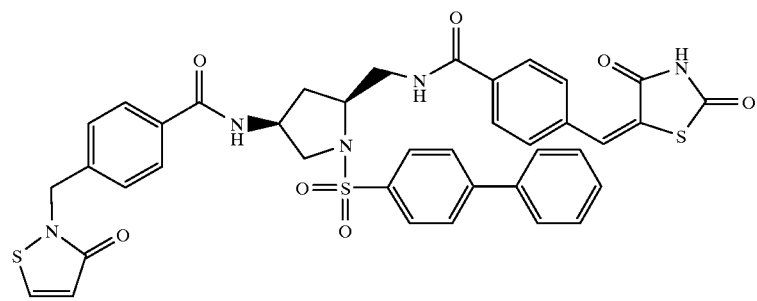

TABLE J-continued

| IR (Nujol cm$^{-1}$) | NMR (DMSO ppm) |
|---|---|
| 1739 | 4.92(s, —CH$_2$—) |
| 1701 | 7.26(s, —CH=) |
| 1626 | 10.42(s, NH) |

EXAMPLE 14 (Method K)

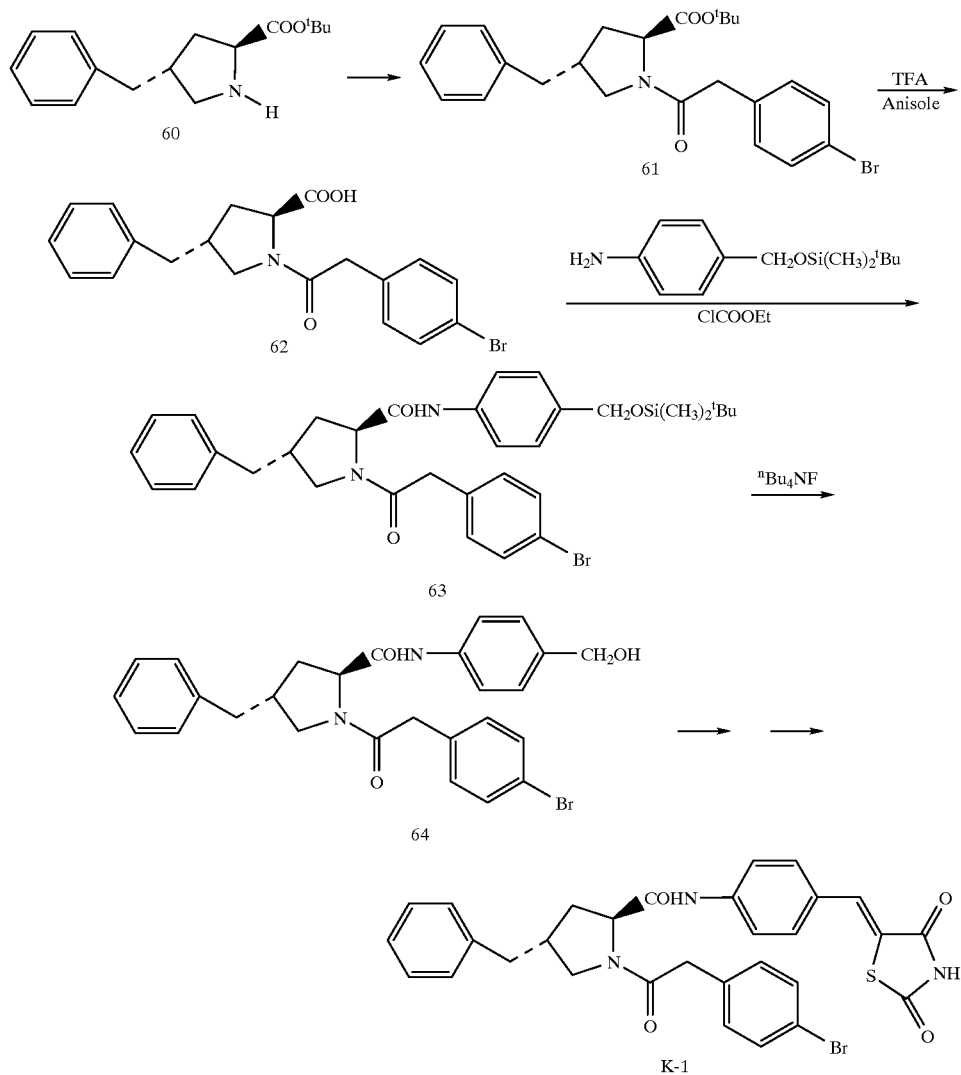

(1) 60→61

To a solution of the starting compound (0.39 g, 1.49 mmol), which is described in a literature (D. K. Diksihit and S. K. Panday, J. Org. Chem., 1992,57,1927), in methylene chloride (5 ml) were added triethylamine (0.62 ml, 4.48 mmol) and 4-bromophenylacetic acid (0.35 g, 1.63 mmol). To the mixture was added 2-chloro-1,3-dimethylimidazolinium chloride (0.38 g, 2.24 mmol) with stirring and under ice-cooling. After stirring for 1 hr at room temperature, the mixture was poured into ice-cold water, followed by extraction with ethyl acetate. The organic layer was washed with 1N HCl, saturated aqueous solution of NaHCO$_3$, brine, successively, dried over anhydrous Na$_2$SO$_4$, and concentrated in vacuo. The residue was purified with silica gel column chromatography (toluene/ethyl acetate, 85:15) to obtain an aimed product (0.52 g). Yield 76%.

Elemental analysis (C$_{24}$H$_{28}$BrNO$_3$) Calcd.: C, 62.89; H, 6.16; N, 3.06 Found: C, 63.06; H, 6.24; N, 3.16 NMR (CDCl$_3$): 1.43 (s, 9H), 1.97 (m, 2H), 2.62 (m, 3H), 3.15 (m, 1H), 3.58 (s, 2H), 3.63 (m, 1H), 4.43 (dd, 1H, J=4.0,8.6 Hz), 7.01–7.50 (m, 9H).

(2) 61→62

To a solution of a starting compound (0.52 g, 1.13 mmol) in methylene chloride were added anisole (0.62 ml, 5.71 mmol) and trifluoroacetic acid (0.85 ml, 11.4 mmol) and the mixture allowed to stand overnight at room temperature. Under ice-cooling, the reaction mixture was combined with aqueous solution of $NaHCO_3$ and concentrated. The residue was extracted with ethyl acetate. The extract was washed with brine, dried over anhydrous $Na_2SO_4$, and concentrated in vacuo. The residue was subjected to silica gel column chromatography and fractions eluting with chloroform/methanol/acetic acid (94:6:0.1) were collected to obtain an aimed product (0.44 g).

Elemental analysis ($C_{24}H_{28}BrNO_3$) Calcd.: C, 62.89; H, 6.16; N, 3.06 Found: C, 63.06; H, 6.24; N, 3.16. NMR ($CDCl_3$): 1.81 (m, 1H), 2.46 (m, 1H), 2.70 (m, 3H), 3.17 (m, 1H), 3.61 (m, 1H), 3.63 (s, 2H), 4.65 (d, 1H, J=7.2 Hz), 7.10–7.51 (m, 9H).

(3) 62→63

Under a nitrogen atmosphere, to a solution of a starting compound (0.45 g, 1.11 mmol) and triethylamine (0.37 ml, 2.68 mmol) in methylene chloride (5 ml) was added ethyl chlorocarbonate (0.19 ml, 2.0 mmol) under ice-cooling, and the mixture stirred for 1 hr. After the addition of a solution of 4-(dimethyl-t-butylsilyloxymethyl)aniline (0.32 g, 1.33 mmol) in methylene chloride (1 ml), the mixture was stirred for 3 hr under ice-cooling . To the reaction mixture was added water, followed by extraction with ethyl acetate. The organic layer was washed with 1N HCl, saturated aqueous $NaHCO_3$ and brine, successively, dried over $Na_2SO_4$, and concentrated. The residue was subjected to silica gel column chromatography and the fractions eluting with ethyl acetate/toluene (2:8) were collected to yield an aimed product (0.59 g). Yield 86%.

Elemental Analysis ($C_{33}H_{41}BrN_2O_3Si$ $0.5H_2O$) Calcd.: C, 62.85; H, 6.71; N, 4.44 Found: C, 62.77; H, 6.61; N, 4.61. NMR ($CDCl_3$); 0.07 (s, 6H), 0.92 (s, 9H), 1.60 (m, 1H), 2.65 (m, 1H), 2.86 (m, 2H), 3.15 (t, 1H, J=9.0 Hz), 3.55 (m, 1H), 3.61 (s, 2H), 4.68 (s, 2H), 4.82 (d, 1H, J=7.8 Hz), 7.07–7.50 (m, 13H), 9.43(s, 1H).

(4) 63→64

To a solution of a starting compound (0.27 g, 0.434 mmol) in tetrahydrofuran (3 ml) was added 1M tetrabutylammonium fluoride in tetrahydrofuran (0.434 ml, 0.434 mmol), and the mixture allowed to stand overnight. The mixture was concentrated in vacuo and extracted with ethyl acetate. The extract was washed with brine, dried over anhydrous $Na_2SO_4$, and concentrated in vacuo. The residue was subjected to silica gel column chromatography and the fractions eluting with ethyl acetate/toluene (6:4) were collected to yield an aimed product (0.15 g). Yield 67%.

NMR ($CDCl_3$): 1.60 (m, 1H), 2.63 (m, 2H), 2.84 (m, 2H), 3.16 (t, 1H, J=9.4), 3.59 (m, 1H), 3.61 (s, 2H), 4.62 (s, 2H), 4.82 (d, J=7.8 Hz, 1H), 7.08–7.50 (m, 13H), 9.51 (s, 1H).

The thiazolidinedione derivative(K-1) was then prepared in a manner similar to that described in preceding Examples. Physicochemical values thereof are shown in Table below.

TABLE K

K-1

| IR ($CHCl_3$ cm$^{-1}$) | NMR ($CDCl_3$ ppm) |
|---|---|
| 1743 | 3.63(s, —$CH_2$—) |
| 1704 | 7.70(s, —CH=) |
| 1629 | |
| 1586 | |

EXAMPLE 15 (Method L)

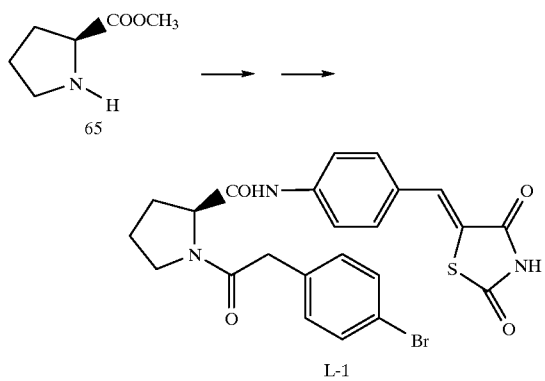

Compounds having proline ring instead of pyrrolidine were prepared in a manner similar to that described in preceding Examples. Physicochemical values thereof are shown in Table L.

TABLE L

| | B | IR (Nujol cm$^{-1}$) | NMR ($CDCl_3$ ppm) |
|---|---|---|---|
| L-1 | S | 1700 | 3.72(s, —$CH_2$— |
| | | 1584 | 7.91(s, —CH=) |
| | | 1530 | |
| -2 | O | 1746 | 3.71(s, —$CH_2$—) |
| | | 1700 | 7.70(s, —CH=) |
| | | 1678 | |

EXAMPLE 16 (Method M)

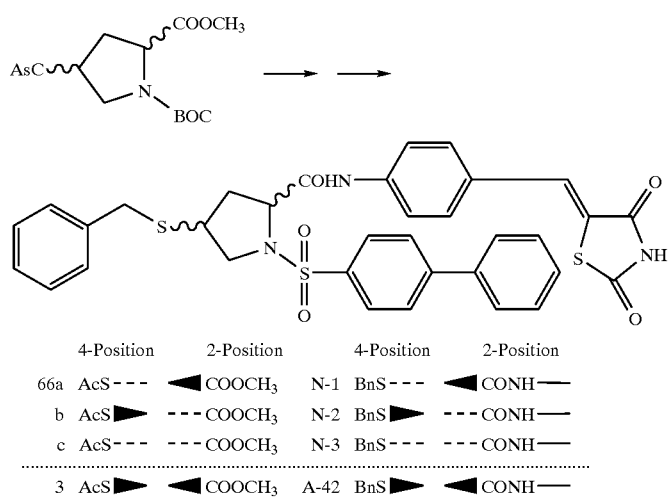

| | 4-Position | 2-Position | | 4-Position | 2-Position |
|---|---|---|---|---|---|
| 66a | AcS--- | ◀COOCH₃ | N-1 | BnS--- | ◀CONH— |
| b | AcS▶ | ---COOCH₃ | N-2 | BnS▶ | ---CONH— |
| c | AcS--- | ---COOCH₃ | N-3 | BnS--- | ---CONH— |
| 3 | AcS▶ | ◀COOCH₃ | A-42 | BnS▶ | ◀CONH— |

In this Example, three kinds of compound, which correspond to Compound A-42, with different configuration at 2- and 4-positions of pyrrolidine ring were prepared in a manner similar to that described in preceding Examples using a starting compound known in Japanese Patent Publication (KOKAI) No. 294970/1993 (U.S. Pat. No. 5317016). Physicochemical values of the resultant compounds are shown in Table M.

TABLE M

| | Position | | IR(Nujol cm⁻¹) | NMR(CDCl₃ ppm) |
|---|---|---|---|---|
| | 2 | 4 | | |
| M-1 | 2β | 4α | 3361 1599 | 3.68(s, —CH2—) |
| | | | 3145 | 7.82(s, —CH=) |
| | | | 1758 | |
| | | | 1685 | |
| -2 | 2α | 4β | 3360 1598 | 3.69(s, —CH2—) |
| | | | 3139 br | 7.82(s, —CH=) |
| | | | 1751 | |
| | | | 1685 | |
| -3 | 2α | 4α | 3550 1588 | 3.68(s, —CH2—) |
| | | | 1750 | 7.82(s, —CH=) |
| | | | 1697 | |
| | | | 1664 | |

EXAMPLE 17 (Method N)

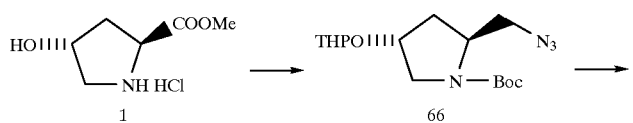

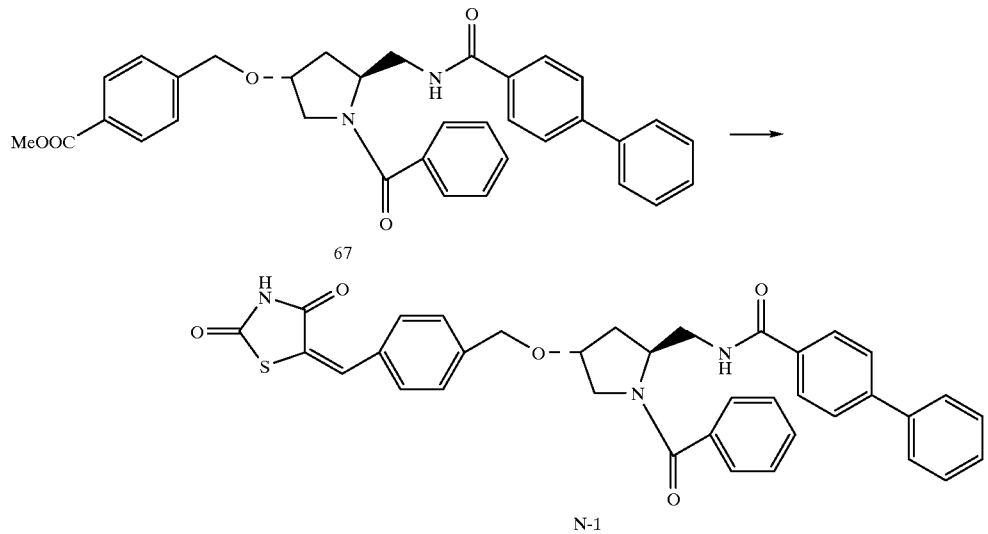

The compound (66) was prepared using the compound (1) as a starting material in accordance with the method described in preceding Examples. The compound (66) was then converted into compound (67) in accordance with the procedures described in preceding Examples, which involve the steps: etherification at the 4-position; reduction at the 2-position; amidation; deprotection at the 1-position; and amidation. The compound (67) was treated in a manner similar to that described in Examples above to yield the compound N-1.

TABLE N-1

| IR (KB r cm$^{-1}$) | NMR (CDCl$_3$ ppm) |
|---|---|
| 1743 | 4.39(ABd, —CH$_2$—) |
| 1705 | 4.49(ABd, —CH$_2$—) |
| 1608 | 7.81(s, —CH=) |

| | Z | R$^1$ | Y$_1$-Y$_2$ |
|---|---|---|---|
| N-2 | CH$_2$NHCO | —⟨C$_6$H$_4$⟩—(CH$_2$)$_3$CH$_3$ | CO—⟨C$_6$H$_5$⟩ |

TABLE N-1-continued

| | | | |
|---|---|---|---|
| N-3 | —C₆H₄ (phenyl) | | CO—C₆H₄—(CH₂)₃CH₃ |
| N-4 | —C₆H₄—C₆H₅ (biphenyl) | | SO₂—C₆H₄—C₆H₅ |
| N-5 | —C₆H₄—CH₃ | | CONH(CH₂)₃CH₃ |
| N-6 | —(CH₂)₃CH₃ | | SO₂—C₆H₄—OCH₃ |
| N-7 | —C₆H₄—OCH₃ | | SO₂(CH₂)₃CH₃ |

Compounds prepared in Examples above were tested for the $cPLA_2$ inhibitory activity in a manner shown in the following experimental example.

Experiment 1 $cPLA_2$ Inhibitory activity

The compounds of the present invention was tested for the $cPLA_2$ inhibitory activity by a method known in a literature (R. M. Kramer, E. F. Roberts, J. Manetta and J. E. Putnam, J. Biol. Chem., 268(8), 5268–5272 (1991)), as outlined below.

As a substrate, liposomes which contain 1-palmitoyl-2-[$^{14}$C]-arachidonoyl-sn-glycero-3-phosphocholine and sn-1, 2-dioleoylglycerol at the ratio of 2:1 and have treated ultrasonically were used. The substrate was added to a 50 mM HEPES buffer (pH 7.4) (200 μl) containing 1 mM $CaCl_2$, 2 mM dithiothreitol, 150 mM NaCl, 0.1 mg/ml BSA so as to make the concentration of radio-labeled phosphatidylcholine 2.5 μM. To the solution was added a compound of the present invention in DMSO (10 μl) to obtain reaction solutions each containing the test compound at 250 μM, 50 μM, 10 μm, 2 μM, and 0.4 μM. The reaction was allowed to start by adding an enzyme ($cPLA_2$) (4 ng) and continued for 15 min at 37° C.

The amount of fatty acids released by the reaction was measured on a liquid scintillation counter. Control was obtained by conducting the experiment in the same manner except that a compound of the present invention was not added. The inhibitory activity was expressed as percent (%) to the control value, which was used for the calculation of the concentration required for 50% inhibition ($IC_{50}$, μM). The results are shown in Table P.

TABLE P cPLA₂ Inhibition Activity

| Compound No. | IC₅₀ (μM) | Compound No. | IC₅₀ (μM) | Compound No. | IC₅₀ (μM) |
|---|---|---|---|---|---|
| A-2 | 7.2 | A-22 | 21 | A-42 | 14 |
| A-3 | 5.3 | A-23 | 10 | A-43 | 6.8 |

TABLE P-continued cPLA₂ Inhibition Activity

| Compound No. | IC₅₀ (μM) | Compound No. | IC₅₀ (μM) | Compound No. | IC₅₀ (μM) |
|---|---|---|---|---|---|
| A-4 | 1.6 | A-24 | 9.2 | A-44 | 7.4 |
| A-5 | 3.6 | A-25 | 18 | A-45 | 4.8 |
| A-6 | 3.3 | A-26 | 2.8 | A-46 | 7.0 |
| A-7 | 5.3 | A-27 | 5.1 | A-47 | 6.0 |
| A-8 | 4.8 | A-28 | 8.3 | A-48 | 4.9 |
| A-9 | 5.1 | A-29 | 5.9 | A-49 | 17 |
| A-10 | 3.8 | A-30 | 16 | A-50 | 12 |
| A-11 | 4.7 | A-31 | 4.8 | A-51 | 6.3 |
| A-12 | 1.3 | A-32 | 4.8 | A-52 | 5.6 |
| A-13 | 20 | A-33 | 6.4 | A-54 | 3.4 |
| A-14 | 18 | A-34 | 6.3 | A-55 | 3.4 |
| A-15 | 15 | A-35 | 1.9 | A-56 | 1.9 |
| A-16 | 22 | A-36 | 14 | A-57 | 4.7 |
| A-17 | 6.0 | A-37 | 1.6 | A-58 | 5.1 |
| A-18 | 16 | A-38 | 6.4 | A-59 | 8.6 |
| A-19 | 4.3 | A-39 | 6.2 | A-60 | 6.1 |
| A-20 | 22 | A-40 | 15 | A-61 | 1.6 |
| A-21 | 18 | A-41 | 3.4 | A-62 | 4.3 |
| | | | | A-63 | 3.2 |
| B-1 | 0.82 | E-1 | 1.1 | H-1 | 6.7 |
| B-2 | 2.9 | E-2 | 0.46 | H-2 | 8.1 |
| B-3 | 1.2 | E-3 | 0.85 | H-3 | 14 |
| B-4 | 2.4 | E-4 | 3.7 | H-4 | 26 |
| B-5 | 2.2 | E-5 | 7.7 | H-5 | 6.4 |
| B-6 | 31 | F-2 | 10 | H-6 | 1.7 |
| B-7 | 9.7 | G-1 | 9.0 | H-7 | 11 |
| B-8 | 1.3 | G-2 | 20 | H-8 | 3.2 |
| B-9 | 0.44 | G-3 | 17 | H-9 | 2.0 |
| C-1 | 30 | G-4 | 14 | H-10 | 10 |
| C-2 | 25 | G-5 | 21 | H-11 | 4.3 |
| C-3 | 16 | G-6 | 10 | H-12 | 6.2 |
| C-4 | 3.2 | G-8 | 5.6 | H-13 | 4.4 |
| C-5 | 9.8 | G-9 | 4.2 | H-14 | 8.2 |
| C-6 | 13 | G-10 | 6.0 | H-15 | 11 |
| D-1 | 22 | G-10 | 6.0 | H-16 | 4.3 |
| D-2 | 7.0 | G-11 | 8.5 | H-17 | 4.9 |
| | | G-12 | 9.9 | H-18 | 11 |
| | | | | H-19 | 8.6 |
| I-1 | 26 | | | H-20 | 6.6 |

TABLE P-continued cPLA₂ Inhibition Activity

| Compound No. | IC$_{50}$ (μM) | Compound No. | IC$_{50}$ (μM) | Compound No. | IC$_{50}$ (μM) |
|---|---|---|---|---|---|
| I-2 | 3.5 | | | | |
| J-1 | 21 | | | | |
| J-2 | 2.9 | | | | |
| L-1 | 5.3 | | | | |
| M-1 | 23 | | | | |
| M-2 | 15 | | | | |
| M-3 | 10 | | | | |
| N-1 | 6.6 | | | | |

Experiment 2 Inhibition of Production of Prostaglandin E$_2$ in Human Fibroblasts Proliferation of fibroblasts has been observed in lesion sites of patients suffering from rheumatoid arthritis, indicating that prostaglandins produced by fibroblasts, under the stimulation of inflammatory cytokines such as TNF or IL-1, could participate in the progress of the pathological conditions of disease. From this viewpoint, the compounds of the present invention were tested for the effect on the production of prostaglandin E$_2$ by human fibroblasts under the stimulation with IL-1 according to the method of J. M. Dayer et al (CACHECTIN/TUMOR NECROSIS FACTOR STIMULATES COLLAGENASE AND PROSTAGLANDIN E$_2$ PRODUCTION BY HUMAN SYNOVIAL CELLS AND DERMAL FIBROBLASTS; J. M. Dayer, B. Beutlerm and A. Cerami, J. Exp. Med., 162,2163–2168, 1985).

As shown in Table Q, the production of prostaglandin E$_2$ was significantly inhibited.

TABLE Q

Inhibitory activity Against the Production of Prostaglandin E$_2$ in Huma Fibroblasts

| Compound No. | IC$_{50}$ (μM) | Compound No. | IC$_{50}$ (μM) | Compound No. | IC$_{50}$ (μM) |
|---|---|---|---|---|---|
| A-3 | 2.4 | A-30 | 0.51 | B-1 | 7.5 |
| A-4 | 4.9 | A-37 | 6.9 | B-2 | 1.9 |
| A-5 | 7.0 | A-38 | 4.9 | B-3 | 2.1 |
| A-6 | 8.2 | A-39 | 6.0 | B-4 | 4.6 |
| A-7 | 4.5 | A-40 | 7.7 | B-5 | 2.0 |
| A-8 | 2.5 | A-41 | 14 | B-6 | 4.7 |
| A-9 | 3.0 | A-42 | 3.8 | B-7 | 3.6 |
| A-11 | 8.5 | A-43 | 8.8 | C-1 | 6.1 |
| A-12 | 1.6 | A-44 | 1.5 | C-2 | 0.40 |
| A-16 | 2.9 | A-45 | 1.5 | C-3 | 7.4 |
| A-17 | 3.2 | A-46 | 1.5 | C-4 | 2.0 |
| A-20 | 0.30 | A-48 | 8.7 | C-5 | 1.2 |
| A-21 | 1.0 | A-52 | 2.9 | C-6 | 2.3 |
| A-23 | 8.6 | A-53 | 0.83 | D-1 | 3.6 |
| A-24 | 4.9 | A-54 | 1.1 | D-2 | 5.7 |
| A-25 | 8.0 | A-55 | 1.1 | D-3 | 7.1 |
| A-26 | 1.8 | A-56 | 0.93 | E-2 | 6.0 |
| A-27 | 2.6 | A-60 | 1.3 | E-4 | 1.9 |
| A-28 | 0.73 | A-61 | 10 | H-8 | 9.9 |
| A-29 | 1.2 | A-62 | 2.2 | H-9 | 9.6 |
| | | | | H-10 | 2.4 |
| | | | | H-11 | 8.5 |
| | | | | H-16 | 1.9 |
| | | | | H-17 | 7.0 |
| | | | | H-18 | 1.5 |
| | | | | J-2 | 9.7 |

Industrial Utility

The compounds of the present invention are capable of inhibiting the activity of cytosolic phospholipase A$_2$ and the production of prostaglandin E$_2$, and are useful in the prevention or treatment of inflammatory diseases such as rheumatoid arthritis, asthma, inflammatory bowel disease, injury due to ischemic reperfusion, allergic rhinitis, and psoriasis.

We claim:

1. A compound of the formula I:

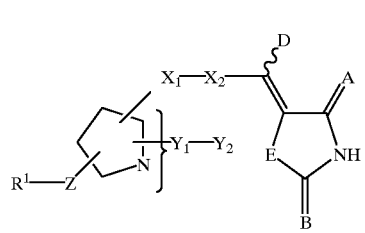

I wherein A and B are independently O or S; E is O or S; $X_1$ is —CO—, —CONH—, —CH$_2$NHSO$_2$—, —CH$_2$NHCO—, —CH$_2$NHCS—, —CH$_2$O—, —OCH$_2$—, —CH$_2$O CH$_2$—, alkylene, alkenylene or a single bond; $X_2$ is substituted or unsubstituted arylene, substituted or unsubstituted indol-diyl or a single bond; D is hydrogen or hydroxyalkyl; $Y_1$ is —(CH$_2$)$_m$CO—, —(CH$_2$)$_n$NHCO—, —(CH$_2$)$_n$NHSO$_2$—, —(CH$_2$)$_m$CONH—, —(CH$_2$)$_m$CSNH—, —(CH$_2$)$_m$SO$_2$—, —(CH$_2$)$_m$COO—, or a single bond; m and n are an integer of 0 to 3; $Y_2$ is hydrogen, alkyl, substituted or unsubstituted alkenyl, substituted or unsubstituted cycloalkyl, substituted or unsubstituted cycloalkenyl, substituted or unusbstituted cycloalkylalkyl, substituted or unsubstituted cycloalkenylalkyl, substituted or unsubstituted aryl, substituted or unsubstituted aralkyl, substituted or unsubstituted heterocyclic group or substituted or unsubstituted amino; Z is —S—, —SO—, —O—, —NH—, —CONH—, —CONHCH$_2$— or a single bond; $R^1$ is hydrogen, substituted or unsubstituted alkyl, substituted or unsubstituted alkenyl, substituted or unsubstituted aryl or substituted or unsubstituted aralkyl, or a pharmaceutically acceptable salt or a hydrate thereof, provided that when $X_1$ is —CH$_2$O—, $Y_1$ is not a single bond; $Y_1$ binds to the pyrrolidine ring at the 1- or 2-position, $X_1$ binds to any positions other than the one to which $Y_1$ binds provided that when $Y_1$ is at the 2-position, $X_1$ binds to the 1-position, and Z binds to any one of the carbon atoms on the pyrrolidine ring other than those to which $X_1$ and $Y_1$ bind; when $Y_1$ binds to the N-atom on the pyrrolidine ring, n is not 0; when $Y_1$ is —(CH$_2$)$_m$COO— and m is 0, $Y_2$ is not a hydrogen atom; and when $X_1$ is —OCH$_2$—, $X_1$ does not bind to the N-atom on the pyrrolidine ring.

2. The compound of claim 1 which is shown by the formula Ia:

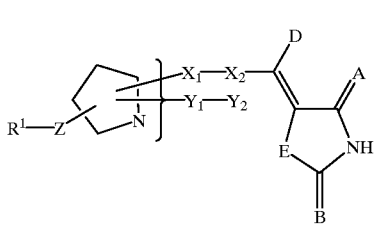

Ia wherein A, B, E, $X_1$, $X_2$, D, $Y_1$, $Y_2$, Z and $R^1$ are as defined above, or a pharmaceutically acceptable salt or a hydrate thereof, provided that when $X_1$ is —CH$_2$O—, $Y_1$ is not a single bond; $Y_1$ binds to the pyrrolidine ring at the 1- or 2-position, and when $Y_1$ binds to the 1-position, $X_1$ binds to the 2-position, and when $Y_1$ binds to the 2-position, $X_1$ binds to the 1-position, and Z binds to any one of carbon atoms on the pyrrolidine ring other than those to which $X_1$ and $Y_1$ bind; when $Y_1$ binds to the N-atom on the pyrrolidine ring, n is not 0; when $Y_1$ is —$(CH_2)_m$COO— and m is 0, $Y_2$ is not hydrogen atom; and when $X_1$ is —OCH$_2$—, it does not bind to the N-atom on the pyrrolidine ring.

3. The compound of claim 1 which shown by the formula Ib:

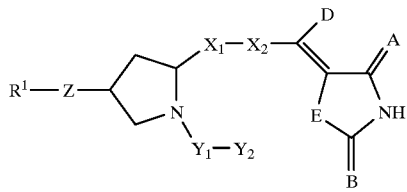

Ib wherein A, B, E, $X_1$, $X_2$, D, $Y_1$, $Y_2$, Z and $R^1$ are as defined above, or a pharmaceutically acceptable salt or a hydrate thereof, provided that when $X_1$ is —CH$_2$O—, $Y_1$ is not a single bond; n is not 0; when $Y_1$ is —$(CH_2)_m$COO— and m is 0, $Y_2$ is not hydrogen atom.

4. The compound of claim 1 which is shown by the formula Ic:

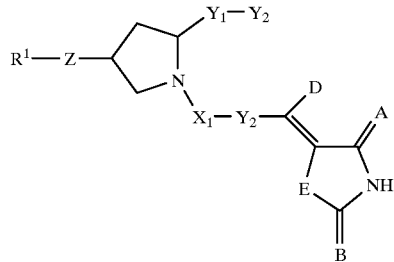

Ic wherein A, B, E, $X_1$, $X_2$, D, $Y_1$, $Y_2$, Z and $R^1$ are as defined above, or a pharmaceutically acceptable salt or a hydrate thereof, provided that when $X_1$ is —CH$_2$O—, $Y_1$ is not a single bond; when $X_1$ is —OCH$_2$—, it does not bind to the N-atom on pyrrolidine ring.

5. The compound of claim 1 which is shown by the formula Id:

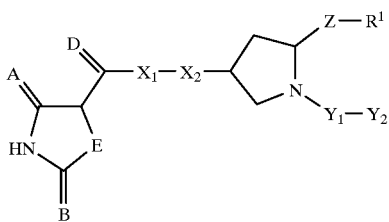

Id wherein A, B, E, $X_1$, $X_2$, D, $Y_1$, $Y_2$, Z and $R^1$ are as defined above, or a pharmaceutically acceptable salt or a hydrate thereof, provided that when $X_1$ is —CH$_2$O—, $Y_1$ is not a single bond; n is not 0; when $Y_1$ is —$(CH_2)_m$COO— and m is 0, $Y_2$ is not hydrogen atom.

6. The compound of claim 1, wherein E is S, and A and B is O, or a pharmaceutically acceptable salt or a hydrate thereof.

7. The compound of claim 1, wherein $X_1$ is —CONH—, —CH$_2$NHSO$_2$— or —CH$_2$NHCO—, or a pharmaceutically acceptable salt or a hydrate thereof.

8. The compound of claim 1, wherein $X_2$ is substituted or unsubstituted phenylene, or a pharmaceutically acceptable salt or a hydrate thereof.

9. The compound of claim 1, wherein $Y_1$ is —CO—, —CONH— or —SO$_2$—, or a pharmaceutically acceptable salt or a hydrate thereof.

10. The compound of claim 1, wherein $Y_2$ is substituted or unsubstituted cycloalkenylalkyl, substituted or unsubstituted aryl, substituted or unsubstituted aralkyl or substituted or an unsubstituted heterocyclic group, or a pharmaceutically acceptable salt or a hydrate thereof.

11. The compound of claim 1, wherein Z is —S— or —O—, or a pharmaceutically acceptable salt or a hydrate thereof.

12. The compound of claim 1, wherein $R^1$ is substituted or unsubstituted alkyl or substituted or unsubstituted aralkyl, or a pharmaceutically acceptable salt or a hydrate thereof.

13. A pharmaceutical composition containing a compound of claim 1.

14. The pharmaceutical composition of claim 13, which is a phospholipase A$_2$inhibitor.

15. The pharmaceutical composition of claim 13, which is an inhibitor against the production of prostaglandin E$_2$.

* * * * *

UNITED STATES PATENT AND TRADEMARK OFFICE
CERTIFICATE OF CORRECTION

PATENT NO.   : 5,955,616
DATED        : September 21, 1999
INVENTOR(S)  : Mitsuaki Ohtani et al.

It is certified that error appears in the above-identified patent and that said Letters Patent is hereby corrected as shown below:

<u>Title page, Item 54, and column 1, line 3</u>
Title should read:
-- PYRROLIDINE DERIVATIVES HAVING PHOSPHOLIPHASE A$_2$ INHIBITORY ACTIVITY AND THEIR COMPOSITIONS --

Signed and Sealed this

Eleventh Day of June, 2002

Attest:

JAMES E. ROGAN
Attesting Officer   Director of the United States Patent and Trademark Office

UNITED STATES PATENT AND TRADEMARK OFFICE
CERTIFICATE OF CORRECTION

PATENT NO.   : 5,955,616
DATED        : September 21, 1999
INVENTOR(S)  : Mitsuaki Ohtani et al.

It is certified that error appears in the above-identified patent and that said Letters Patent is hereby corrected as shown below:

Column 103,
After lines 26-40, please formula Id with the one below:

--

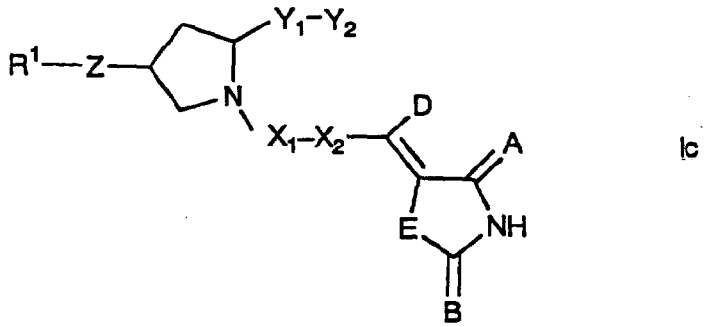

Ic

--

Column 104,
Between lines 1-12, please replace formula Id with the one below:

--

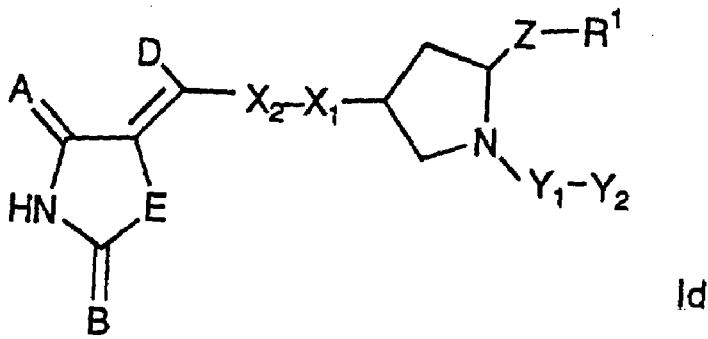

Id

Signed and Sealed this

Eighteenth Day of June, 2002

*Attest:*

*Attesting Officer*

JAMES E. ROGAN
*Director of the United States Patent and Trademark Office*